US005654283A

United States Patent [19]
Townsend et al.

[11] Patent Number: 5,654,283
[45] Date of Patent: Aug. 5, 1997

[54] POLYSUBSTITUTED BENZIMIDAZOLES AS ANTIVIRAL AGENTS

[75] Inventors: Leroy B. Townsend; John C. Drach, both of Ann Arbor, Mich.

[73] Assignee: The Regents of the University of Michigan, Ann Arbor, Mich.

[21] Appl. No.: 467,946

[22] Filed: Jun. 6, 1995

Related U.S. Application Data

[60] Division of Ser. No. 50,470, filed as PCT/US91/08124, Oct. 31, 1991, published as WO92/07867, May 14, 1992, which is a continuation-in-part of Ser. No. 607,899, Nov. 1, 1990, Pat. No. 5,248,672.

[51] Int. Cl.$^6$ .......................... A01N 43/52; C07D 235/04
[52] U.S. Cl. ...................................... 514/43; 548/305.1
[58] Field of Search .......................... 514/258; 548/305.1

[56] References Cited

U.S. PATENT DOCUMENTS

| | | | |
|---|---|---|---|
| 2,860,131 | 11/1958 | Folkers et al. | 536/28.9 |
| 2,935,508 | 5/1960 | Shunk et al. | 536/28.9 |
| 3,037,980 | 6/1962 | Hitchings et al. | 544/280 |
| 3,311,628 | 3/1967 | Partyka | 544/280 |
| 3,631,036 | 12/1971 | Kim et al. | 544/117 |
| 3,686,411 | 8/1972 | Frick et al. | 514/394 |
| 3,817,982 | 6/1974 | Verheyden et al. | 536/27.14 |
| 3,867,386 | 2/1975 | Kim et al. | 544/280 |
| 3,962,211 | 6/1976 | Townsend et al. | 536/27.2 |
| 4,199,574 | 4/1980 | Schaeffer | 514/81 |
| 4,229,453 | 10/1980 | Roth et al. | 514/258 |
| 4,482,708 | 11/1984 | Nguyen | 536/26.5 |
| 4,596,798 | 6/1986 | Shipman, Jr. et al. | 514/183 |
| 4,777,129 | 10/1988 | Dattagupta et al. | 435/6 |
| 4,892,865 | 1/1990 | Townsend et al. | 514/413 |
| 4,927,830 | 5/1990 | Townsend et al. | 514/258 |
| 4,968,686 | 11/1990 | Townsend et al. | 514/258 |
| 5,248,672 | 9/1993 | Townsend et al. | 514/43 |
| 5,360,795 | 11/1994 | Townsend et al. | 514/43 |

FOREIGN PATENT DOCUMENTS

| | | |
|---|---|---|
| 20 20 090 | 11/1970 | Germany. |
| 30 36 390 | 5/1982 | Germany. |
| 31 45 287 | 5/1993 | Germany. |
| 494533 | 9/1970 | Switzerland. |
| 783306 | 9/1957 | United Kingdom. |
| 1306098 | 2/1973 | United Kingdom. |
| WO88/03142 | 5/1988 | WIPO. |

OTHER PUBLICATIONS

Bergstrom, D., et al., "Antiviral Activity of C–5 Substituted Tubercidin Analogues", *J. Med. Chem.*, vol. 27, pp. 285–292 (1984).
DeClercq, E., et al., "Antirhinovirus Activity of Purine Nucleoside Analogs", *Antimicrob. Agents and Chemother.*, vol. 29, No. 3, pp. 482–487 (Mar. 1986).
DeClercq, et al., "Nucleic Acid Related Compounds. 51. Synthesis and Biological Properties of Sugar–Modified Analogues of the Nucleoside Antibiotics Tubercidin, Toyocamycin, Sangivamycin, and Formycin", *J. Med. Chem.*, vol. 30, pp. 481–586 (1987).

Devivar, R.V., et al., "The Formation of an Unusual Product During Studies on the Diazotization of Certain 2–Aminobenzimidazoles", Abstracts of Papers, Part II, 199th ACS National Meeting, Americal Chemical Society (Boston, Massachusetts, Apr. 22–27, 1990), Abstract No. MEDI 24.
Drach, J. et al., "Tritiated Thymidine Incorporation Does Not Measure DNA Synthesis in Ribavirin–Treated Human Cells", *Science*, vol. 212., pp. 549–551 (1981).
Drach, J.C., et al., "Comparison of the Activity of Tubercidin Analogs Against Herpesviruses", abstract presented at 28th ICAAC, Los Angeles, CA on 25 Oct. 1988, 1 page total.
Duffy, T., et al., "Pyrrolo[2,3–d]pyrimidines. Synthesis from 4–Pyrimidiylhydrazones, a 2–Bis(methylthio)methyleneaminopyrrole–3–carbonitrile, and a Pyrrolo–[2,3–d][1,3]thiazine–2(1H)–thione", *J. Chem. Soc. (Perkin Trans. I)*, vol. 16, pp. 1921–1929 (1974).
Gadler, H., "Nucleic Acid Hybridization for Measurment of Effects of Antiviral Compounds on Human Cytomegalovirus DNA Replication", *Antimicrob. Agents and Chemother.*, vol. 24, pp. 370–374 (1983).
Gupta, P.K., et al., "Synthesis, Cytotoxicity, and Antiviral Activity of Some Acyclic Analogs of the Pyrrolo[2,3–d] pyrimidine Nucleoside Antibiotics Tubercidin, Toyocamycin, and Sangivamycin", *J. Med. Chem.*, vol. 32, No. 2, pp. 402–408 (1989).
Hansske, F., et al., "2' and 3'–Ketonucleosides and Their Arabino and Xylo Reduction Products", *Tetrahedron*, vol. 40, No. 1, pp. 125–135 (1984).
Hayflick, B., "Chapter 10: Screening Tissue Cultures for Mycoplasma Infections", in *Tissue Culture: Methods and Applications* (Academic Press, 1973), pp. 722–728.
Jain, T.C., et al., "Reactions of 2–Acyloxyisobutyryl Halides with Nucleosides. III. Reactions of Tubercidin and Formycin", *J. Org. Chem.*, vol. 38, No. 18, pp. 3179–3186 (1973).
Joseph et al., "Dialkylamination by Means of Dimethylformamide (DMF) 2–Dimethylaminobenzimidazoles (1)", *J. Heterocyclic Chem.*, vol. 3(1), pp. 107–108 (1966). (Additional abstract attached).
Maruyama, T., et al., "Pyrrolopyrimidine Nucleosides. 18. Synthesis and Chemotherapeutic Activity of 4–Amino–7–(3–deoxy–β–D–ribofuranosyl)pyrrolo[2,3–d] pyrimidine–5–carboxamide (3'–Deoxysangivamycin) and 4–Amino–7–(2–deoxy–β–D–ribofuranosyl)pyrrolo[2,3–d] pyrimidine–5–carboxamide (2'–Deoxysangivamycin)", *J. Med. Chem.*, vol. 26, pp. 25–29 (1983).
Mitsuya, H., et al., "3'–Azido–3'–deoxythimidine (BW A509U): An Antiviral Agent That Inhibits the Infectivity and Cytopathic Effect of Human T–Lymphotropic Virus Type III/Lymphadenopathy–Associated Vitus In Vitro", *Proc. Natl. Acad. Sci.*, vol. 82, pp. 7096–7100 (Oct. 1985).

(List continued on next page.)

*Primary Examiner*—Gary L. Kunz
*Attorney, Agent, or Firm*—Morrison & Foerster LPP

[57] ABSTRACT

This invention relates to novel polysubstituted benzimidazoles and compositions and their use in the treatment of viral infections. The polysubstituted benzimidazoles and compositions of the present invention exhibit antiviral properties against viruses of the herpes family, particularly human cytomegalovirus (HCMV) and herpes simplex viruses (HSV).

24 Claims, 10 Drawing Sheets

OTHER PUBLICATIONS

Mitsuya, H., et al., "Inhibition of the In Vitro Infectivity and Cytopathic Effect of Human T–Lymphotropic Virus Type III/Lymphadenopathy–Associated Virus (HTLV–III/LAW) by 2', 3'–dideoxynucleosides", *Proc. Natl. Acad. Sci.*, vol. 83, pp. 1911–1915 (Mar. 1986).

Nassiri, M.R., et al., "Kinetic Assessment by Flow Cytometry of the Effect of Two New Antiviral Drugs on the Cell Cycle", abstract presented at 3rd Annual Meeting Clinical Applications of Cytometry, Charleston, SC, 14–17 Sep. 1988, 1 page total.

N'Diaye et al., "Synthese et etude parasitologique de triazino–1,2,4[4,3–a]benzimidazoles", Eur. J. Med. Chem., vol. 22, pp. 403–409 (1987) (including English language abstract).

Pudlo, J.S., et al., "Synthesis and Antiviral Activity of Certain 4–and 4,5–Disubtituted 7–[(2–Hydroxyethoxy)methyl]pyrrolo[2,3–d]pyrimidines", *J. Med. Chem.*, vol. 31, No. 11, pp. 2086–2092 (1988).

Ramasamy, K., et al., "Total Synthesis of 2'–Deoxytoyocamycin, 2'–Deoxysangivamycin and Related 2'–β–D–Arabinofuranosyl–pyrrolo[2,3–d] pyrimidines Via Ring Closure of Pyrrole Precursors Prepared by the Stereospecific Sodium Salt Glycosylation Procedure", Abstracts of Papers, 192th ACS National Meeting, American Chemical Society (Anaheim, California, Sep. 7–12, 1986), Abstract No. 65, 2 pages total.

Ricci et al., "Reattivita nucleofila di alcuni 2–cloro–5(6)–X–benzimidazoli", *Bollettino*, vol. 23, pp. 409–413 (1965) (English language abstract attached).

Robins, M.J., et al., "Nucleic Acid Related Compounds. 24. Transformation of Tubercidin 2',3'–O–orthoacetate into Halo, Deoxy, Epoxide, and Unsaturated Sugar Nucleosides", *Can. J. Chem.*, vol. 55, pp. 1251–1259 (1977).

Robins, M.J., et al., "A Mild Conversion of Vicinal Diols to Alkenes. Efficient Transformation of Ribonucleosides into 2'–ene and 2',3'–dideoxynucleosides", *Tetrahedron Letters*, vol. 25, No. 4, pp. 367–370 (1984).

Saluja, S., et al., "Synthesis and Antiviral Activity of Certain 2–Substituted 4,5,6,7–Tetrachlorobenzimidazole Acyclic Nucleosides", Abstracts of Papers, Part II, 199th ACS National Meeting, Americal Chemical Society (Boston, Massachusetts, Apr. 22–27, 1990), Abstract No. MEDI 22.

Saxena, N.K., et al., "Synthesis and Antiviral Activity of Certain 4–Substituted and 2,4–Disubstituted 7–[(2–Hydroxylethoxy)methyl]pyrrolo[2,3–d]pyrimidines", *J. Med. Chem.*, vol. 31, No. 8, pp. 1501–1506 (1988).

Shipman, C., Jr., "Antiviral Activity of Arabinosyladenine and Arabinosylhypoxanthine in Herpes Simplex Virus–Infected KB Cells: Selective Inhibition of Viral Deoxyribonucleic Acid Synthesis in Synchronized Suspension Cultures", *Antimicrob. Agents and Chemother.*, vol. 9, No. 1, pp. 120–127 (Jan. 1976).

Shipman, C., Jr., et al., "Evaluation of 4–(2–Hydroxyethyl)–1–piperazineethanesulfonic Acid (HEPES) as Tissue Culture Buffer", *Proc. Soc. Exp. Biol. Med.*, vol. 120, pp. 305–310 (1969).

Sigma Chemical Company Catalog, St. Louis, MO., 1984, p.898 lists tubercidin.

Smith, C.M., et al., "Inhibitors of Hypoxanthine Metabolism in Ehrlich Ascites Tumor Cells In Vitro", *Cancer Treatment Reports*, vol. 60, No. 10, pp. 1567–1582 (Oct. 1976).

Tamm, I., et al., "Inhibition of Influenza and Mumps Virus Multiplication by 4,5,6–(or 5,6,7–) Trichloro–1–β–D–Ribofuranosylbenzimidazole", *Science*, vol. 120, pp. 847–848, (Nov. 1954).

Tolman, R.L., et al., "Pyrrolopyrimidine Nucleosides. III. The Total Synthesis of Toyacamycin, Sangivamycin, Tubercidin, and Related Derivatives", *J. Amer. Chem. Soc.*, vol. 91, No. 8, pp. 2102–2108 (Apr. 1969).

Townsend, L.B., et al., "Benzimidazole Nucleosides, Nucleotides, and Related Derivatives", *Chemical Reviews*, vol. 70, pp. 389–438 (1970).

Turk, S.R., et al., "Pyrrolo[2,3–d]Pyrimidine Nucleosides as Inhibitors of Human Cytomegalovirus", *Antimicrob. Agents and Chemother.*, vol. 31, No. 4, pp. 544–550 (Apr. 1987).

Vindelov, L.L., "Flow Microfluorometric Analysis of Nuclear DNA in Cells from Solid Tumors and Cell Suspensions", *Virchow's Arch. B Cell Path.*, vol. 24, pp. 227–242 (1977).

Zou, R., et al., "Synthesis and Antiviral Activity of 1–β–D–Ribofuranosyl–2,4,6–Trichlorobenzimidazole", Abstracts of Papers, Part II, 199th National Meeting, Americal Chemical Society (Boston, Massachusetts, Apr. 22–27, 1990), Abstract No. MEDI 23.

| Compound # | $R_1$ | $R_2$ | $R_3$ | $R_4$ | $R_5$ |
|---|---|---|---|---|---|
| 11 | H | F | F | H | $NH_2$ |
| 12 | H | F | F | H | Cl |
| 12b | H | Cl | F | H | $NH_2$ |
| 12c | H | Cl | F | H | Cl |
| 13 | Cl | Cl | Cl | H | Cl |
| 13b | Cl | Cl | Cl | H | $NH_2$ |
| 17 | H | Br | Br | H | Cl |
| 19 | H | $NO_2$ | H | H | Cl |
| 20 | Br | Br | Br | H | Cl |
| 25 | H | $NH_2$ | $NO_2$ | H | Cl |
| 26 | H | I | $NO_2$ | H | Cl |
| 26a | H | I | $NH_2$ | H | Cl |
| 34 | H | Cl | H | H | $NH_2$ |
| 35 | H | Cl | H | H | Cl |
| 41 | H | I | I | H | Cl |
| 41b | Cl | H | $CF_3$ | H | $NH_2$ |
| 41c | Cl | H | $CF_3$ | H | Cl |

| Compound # | R | $R_1$ | $R_2$ | $R_3$ | $R_4$ | $R_5$ |
|---|---|---|---|---|---|---|
| 45 | H | H | Cl | Cl | H | Cl |
| 52 | H | H | Cl | Cl | H | Br |
| 60 | Ac | H | $NO_2$ | $NO_2$ | H | Cl |
| 61 | H | H | $NO_2$ | $NO_2$ | H | Cl |
| 80 | Ac | Cl | H | Cl | H | Cl |
| 81 | H | Cl | H | Cl | H | Cl |
| 83a | H | H | Cl | Cl | H | I |
| 84 | Ac | Br | Br | H | H | Cl |
| 85 | H | Br | Br | H | H | Cl |
| 95 | H | H | Br | Cl | H | Cl |
| 99 | H | H | Cl | Br | H | Cl |
| 107 | H | H | I | I | H | Cl |

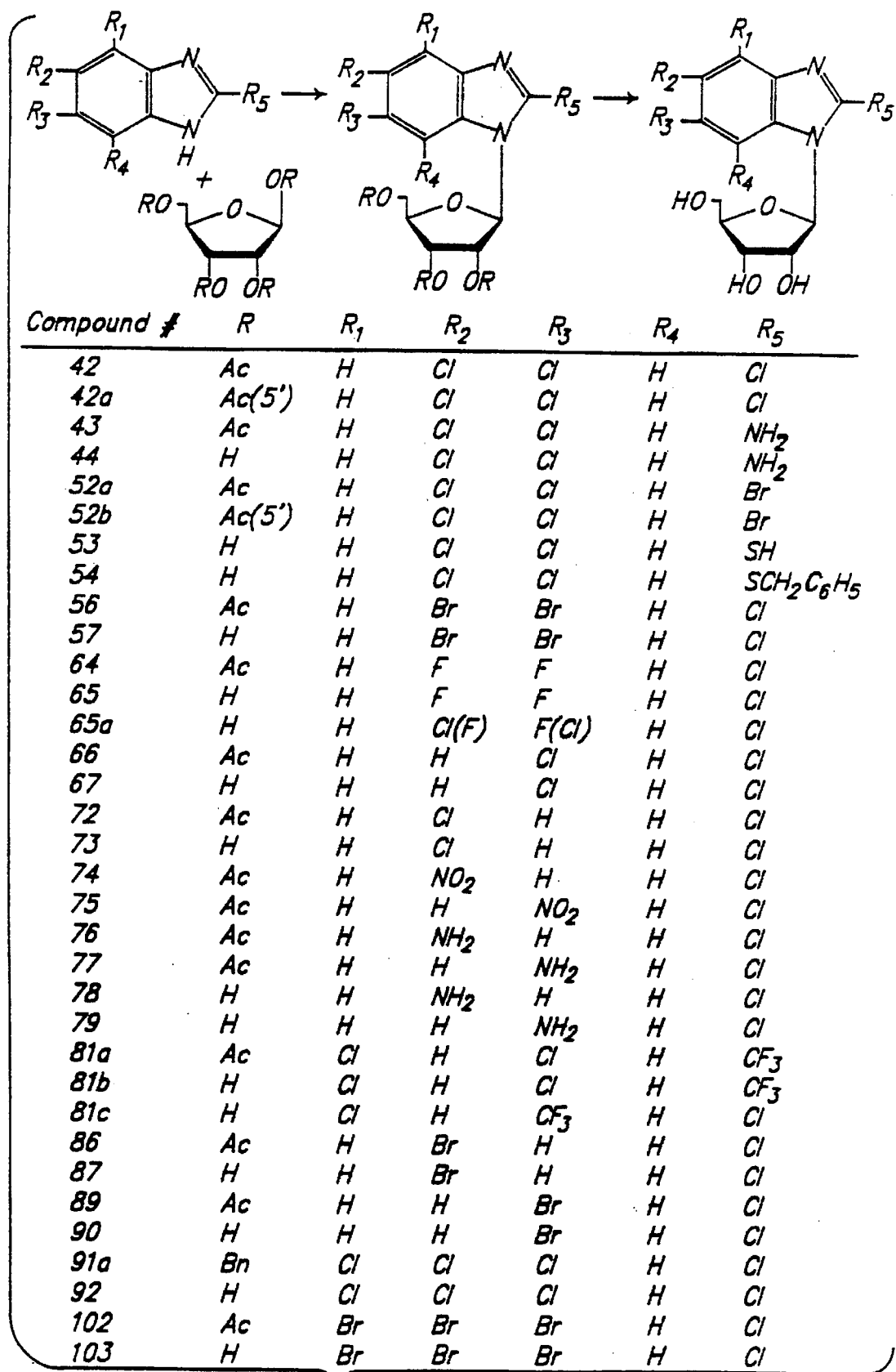

| Compound # | R | $R_1$ | $R_2$ | $R_3$ | $R_4$ | $R_5$ |
|---|---|---|---|---|---|---|
| 42 | Ac | H | Cl | Cl | H | Cl |
| 42a | Ac(5') | H | Cl | Cl | H | Cl |
| 43 | Ac | H | Cl | Cl | H | $NH_2$ |
| 44 | H | H | Cl | Cl | H | $NH_2$ |
| 52a | Ac | H | Cl | Cl | H | Br |
| 52b | Ac(5') | H | Cl | Cl | H | Br |
| 53 | H | H | Cl | Cl | H | SH |
| 54 | H | H | Cl | Cl | H | $SCH_2C_6H_5$ |
| 56 | Ac | H | Br | Br | H | Cl |
| 57 | H | H | Br | Br | H | Cl |
| 64 | Ac | H | F | F | H | Cl |
| 65 | H | H | F | F | H | Cl |
| 65a | H | H | Cl(F) | F(Cl) | H | Cl |
| 66 | Ac | H | H | Cl | H | Cl |
| 67 | H | H | H | Cl | H | Cl |
| 72 | Ac | H | Cl | H | H | Cl |
| 73 | H | H | Cl | H | H | Cl |
| 74 | Ac | H | $NO_2$ | H | H | Cl |
| 75 | Ac | H | H | $NO_2$ | H | Cl |
| 76 | Ac | H | $NH_2$ | H | H | Cl |
| 77 | Ac | H | H | $NH_2$ | H | Cl |
| 78 | H | H | $NH_2$ | H | H | Cl |
| 79 | H | H | H | $NH_2$ | H | Cl |
| 81a | Ac | Cl | H | Cl | H | $CF_3$ |
| 81b | H | Cl | H | Cl | H | $CF_3$ |
| 81c | H | Cl | H | $CF_3$ | H | Cl |
| 86 | Ac | H | Br | H | H | Cl |
| 87 | H | H | Br | H | H | Cl |
| 89 | Ac | H | H | Br | H | Cl |
| 90 | H | H | H | Br | H | Cl |
| 91a | Bn | Cl | Cl | Cl | H | Cl |
| 92 | H | Cl | Cl | Cl | H | Cl |
| 102 | Ac | Br | Br | Br | H | Cl |
| 103 | H | Br | Br | Br | H | Cl |

FIG. 1b.

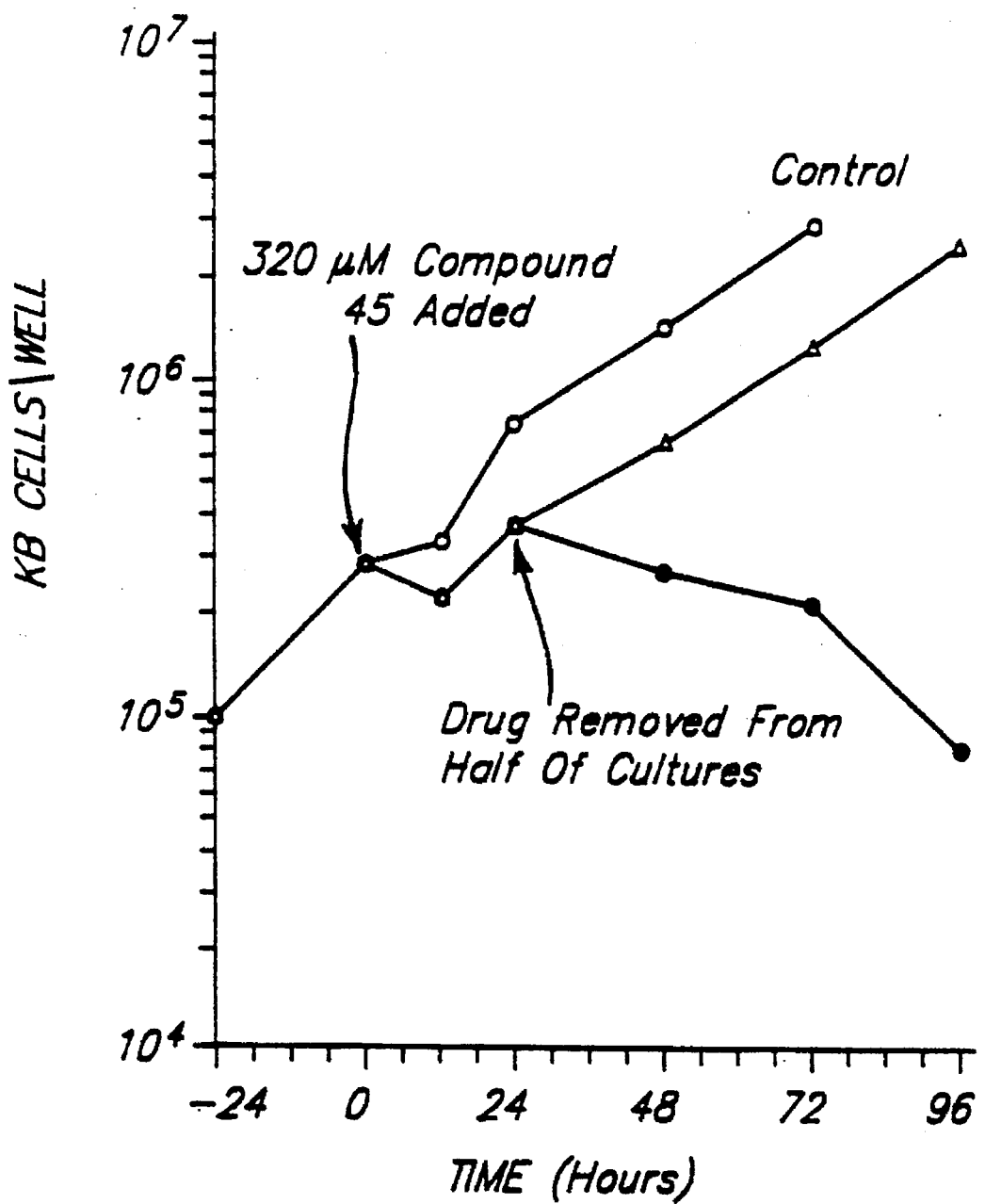

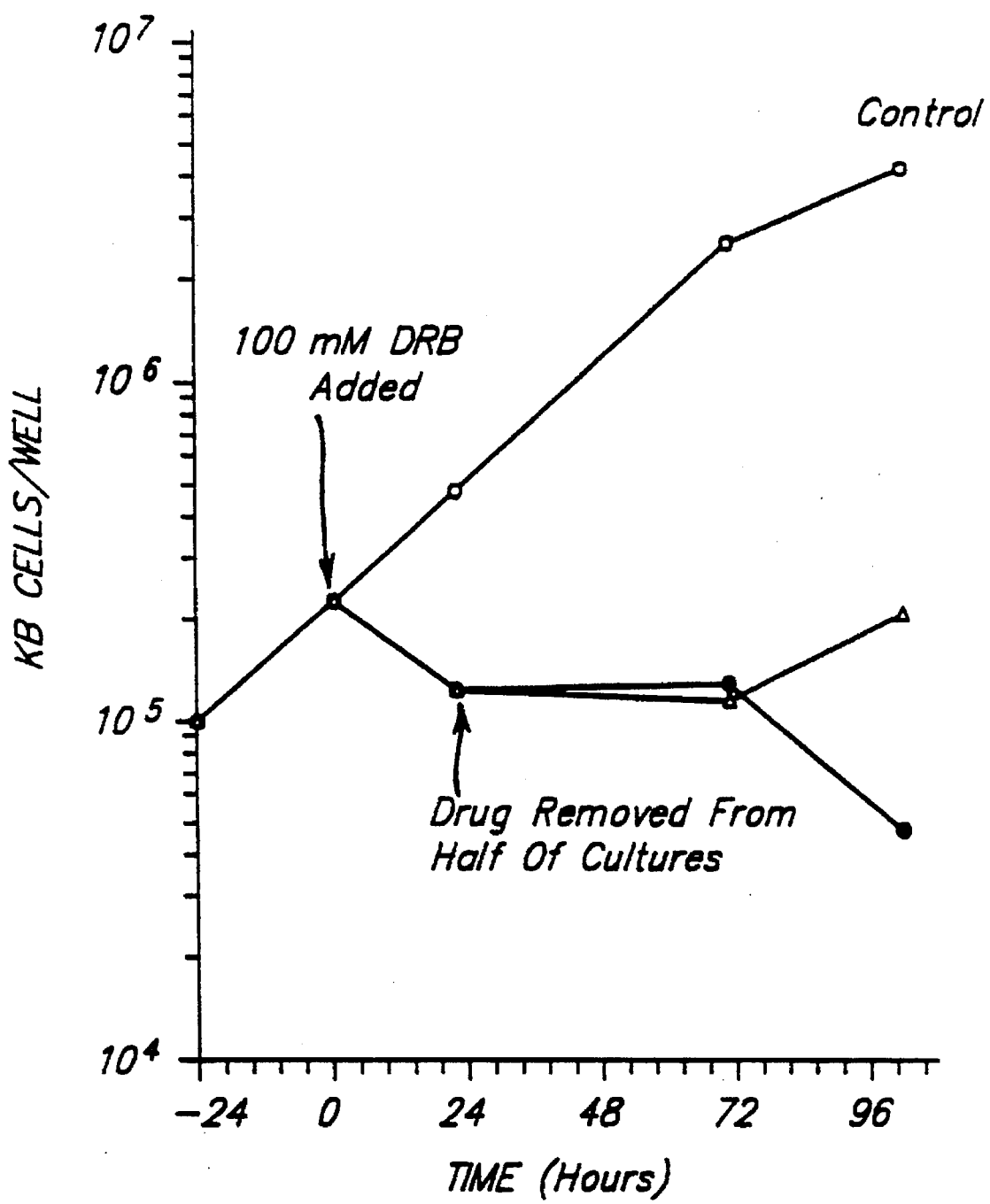
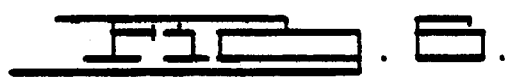

POLYSUBSTITUTED BENZIMIDAZOLES AS ANTIVIRAL AGENTS

RELATED APPLICATIONS

This application is a divisional application of United States Patent application Ser. No. 08/050,470, filed as PCT/US91/08124, Oct. 31, 1991, published as WO92/07867, May 14, 1992, allowed; which is a continuation-in-part application of United States patent application Ser. No. 07/607,899, filed 01 Nov. 1990, now issued U.S. Pat. No. 5,248,672.

SPONSORSHIP

This invention was made with government support under Contract No. NO1 AI 42554 and NO1 AI 72641 awarded by the National Institute of Allergy end Infectious Diseases of the National Institutes of Health. The government has certain rights in this invention.

FIELD OF THE INVENTION

The present invention relates generally to polysubstituted benzimidazoles and, more particularly, to novel polysubstituted benzimidazoles and compositions, their preparation and their use as antiviral agents, particularly against human cytomegalovirus and herpes simplex virus.

BACKGROUND OF THE INVENTION

Antiviral activity of polysubstituted benzimidazoles such as 5,6-dichloro-1-(β-D-ribofuranosyl) benzlmidazole (DRB) and some closely related derivatives has been previously described. Their activity against specific viruses, such as RNA rhinovirus and DNA herpes simplex virus type 1 and type2, has also been reported.

Benzimldazole nucleosides are particularly attractive as potential antiviral agents because of their stability toward some major pathways of bioactive purine (bicyclic) nucleoside inactivation, e.g., deamination by adenosine deaminase and glycosidic bond cleavage by purine nucleoside phosphorylases. Benzimidazole nucleosides such as DRB have, however, demonstrated only marginal levels of activity or generally unacceptable levels of cytotoxicity, or both, thereby greatly diminishishing their usefulness in the treatment of vital infections. It would thus be desirable to provide polysubstituted benzimidazoles and compositions thereof having good antiviral properties, preferably with a low degree of cytotoxicity.

SUMMARY OF THE INVENTION

The present invention relates to novel antiviral compositions comprising a polysubstituted benzimidazole and a pharmaceutically acceptable carrier and methods of treatment therewith, wherein the polysubstituted benzimidazole is selected from the group consisting of compounds having the following formula and pharmaceutically acceptable salts and formulations thereof:

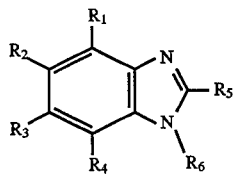

wherein
$R_1$ is H, $R_2$ is Cl, $R_3$ is Cl, $R_4$ is H, $R_5$ is Cl and $R_6$ is β-D-ribofuranosyl (denoted compound 45 in the text);
$R_1$ is H, $R_2$ is Cl, $R_3$ is Cl, $R_4$ is H, $R_5$ is Br and $R_6$ is β-D-ribofuranosyl (denoted compound 52 in the text);
$R_1$ is H, $R_2$ is $NO_2$, $R_3$ is $NO_2$, $R_4$ is H, $R_5$ is Cl and $R_6$ is β-D-ribofuranosyl (denoted compound 61 in the text);
$R_1$ is Cl, $R_2$ is H, $R_3$ is Cl, $R_4$ is H, $R_5$ is Cl and $R_6$ is β-D-ribofurenosyl (denoted compound 81 in the text);
$R_1$ is H, $R_2$ is Cl, $R_3$ is Cl, $R_4$ is H, $R_5$ is I and $R_6$ is β-D-ribofuranosyl (denoted compound 83a in the text);
$R_1$ Is Br, $R_2$ is Br, $R_3$ is H, $R_4$ is H, $R_5$ is Cl and $R_6$ is β-D-ribofuranosyl (denoted compound 85 in the text);
$R_1$ is H, $R_2$ is Br, $R_3$ is Cl, $R_4$ is H, $R_5$ is Cl and $R_6$ is β-D-ribofuranosyl (denoted compound 95 in the text);
$R_1$ is H, $R_2$ is Cl, $R_3$ is Br, $R_4$ is H, $R_5$ is Cl and $R_6$ is β-D-ribofuranosyl (denoted compound 99 in the text);
$R_1$ is H, $R_2$ is I, $R_3$ is I, $R_4$ is H, $R_5$ is Cl and $R_6$ is β-D-ribofuranosyl (denoted compound 107 in the text);
$R_1$ is H, $R_2$ is Cl, $R_3$ is Cl, $R_4$ is H, $R_5$ is Cl and $R_6$ is 2'-deoxy-β-D-erythro-pentofuranosyl (denoted compound 111 in the text);
$R_1$ is H, $R_2$ is Cl, $R_3$ is Cl, $R_4$ is H, $R_5$ is Br and $R_6$ is 2'-deoxy-β-D-erythro-pentofuranosyl (denoted compound 112 in the text);
$R_1$ is H, $R_2$ is Cl, $R_3$ is Cl, $R_4$ is H, $R_5$ is Br and $R_6$ is H (denoted compound 7 in the text);
$R_1$ is H, $R_2$ is Cl, $R_3$ is F, $R_4$ is H, $R_5$ is Cl and $R_6$ is H (denoted compound 12c in the text);
$R_1$ is Cl, $R_2$ is Cl, $R_3$ is Cl, $R_4$ is H, $R_5$ is Cl and $R_6$ is H (denoted compound 13 in the text);
$R_1$ is H, $R_2$ is $NO_2$, $R_3$ is H, $R_4$ is H, $R_5$ is Cl and $R_6$ is H (denoted compound 19 in the text);
$R_1$ is H, $R_2$ is I, $R_3$ is $NO_2$, $R_4$ is H, $R_5$ is Cl and $R_6$ is H (denoted compound 26 in the text);
$R_1$ is Cl, $R_2$ is H, $R_3$ is Cl, $R_4$ is H, $R_5$ is Cl and $R_6$ is H (denoted compound 32 in the text);
$R_1$ is H, $R_2$ is I, $R_3$ is I, $R_4$ is H, $R_5$ is Cl and $R_6$ is H (denoted compound 41 in the text);
$R_1$ is Cl, $R_2$ is H, $R_3$ is $CF_3$, $R_4$ is H, $R_5$ is Cl and $R_6$ is H (denoted compound 41c in the text);
$R_1$ is H, $R_2$ is Cl, $R_3$ is Cl, $R_4$ is H, $R_5$ is $NH_2$ and $R_6$ is β-D-ribofuranosyl (denoted compound 44 in the text);
$R_1$ is H, $R_2$ is Cl, $R_3$ is Cl, $R_4$ is H, $R_5$ is $NH_2$ and $R_6$ is β-D-ribofuranosyl (denoted compound 54 in the text);
$R_1$ is H, $R_2$ is Br, $R_3$ is Br, $R_4$ is H, $R_5$ is Cl and $R_6$ is β-D-ribofuranosyl (denoted compound 57 in the text);
$R_1$ is H, $R_2$ is F, R3 is F, $R_4$ is H, $R_5$ is Cl and $R_6$ is β-D-ribofuranosyl (denoted compound 65 in the text);
$R_1$ Is H, $R_2$ is Cl, $R_3$ is F, $R_4$ is H, $R_5$ is Cl and $R_6$ is β-D-ribofuranosyl (denoted compound 65a in the text);
$R_1$ is H, $R_2$ is H, $R_3$ is Cl, $R_4$ is H, $R_5$ is Cl and $R_6$ is β-D-ribofuranosyl (denoted compound 67 in the text);
$R_1$ is Cl, $R_2$ is H, $R_3$ is Cl, $R_4$ is H, $R_5$ is $CF_3$ and $R_6$ is β-D-ribofuranosyl (denoted compound 81b in the text);
$R_1$ is Cl, $R_2$ is H, $R_3$ is $CF_3$, $R_4$ is H, $R_5$ is Cl and $R_6$ is β-D-ribofuranosyl (denoted compound 81c in the text);
$R_1$ is H, $R_2$ is Br, $R_3$ is H, $R_4$ is H, $R_5$ is Cl and $R_6$ is β-D-ribofuranosyl (denoted compound 87 in the text);
$R_1$ is H, $R_2$ is H, $R_3$ is Br, $R_4$ is H, $R_5$ is Cl and $R_6$ is β-D-ribofuranosyl (denoted compound 90 in the text);
$R_1$ is Cl, $R_2$ is Cl, $R_3$ is Cl, $R_4$ is H, $R_5$ Is Cl and $R_6$ is β-D-ribofuranosyl (denoted compound 92 in the text);
$R_1$ is Br, $R_2$ is Br, $R_3$ is Br, $R_4$ is H, $R_5$ is Cl and $R_6$ is β-D-ribofuranosyl (denoted compound 103 in the text);
$R_1$ is H, $R_2$ is Cl, $R_3$ is Cl, $R_4$ is H, $R_5$ is $NH_2$ and $R_6$ is 2'-deoxy-β-D-erythro-pentofuranosyl (denoted compound 113 in the text);

$R_1$ is H, $R_2$ is Cl, $R_3$ is Cl, $R_4$ is H, $R_5$ is Cl and $R_6$ is β-D-arabinofuranosyl (denoted compound 134 in the text);

$R_1$ is Cl, $R_2$ is Cl, $R_3$ is Cl, $R_4$ is Cl, $R_5$ is Cl and $R_6$ is (1,3-dihydroxy-2-propoxy)methyl (denoted compound 155 in the text);

$R_1$ is Cl, $R_2$ is Cl, $R_3$ is Cl, $R_4$ is Cl, $R_5$ is $NH_2$ and $R_6$ is (1,3-dihydroxy-2-propoxy)methyl (denoted compound 156 in the text);

$R_1$ is Cl, $R_2$ is Cl, $R_3$ is Cl, $R_4$ is Cl, $R_5$ is Cl and $R_6$ is 2-hydroxyethoxymethyl (denoted compound 166 in the text);

$R_1$ is Cl, $R_2$ is Cl, $R_3$ is Cl, $R_4$ is Cl, $R_5$ is $OCH_3$ and $R_6$ is 2-hydroxyethoxymethyl (denoted compound 166a in the text);

$R_1$ is Cl, $R_2$ is Cl, $R_3$ is Cl, $R_4$ is Cl, $R_5$ is $NH_2$ and $R_6$ is 2-hydroxyethoxymethyl (denoted compound 167 in the text);

$R_1$ is H, $R_2$ is Cl, $R_3$ is Cl, $R_4$ is H, $R_5$ is $NH_2$ and $R_6$ is benzyl (denoted compound 182 in the text);

$R_1$ is H, $R_2$ is Cl, $R_3$ is Cl, $R_4$ is H, $R_5$ is Cl and $R_6$ is 5-O-acetyl-β-D-ribofuranosyl (denoted compound 42a in the text);

$R_1$ is H, $R_2$ is Cl, $R_3$ is Cl, $R_4$ is H, $R_5$ is Br and $R_6$ is 5-O-acetyl-β-D-ribofuranosyl (denoted compound 52b in the text);

$R_1$ is H, $R_2$ is Cl, $R_3$ is Cl, $R_4$ is H, $R_5$ is Cl and $R_6$ is 2,3,5-tri-O-acetyl-β-D-ribofuranosyl (denoted compound 42 in the text);

$R_1$ is H, $R_2$ is Cl, $R_3$ is Cl, $R_4$ is H, $R_5$ is Br and $R_6$ is 2,3,5-tri-O-acetyl-β-D-ribofuranosyl (denoted compound 52a in the text);

and operative combinations thereof.

As used herein, by "pharmaceutically acceptable carrier" is meant any composition, solvent, dispersion medium, coating, delivery vehicle or the like, which can be employed to administer the compounds and compositions of the present invention without undue adverse physiological effects. By "combination" is meant any chemically compatible combination of the compounds which does not eliminate the antiviral activity of the composition.

The present invention also relates to a method of antiviral treatment generally comprising the step of administering to the viral host a therapeutically effective amount of a polysubstituted benzimidazole selected from the above-described group. By "therapeutically effective amount" is meant an amount generally effective to achieve the desired antiviral effect.

The present invention further relates to the use of a polysubstituted benzimidazole selected from the above-described group in the manufacturing of medicaments for antiviral use. The present invention also relates to compositions comprising a polysubstituted benzimidazole selected from the above-described group in combination with other antiviral agents outside the group.

The present invention further relates to the novel polysubstituted benzimidazoles used in the compositions and treatments of the present invention and methods of their making. Novel benzimidazoles include compounds 52, 61, 83a, 85, 95, 99, 107, 111, 112, 7, 12c, 13, 19, 26, 32, 41, 41c, 57, 65, 65a, 67, 81b, 81c, 87, 90, 92, 103, 113, 134, 182, 42a, 52b, 42, 52a, 81, 155, 156, 166, 166a, 167.

BRIEF DESCRIPTION OF THE DRAWINGS AND TABLES

FIGS. 1a, 1b, 2, 2a, 2b, 2c, 2d, and 2e are synthesis schemes and substituent charts of polysubstituted benzimidazoles in accordance with and illustrating the principles of the present invention.

FIG. 5 is a graph illustrating the reversibility of the cytotoxic effects produced by a very high level of a polysubstituted benzimidazole nucleoside (compound 45) in accordance with the principles of the present invention.

FIG. 6 is a graph illustrating the cytotoxic effects of DRB on cell growth and its irreversibility.

Figure 1:
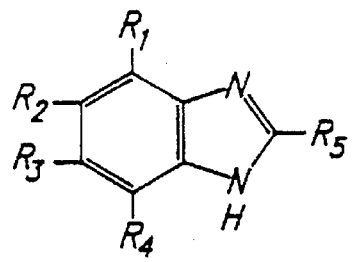
Figure 1A:
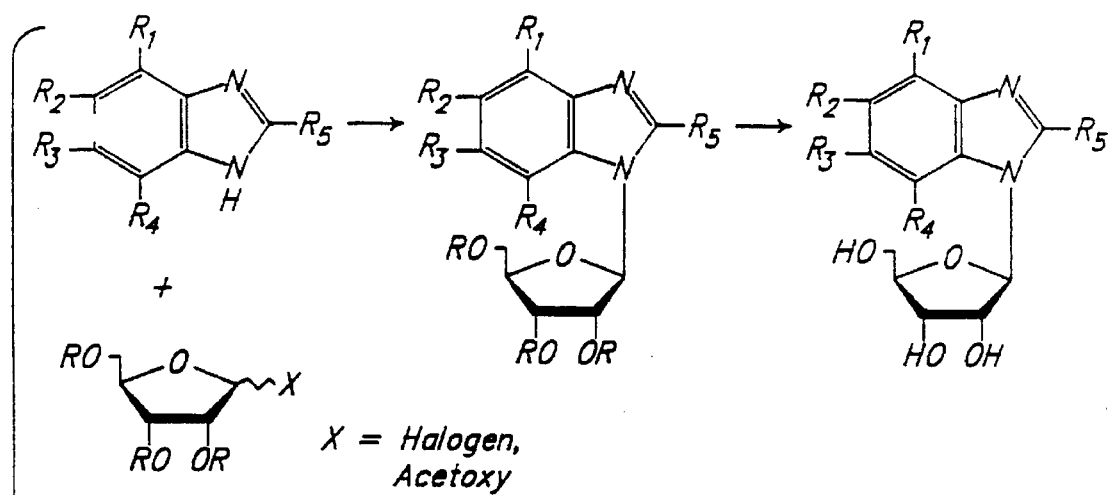

Table 1 illustrates the antiviral activity and cytotoxicity of polysubstituted benzimidazoles in accordance with the principles of the present invention.

Table 2 illustrates the effects of a polysubstituted benzimidazole nucleoside on the replication of selected herpes viruses in accordance with the principles of the present invention.

Table 3 illustrates the antiviral activity and cytotoxicity of polysubstituted benzimidazoles in accordance with the principles of the present invention.

DETAILED DESCRIPTION OF THE PREFERRED EMBODIMENTS

A. Chemical Structure of Polysubstituted Benzimidazoles of the Invention

Novel antiviral compositions of the present invention comprise a polysubstituted benzimidazole and a pharmaceutically acceptable carrier, wherein the polysubstituted benzimidazole is selected from the group consisting of compounds having the following formula and pharmaceutically acceptable salts and formulations thereof:

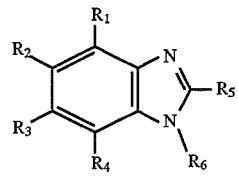

wherein $R_1$ is H, $R_2$ is Cl, $R_3$ is Cl, $R_4$ is H, $R_5$ is Cl and $R_6$ is β-D-ribofuranosyl (denoted compound 45 in the text);

$R_1$ is H, $R_2$ is Cl, $R_3$ is Cl, $R_4$ is H, $R_5$ is Br and $R_6$ is β-D-ribofuranosyl (denoted compound 52 in the text);

$R_1$ is H, $R_2$ is $NO_2$, $R_3$ is $NO_2$, $R_4$ is H, $R_5$ is Cl and $R_6$ is β-D-ribofuranosyl (denoted compound 61 in the text);

$R_1$ is Cl, $R_2$ is H, $R_3$ is Cl, $R_4$ is H, $R_5$ is Cl and $R_6$ is β-D-ribofuranosyl (denoted compound 81 in the text);

$R_1$ is H, $R_2$ is Cl, $R_3$ is Cl, $R_4$ is H, $R_5$ is I and $R_6$ is β-D-ribofuranosyl (denoted compound 83a in the text);

$R_1$ is Br, $R_2$ is Br, $R_3$ is H, $R_4$ is H, $R_5$ is Cl and $R_6$ is β-D-ribofuranosyl (denoted compound 85 in the text);

$R_1$ is H, $R_2$ is Br, $R_3$ is Cl, $R_4$ is H, $R_5$ is Cl and $R_6$ is β-D-ribofuranosyl (denoted compound 95 in the text);

$R_1$ is H, $R_2$ is Cl, $R_3$ is Br, $R_4$ is H, $R_5$ is Cl and $R_6$ is β-D-ribofuranosyl (denoted compound 99 in the text);

$R_1$ is H, $R_2$ is I, $R_3$ is I, $R_4$ is H, $R_5$ is Cl and $R_6$ is β-D-ribofuranosyl (denoted compound 107 in the text);

$R_1$ is H, $R_2$ is Cl, $R_3$ is Cl, $R_4$ is H, $R_5$ is Cl and $R_6$ is 2'-deoxy-β-D-erythro-pentofuranosyl (denoted compound 111 in the text);

$R_1$ is H, $R_2$ is Cl, $R_3$ is Cl, $R_4$ is H, $R_5$ is Br and $R_6$ is 2'-deoxy-β-D-erythro-pentofuranoxyl (denoted compound 112 in the text);

$R_1$ is H; $R_2$ is Cl, $R_3$ is Cl, $R_4$ is H, $R_5$ is Br and $R_6$ is H (denoted compound 7 in the text);

$R_1$ is H, $R_2$ is Cl, $R_3$ is F, $R_4$ is H, $R_5$ is Cl and $R_6$ is H (denoted compound 12c in the text);

$R_1$ is Cl, $R_2$ is Cl, $R_3$ is Cl, $R_4$ is H, $R_5$ is Cl and $R_6$ is H (denoted compound 13 in the text);

$R_1$ is H, $R_2$ is $NO_2$, $R_3$ is H, $R_4$ is H, $R_5$ is Cl and $R_6$ is H (denoted compound 19 in the text);

$R_1$ is H, $R_2$ is I, $R_3$ is $NO_2$, $R_4$ is H, $R_5$ is Cl and $R_6$ is H (denoted compound 26 in the text);

$R_1$ is Cl, $R_2$ is H, $R_3$ is Cl, $R_4$ is H, $R_5$ is Cl and $R_6$ is H (denoted compound 32 in the text);

$R_1$ is H, $R_2$ is I, $R_3$ is I, $R_4$ is H, $R_5$ is Cl and $R_6$ is H (denoted compound 41 in the text);

$R_1$ is Cl, $R_2$ is H, $R_3$ is $CF_3$, $R_4$ is H, $R_5$ is Cl and $R_6$ is H (denoted compound 41c in the text);

$R_1$ is H, $R_2$ is Cl, $R_3$ is Cl, $R_4$ is H, $R_5$ is $NH_2$ and $R_6$ is β-D-ribofuranosyl (denoted compound 44 in the text);

$R_1$ is H, $R_2$ is Cl, $R_3$ is Cl, $R_4$ is H, $R_5$ is $SCH_2C_6H_5$ and $R_6$ is β-D-ribofuranosyl (denoted compound 54 in the text);

$R_1$ is H, $R_2$ is Br, $R_3$ is Br, $R_4$ is H, $R_5$ is Cl and $R_6$ is β-D-ribofuranosyl (denoted compound 57 in the text);

$R_1$ is H, $R_2$ is F, $R_3$ is F, $R_4$ is H, $R_5$ is Cl and $R_6$ is β-D-ribofuranosyl (denoted compound 65 in the text);

$R_1$ is H, $R_2$ is Cl, $R_3$ is F, $R_4$ is H, $R_5$ is Cl and $R_6$ is β-D-ribofuranosyl (denoted compound 65a in the text);

$R_1$ is H, $R_2$ is H, $R_3$ is Cl, $R_4$ is H, $R_5$ is Cl and $R_6$ is β-D-ribofuranosyl (denoted compound 67 in the text);

$R_1$ is Cl, $R_2$ is H, $R_3$ is Cl, $R_4$ is H, $R_5$ is $CF_3$ and $R_6$ is β-D-ribofuranosyl (denoted compound 81b in the text);

$R_1$ is Cl, $R_2$ is H, $R_3$ is $CF_3$, $R_4$ is H, $R_5$ is Cl and $R_6$ is β-D-ribofuranosyl (denoted compound 81c in the text);

$R_1$ is H, $R_2$ is Br, $R_3$ is H, $R_4$ is H, $R_5$ is Cl and $B_6$ is β-D-ribofuranosyl (denoted compound 87 in the text);

$R_1$ is H, $R_2$ is H, $R_3$ is Br, $R_4$ is H, $R_5$ is Cl and $R_6$ is β-D-ribofuranosyl (denoted compound 90 in the text);

$R_1$ is Cl, $R_2$ is Cl, $R_3$ is Cl, $R_4$ is H, $R_5$ is Cl and $R_6$ is β-D-ribofuranosyl (denoted compound 92 in the text);

$R_1$ is Br, $R_2$ is Br, $R_3$ is Br, $R_4$ is H, $R_5$ is Cl and $R_6$ is β-D-ribofuranosyl (denoted compound 103 in the text);

$R_1$ is H, $R_2$ is Cl, $R_3$ is Cl, $R_4$ is H, $R_5$ is $NH_2$ and $R_6$ is 2'-deoxy-β-D-erythro-pentofuranosyl (denoted compound 113 in the text);

$R_1$ is H, $R_2$ is Cl, $R_3$ is Cl, $R_4$ is H, $R_5$ is Cl and $R_6$ is β-D-arabinofuranosyl (denoted compound 134 in the text);

$R_1$ is Cl, $R_2$ is Cl, $R_3$ is Cl, $R_4$ is Cl, $R_5$ is Cl and $R_6$ is (1,3-dihydroxy-2-propoxy)methyl (denoted compound 155 in the text);

$R_1$ is Cl, $R_2$ is Cl, $R_3$ is Cl, $R_4$ is Cl, $R_5$ is $NH_2$ and $R_6$ is (1,3-dihydroxy-2-propoxy)methyl (denoted compound 156 in the text);

$R_1$ is Cl, $R_2$ is Cl, $R_3$ is Cl, $R_4$ is Cl, $R_5$ is Cl and $R_6$ is 2-hydroxyethoxymethyl (denoted compound 166 in the text);

$R_1$ is Cl, $R_2$ is Cl, $R_3$ is Cl, $R_4$ is Cl, $R_5$ is $OCH_3$ and $R_6$ is 2-hydroxyethoxymethyl (denoted compound 166a in the text);

$R_1$ is Cl, $R_2$ is Cl, $R_3$ is Cl, $R_4$ is Cl, $R_5$ is $NH_2$ and $R_6$ is 2-hydroxyethoxymethyl (denoted compound 167 in the text);

$R_1$ is H, $R_2$ is Cl, $R_3$ is Cl, $R_4$ is H, $R_5$ is $NH_2$ and $R_6$ is benzyl (denoted compound 182 in the text);

$R_1$ is H, $R_2$ is Cl, $R_3$ is Cl, $R_4$ is H, $R_5$ is Cl and $R_6$ is 5-O-acetyl-β-D-ribofuranosyl (denoted compound 42a in the text);

$R_1$ is H, $R_2$ is Cl, $R_3$ is Cl, $R_4$ is H, $R_5$ is Br and $R_6$ is 5-O-acetyl-β-D-ribofuranosyl (denoted compound 52b in the text);

$R_1$ is H, $R_2$ is Cl, $R_3$ is Cl, $R_4$ is H, $R_5$ is Cl and $R_6$ is 2,3,5-tri-O-acetyl-β-D-ribofuranosyl (denoted compound 42 in the text);

$R_1$ is H, $R_2$ is Cl, $R_3$ is Cl, $R_4$ is H, $R_5$ is Br and $R_6$ is 2,3,5-tri-O-acetyl-β-D-ribofuranosyl (denoted compound 52a in the text);

and operative combinations thereof.

Thus compounds in the practice of the compositions and methods of the present invention include:

2,5,6-trichloro-1-(β-D-ribofuranosyl)benzimidazole where $R_1$, $R_4$=H; $R_2$, $R_3$, $R_5$=Cl; $R_6$=β-D-ribofuranosyl (denoted compound 45 in the text);

5,6-dichloro-2-bromo-1-(β-D-ribofuranosyl) benzimidazole where $R_1$, $R_4$=H; $R_2$, $R_3$=Cl; $R_5$=Br; $R_6$=β-D-ribofuranosyl (denoted compound 52 in the text);

2-chloro-5,6-dinitro-1-(β-D-ribofuranosyl)benzimidazole where $R_1$, $R_4$=H; $R_2$, $R_3$=$NO_2$; $R_5$=Cl; $R_6$=β-D-ribofuranosyl (denoted compound 61 in the text);

2,4,6-trichloro-1-(β-D-ribofuranosyl)benzimidazole where $R_2$, $R_4$=H; $R_1$, $R_3$, $R_5$=Cl; $R_6$=β-D-ribofuranosyl (denoted compound 81 in the text);

5,6-dichloro-2-iodo-1-(β-D-ribofuranosyl)benzimidazole where $R_1$, $R_4$=H; $R_2$, $R_3$=Cl; $R_5$=I; $R_6$=β-D-ribofuranosyl (denoted compound 83a in the text);

2-chloro-4,5-dibromo-1-(β-D-ribofuranosyl) benzimidazole where $R_3$, $R_4$=H; $R_1$, $R_2$=Br; $R_5$=Cl; $R_6$=β-D-ribofuranosyl (denoted compound 85 in the text);

5-bromo-2,6-dichloro-1-(β-D-ribofuranosyl) benzimidazole where $R_1$, $R_4$=H; $R_2$=Br; $R_3$, $R_5$=Cl; $R_6$=β-D-ribofuranosyl (denoted compound 95 in the text);

6-bromo-2,5-dichloro-1-(β-D-ribofuranosyl) benzimidazole where $R_1$, $R_4$=H; $R_2$, $R_5$=Cl; $R_3$=Br; $R_6$=β-D-ribofuranosyl (denoted compound 99 in the text);

2-chloro-5,6-diiodo-1-(β-D-ribofuranosyl)benzimidazole where $R_1$, $R_4$=H; $R_2$, $R_3$=I; $R_5$=Cl; $R_6$=β-D-ribofuranosyl (denoted compound 107 in the text); 2,5,6-trichloro-1-(2'-deoxy-β-D-erythro-pentofuranosyl)benzimidazole where $R_1$, $R_4$=H; $R_2$, $R_3$, $R_5$=Cl; $R_6$=2'-deoxy-β-D-erythro-pentofuranosyl (denoted compound 111 in the text);

5,6-dichloro-2-bromo-1-(2'-deoxy-β-D-erythro-pentofuranosyl)benzimidazole where $R_1$, $R_4$=H; $R_2$, $R_3$=Cl; $R_5$=Br; $R_6$=2'-deoxy-β-D-erythro-pentofuranosyl (denoted compound 112 in the text);

2-bromo-5,6-dichlorobenzimidazole where $R_1$, $R_4$, $R_6$=H; $R_2$, $R_3$=Cl; $R_5$=Br (denoted compound 7 in the text); 2,5(6)-dichloro-6(5)-fluorobenzimidazole where $R_1$, $R_4$, $R_6$=H; $R_2$, $R_5$=Cl; $R_3$=F (denoted compound 12c in the text);

2,4,5,6-tetrachlorobenzimidazole where $R_4$, $R_6$=H; $R_1$, $R_2$, $R_3$, $R_5$=Cl (denoted compound 13 in the text);

2-chloro-5-nitrobenzimidazole where $R_1$, $R_3$, $R_4$, $R_6$=H; $R_2$=$NO_2$; $R_5$=Cl (denoted compound 19 in the text);

2-chloro-5(6)-iodo-6(5)-nitrobenzimidazole where $R_1$, $R_4$, $R_6$=H; $R_2$=I; $R_3$=$NO_2$; $R_5$=Cl (denoted compound 26 in the text);

2,4,6-trichlorobenzimidazole where $R_2$, $R_4$, $R_6$=H; $R_1$, $R_3$, $R_5$=Cl (denoted compound 32 in the text);

2-chloro-5,6-diiodobenzimidizole where $R_1$, $R_4$, $R_6$=H; $R_2$, $R_3$=I, $R_5$=Cl (denoted compound 41 in the text);

2,4(7)-dichloro-6(5)-trifluoromethylbenzimidazole where $R_1$, $R_4$, $R_6$=H; $R_2$, $R_3$=I; $R_5$=Cl (denoted compound 41c in the text);

2-amino-5,6-dichloro-1-(β-D-ribofuranosyl) benzimidazole where $R_1$, $R_4$=H; $R_2$, $R_3$=Cl; $R_5$=$NH_2$; $R_6$=β-D-ribofuranosyl (denoted compound 44 in the text);

2-benzylthio-5,6-dichloro-1-(β-D-ribofuranosyl) benzimidazole where $R_1$, $R_4$=H; $R_2$, $R_3$=Cl; $R_5$=SCH$_2$C$_6$H$_5$; $R_6$=β-D-ribofuranosyl (denoted compound 54 in the text);

2-chloro-5,6-dibromo-1-(β-D-ribofuranosyl) benzimidazole where $R_1$, $R_4$=H; $R_2$, $R_3$=Br; $R_5$=Cl; $R_6$=β-D-ribofuranosyl (denoted compound 57 in the text);

2-chloro-5,6-difluoro-1-(β-D-ribofuranosyl) benzimidazole where $R_1$, $R_4$=H; $R_2$, $R_3$=F; $R_5$=Cl; $R_6$=β-D-ribofuranosyl (denoted compound 65 in the text);

2,5-dichloro-6-fluoro-1-β-D-ribofuranosylbenzimidazole (2,5) and 2,6-dichloro-5-fluoro-1-β-D-ribofuranosylbenzimidazole (2,6) where $R_1$, $R_4$=H; $R_2$, $R_5$=Cl; $R_3$=F; $R_6$=β-D-ribofuranosyl (denoted compound 65a in the text);

2,6-dichloro-1-(β-D-ribofuranosyl)benzimidazole where $R_1$, $R_2$, $R_4$=H; $R_3$, $R_5$=Cl; $R_6$=β-D-ribofuranosyl (denoted compound 67 in the text);

4,6-dichloro-2-trifluoromethyl-1-(β-D-ribofuranosyl) benzimidazole where $R_2$, $R_4$=H; $R_1$, $R_3$=Cl; $R_5$=CF$_3$; $R_6$=β-D-ribofuranosyl (denoted compound 81b in the text);

2,4-dichloro-1-(β-D-ribofuranosyl)-6-trifluoromethylbenzimidazole where $R_2$, $R_4$=H; $R_1$, $R_5$=Cl; $R_3$=CF$_3$; $R_6$=β-D-ribofuranosyl (denoted compound 81c in the text);

5-bromo-2-chloro-1-(β-D-ribofuranosyl)benzimidazole where $R_1$, $R_3$, $R_4$=H; $R_2$=Br; $R_5$=Cl; $R_6$=β-D-ribofuranosyl (denoted compound 87 in the text);

6-bromo-2-chloro-1-(β-D-ribofuranosyl)benzimidazole where $R_1$, $R_2$, $R_4$=H; $R_3$=Br; $R_5$=Cl, $R_6$=β-D-ribofuranosyl (denoted compound 90 in the text);

1-(β-D-ribofuranosyl)-2,4,5,6-tetrachlorobenzimidazole where $R_4$=H; $R_1$, $R_2$, $R_3$, $R_5$=Cl; $R_6$=β-D-ribofuranosyl (denoted compound 92 in the text);

2-chloro-1-(β-D-ribofuranosyl)-4,5,6-tribromobenzimidazoie where $R_4$=H; $R_1$, $R_2$, $R_3$=Br; $R_5$=Cl; $R_6$=β-D-ribofuranosyl (denoted compound 103 in the text);

2-amino-5,6-dichloro-1-(2'-deoxy-β-D-erythro-pentofuranosyl)benzimidazole where $R_1$, $R_4$=H; $R_2$, $R_3$=Cl; $R_5$=NH$_2$; $R_6$=2'-deoxy-β-D-erythro-pentofuranosyl (denoted compound 113 in the text);

2,5,6-trichloro-1-(β-D-arabinofuranosyl)benzimidazole where $R_1$, $R_4$=H; $R_2$, $R_3$, $R_5$=Cl; $R_6$=β-D-arabinofuranosyl (denoted compound 134 in the text);

2,4,5,6,7-pentachloro-1-[(1,3-dihydroxy-2-propoxy) methyl]benzimidazole where $R_1$, $R_2$, $R_3$, $R_4$, $R_5$=Cl; $R_6$=(1,3-dihydroxy-2-propoxy)methyl (denoted compound 155 in the text);

2-amino-4,5,6,7-tetrachloro-1-[(1,3-dihydroxy-2-propoxy)methyl]benzimidazole where $R_1$, $R_2$, $R_3$, $R_4$=Cl; $R_5$=NH$_2$; $R_6$=(1,3-dihydroxy-2-propoxy)methyl (denoted compound 156 in the text);

2,4,5,6,7-pentachloro-1-(2-hydroxyethoxymethyl) benzimidazole where $R_1$, $R_2$, $R_3$, $R_4$, $R_5$=Cl; $R_6$=2-hydroxyethoxymethyl) (denoted compound 166 in the text);

2-methoxy-4,5,6,7-tetrachloro-1-(2-hydroxyethoxymethyl)benzimidazole where $R_1$, $R_2$, $R_3$, $R_4$=Cl; $R_5$=OCH$_3$; $R_6$=2-hydroxyethoxymethyl (denoted compound 166a in the text);

2-amino-4,5,6,7-tetrachloro-1-(2-hydroxyethoxymethyl) benzimidazole where $R_1$, $R_2$, $R_3$, $R_4$=Cl; $R_5$=NH$_2$; $R_6$=2-hydroxyethoxymethyl (denoted compound 167 in the text);

2-amino-1-benzyl-5,6-dichlorobenzimidazole where $R_1$, $R_4$=H; $R_2$, $R_3$=Cl; $R_5$=NH$_2$; $R_6$=benzyl (denoted compound 182 in the text);

1-(5-O-acetyl-β-D-ribofuranosyl)-2,5,6-trichlorobenzimidazole where $R_1$, $R_4$=H; $R_2$, $R_3$, $R_5$=Cl; $R_6$=5-O-acetyl-β-D-ribofuranosyl (denoted compound 42a in the text);

1-(5-O-acetyl-β-D-ribofuranosyl)-2-bromo-5,6-dichlorobenzimidazole where $R_1$, $R_4$=H; $R_2$, $R_3$=Cl; $R_5$=Br; $R_6$=5-O-acetyl-β-D-ribofuranosyl (denoted compound 52b in the text);

2,5,6-trichloro-1-(2,3,5-tri-O-acetyl-β-D-ribofuranosyl) benzimtdazole where $R_1$, $R_4$=H; $R_2$, $R_3$, $R_5$=Cl; $R_6$=2,3,5-tri-O-acetyl-β-D-ribofuranosyl (denoted compound 42 in the text);

2-bromo-5,6-dichloro-1-(2,3,5-tri-O-acetyl-p62-D-ribofuranosyl)benzimidazole where $R_1$, $R_4$=H; $R_2$, $R_3$=Cl; $R_5$=Br; $R_6$=2,3,5-tri-O-acetyl-β-D-ribofuranosyl (denoted compound 52a in the text);

and operative combinations thereof.

Preferred compounds in the practice of the compositions and methods of the present invention include:

2,5,6-trichloro-1-(β-D-ribofuranosyl)benztmidazole where $R_1$, $R_4$=H; $R_2$, $R_3$, $R_5$=Cl; $R_6$=β-D-ribofuranosyl (denoted compound 45 in the text);

5,6-dichloro-2-bromo-1-(β-D-ribofuranosyl) benzimidazole where $R_1$, $R_4$=H; $R_2$, $R_3$=Cl; $R_5$=Br; $R_6$=β-D-ribofuranosyl (denoted compound 52 in the text);

2-chloro-5,6-dinitro-1-(β-D-ribofuranosyl)benzimidazole where $R_1$, $R_4$=H; $R_2$, $R_3$=NO$_2$; $R_5$=Cl; $R_6$=β-D-ribofuranosyl (denoted compound 61 in the text);

2,4,6-trichloro-1-(β-D-ribofuranosyl)benzimidazole where $R_2$, $R_4$=H; $R_1$, $R_3$, $R_5$=Cl; $R_6$=β-D-ribofuranosyl (denoted compound 81 in the text);

5,6-dichloro-2-iodo-1-(β-D-ribofuranosyl)benzimidazole where $R_1$, $R_4$=H; $R_2$, $R_3$=Cl; $R_5$=I; $R_6$=β-D-ribofuranosyl (denoted compound 83a in the text);

2-chloro-4,5-dibromo-1-(β-D-ribofuranosyl) benzimidazole where $R_3$, $R_4$=H; $R_1$, $R_2$=Br; $R_5$=Cl; $R_6$=β-D-ribofuranosyl (denoted compound 85 in the text);

5-bromo-2,6-dichloro-1-(β-D-ribofuranosyl) benzimidazole where $R_1$, $R_4$=H; $R_2$=Br; $R_3$, $R_5$=Cl; $R_6$=β-D-ribofuranosyl (denoted compound 95 in the text);

6-bromo-2,5-dichloro-1-(β-D-ribofuranosyl) benzimidazole where $R_1$, $R_4$=H; $R_2$, $R_5$=Cl; $R_3$=Br; $R_6$=β-D-ribofuranosyl (denoted compound 99 in the text);

2-chloro-5,6-diiodo-1-(β-D-ribofuranosyl)benzimidazole where $R_1$, $R_4$=H; $R_2$, $R_3$=I; $R_5$=Cl; $R_6$=β-D-ribofuranosyl (denoted compound 107 in the text);

2,5,6-trichloro-1-(2'-deoxy-β-D-erythro-pentofuranosyl) benzimidazole where $R_1$, $R_4$=H; $R_2$, $R_3$, $R_5$=Cl; $R_6$=2'-deoxy-β-D-erythro-pentofuranosyl (denoted Compound 111 in the text);

5,6-dichloro-2-bromo-1-(2'-deoxy-β-D-erythro-pentofuranosyl)benzimidazole where $R_1$, $R_4$=H; $R_2$, $R_3$=Cl; $R_5$=Br; $R_6$=2'-deoxy-β-D-erythro-pentofuranosyl (denoted compound 112 in the text);

2-bromo-5,6-dichlorobenzimidazole where $R_1$, $R_4$, $R_6$=H; $R_2$, $R_3$=Cl; $R_5$=Br (denoted compound 7 in the text);

2-chloro-5-nitrobenzimidazole where $R_1$, $R_3$, $R_4$, $R_6$=H; $R_2$=NO$_2$; $R_5$=Cl (denoted compound 19 in the text);

2-chloro-5(6)-iodo-6(5)-nitrobenzimidazole where $R_1$, $R_4$, $R_5$=H; $R_2$=I; $R_3$=NO$_2$; $R_5$=Cl (denoted compound 26 in the text);

2,4,6-trichlorobenzimidazole where $R_2$, $R_4$, $R_6$=H; $R_1$, $R_3$, $R_5$=Cl (denoted compound 32 in the text);

2-benzylthio-5,6-dichloro-1-(β-D-ribofuranosyl) benzimidazole where $R_1$, $R_4$=H; $R_2$, $R_3$=Cl; $R_5$=SCH$_2$C$_6$H$_5$; $R_6$=β-D-ribofuranosyl (denoted compound 54 in the text);

2-chloro-5,6-dibromo-1-(β-D-ribofuranosyl) benzimidazole where $R_1$, $R_4$=H; $R_2$, $R_3$=Br; $R_5$=Cl; $R_6$=β-D-ribofuranosyl (denoted compound 57 in the text);

2-chloro-5,6-difluoro-1-(β-D-ribofuranosyl) benzimidazole where $R_1$, $R_4$=H; $R_2$, $R_3$, =F; $R_5$=Cl; $R_6$=β-D-ribofuranosyl (denoted compound 65 in the text);

2,5-dichloro-6-fluoro-1-β-D-ribofuranosylbenzimidazole (2,5) and 2,6-dichloro-5-fluoro-1-(β-D-ribofuranosylbenzimidazole (2,6) where $R_1$, $R_4$=H; $R_2$, $R_5$=Cl; $R_3$=F; $R_6$=β-D-ribofuranosyl (denoted compound 65a in the text);

2,6-dichloro-1-(β-D-ribofuranosyl)benzimidazole where $R_1$, $R_2$, $R_4$=H; $R_3$, $R_5$=Cl; $R_6$=β-D-ribofuranosyl (denoted compound 67 in the text);

4,6-dichloro-2-trifluoromethyl-1-(β-D-ribofuranosyl)benzimidazole where $R_2$, $R_4$=H; $R_1$, $R_3$=Cl; $R_5$=CF$_3$; $R_6$=β-D-ribofuranosyl (denoted compound 81b in the text);

2,4-dichloro-1-(β-D-ribofuranosyl)-6-trifluoromethylbenzimidazole where $R_2$, $R_4$=H; $R_1$, $R_5$=Cl; $R_3$=CF$_3$; $R_6$=β-D-ribofuranosyl (denoted compound 81c in the text);

5-bromo-2-chloro-1-(β-D-ribofuranosyl)benzimidazole where $R_1$, $R_3$, $R_4$=H; $R_2$=Br; $R_5$=Cl; $R_6$=β-D-ribofuranosyl (denoted compound 87 in the text);

6-bromo-2-chloro-1-(β-D-ribofuranosyl)benzimidazole where $R_1$, $R_2$, $R_4$=H; $R_3$=Br; $R_5$=Cl, $R_6$=β-D-ribofuranosyl (denoted compound 90 in the text);

1-(β-D-ribofuranosyl)-2,4,5,6-tetrachlorobenzimidazole where $R_4$=H; $R_1$, $R_2$, $R_3$, $R_5$=Cl; $R_6$=β-D-ribofuranosyl (denoted compound 92 in the text);

2-chloro-1-(β-D-ribofuranosyl)-4,5,6-tribromobenzimidazole where $R_4$=H; $R_1$, $R_2$, $R_3$=Br; $R_5$=Cl; $R_6$=β-D-ribofuranosyl (denoted compound 103 in the text);

2-amino-5,6-dichloro-1-(2'-deoxy-β-D-erythro-pentofuranosyl)benzimidazole where $R_1$, $R_4$=H; $R_2$, $R_3$=Cl; $R_5$=NH$_2$; $R_6$=2'-deoxy-β-D-erythro-pentofuranosyl (denoted in the text);

2,5,6-trichloro-1-(1,3-D-arabinofuranosyl)benzimidazole where $R_1$, $R_4$=H; $R_2$, $R_3$, $R_5$=Cl; $R_6$=β-D-arabinofuranosyl (denoted compound 134 in the text);

2,4,5,6,7-pentachloro-1-[(1,3-dihydroxy-2-propoxy)methyl]benzimidazole where $R_1$, $R_2$, $R_3$, $R_4$, $R_5$=Cl; $R_6$=(1,3-dihydroxy-2-propoxy)methyl (denoted compound 155 in the text);

2-amino-4,5,6,7-tetrachloro-1-[(1,3-dihydroxy-2-propoxy)methyl]benzimidazole where $R_1$, $R_2$, $R_3$, $R_4$=Cl; $R_5$=NH$_2$; $R_6$=(1,3-dihydroxy-2-propoxy)methyl (denoted compound 156 in the text);

2-methoxy-4,5,6,7-tetrachloro-1-(2-hydroxyethoxymethyl)benzimidazole where $R_1$, $R_2$, $R_3$, $R_4$=Cl; $R_5$=OCH$_3$; $R_6$=2-hydroxyethoxymethyl (denoted compound 166a in the text);

2-amino-4,5,6,7-tetrachloro-1-(2-hydroxyethoxymethyl)benzimidazole where $R_1$, $R_2$, $R_3$, $R_4$=Cl; $R_5$=NH$_2$; $R_6$=2-hydroxyethoxymethyl (denoted compound 167 in the text);

2-amino-1-benzyl-5,6-dichlorobenzimidazole where $R_1$, $R_4$=H; $R_2$, $R_3$=Cl; $R_5$=NH$_2$; $R_6$=benzyl (denoted compound 182 in the text);

1-(5-O-acetyl-β-D-ribofuranosyl)-2,5,6-trichlorobenzimidazole where $R_1$, $R_4$=H; $R_2$, $R_3$, $R_5$=Cl; $R_6$=5-O-acetyl-β-D-ribofuranosyl (denoted compound 42a in the text);

1-(5-O-acetyl-β-D-ribofuranosyl)-2-bromo-5,6-dichlorobenzimidazole where $R_1$, $R_4$=H; $R_2$, $R_3$=Cl; $R_5$=Br; $R_6$=5-O-acetyl-β-D-ribofuranosyl (denoted compound 52b in the text);

2,5,6-trichloro-1-(2,3,5-tri-O-acetyl-β-D-ribofuranosyl)benzimidazole where $R_1$, $R_4$=H; $R_2$, $R_3$, $R_5$=Cl; $R_6$=2,3,5-tri-O-acetyl-β-D-ribofuranosyl (denoted compound 42 in the text);

2-bromo-5,6-dichloro-1-(2,3,5-tri-O-acetyl-β-D-ribofuranosyl)benzimidazole where $R_1$, $R_4$=H; $R_2$, $R_3$=Cl; $R_5$=Br; $R_6$=2,3,5-tri-O-acetyl-β-D-ribofuranosyl (denoted compound 52a in the text);

and operative combinations thereof.

More preferred compounds in the practice of the compositions and methods of the present invention include:

2,5,6-trichloro-1-(β-D-ribofuranosyl)benzimidazole where $R_1$, $R_4$=H; $R_2$, $R_3$, $R_5$=Cl; $R_6$=β-D-ribofuranosyl (denoted compound 45 in the text);

5,6-dichloro-2-bromo-1-(β-D-ribofuranosyl)benzimidazole where $R_1$,$R_4$=H; $R_2$, $R_3$=Cl; $R_5$=Br; $R_6$=β-D-ribofuranosyl (denoted compound 52 in the text);

2-chloro-4,5-dibromo-1-(β-D-ribofuranosyl)benzimidazole where $R_3$, $R_4$=H; $R_1$, $R_2$=Br; $R_5$=Cl; $R_6$=β-D-ribofuranosyl (denoted compound 85 in the text);

2,5,6-trichloro-1-(2'-deoxy-β-D-erythro-pentofuranosyl)benzimidazole where $R_1$, $R_4$=H; $R_2$, $R_3$, $R_5$=Cl; $R_6$=2'-deoxy-β-D-erythro-pentofuranosyl (denoted compound 111 in the text);

2-benzylthio-5,6-dichloro-1-(β-D-ribofuranosyl)benzimidazole where $R_1$, $R_4$=H; $R_2$, $R_3$=Cl; $R_5$=SCH$_2$C$_6$H$_5$; $R_6$=β-D-ribofuranosyl (denoted compound 54 in the text);

2-chloro-5,6-difluoro-1-(β-D-ribofuranosyl)benzimidazole where $R_1$, $R_4$=H; $R_2$, $R_3$=F; $R_5$=Cl; $R_6$-β-D-ribofuranosyl (denoted compound 65 in the text);

2,5-dichloro-6-fluoro-1-β-D-ribofuranosylbenzimidazole (2,5) and 2,6-dichloro-5-fluoro-1-β-D-ribofuranosylbenzimidazole (2,6) where $R_1$, $R_4$=H; $R_2$, $R_5$=Cl; $R_3$=F; $R_6$=β-D-ribofuranosyl (denoted compound 65a in the text);

2,4-dichloro-1-(β-D-ribofuranosyl)-6-trifluoromethylbenzimidazole where $R_2$, $R_4$=H; $R_1$, $R_5$=Cl; $R_3$=CF$_3$; $R_6$=β-D-ribofuranosyl (denoted compound 81c in the text);

5-bromo-2-chloro-1-(β-D-ribofuranosyl)benzimidazole where $R_1$, $R_3$, $R_4$=H; $R_2$=Br; $R_5$=Cl; $R_6$=β-D-ribofuranosyl (denoted compound 87 in the text);

5-bromo-2-chloro-1-(β-D-ribofuranosyl)benzimidazole where $R_1$, $R_2$, $R_4$=H; $R_3$=Br; $R_5$=Cl; $R_6$=β-D-ribofuranosyl (denoted compound 90 in the text);

1-(β-D-ribofuranosyl)-2,4,5,6-tetrachlorobenzimidazole where $R_4$=H; $R_1$, $P_2$, $R_3$, $R_5$=Cl; $R_6$=β-D-ribofuranosyl (denoted compound 92 in the text);

2-amino-4,5,6,7-tetrachloro-1-[(1,3-dihydroxy-2-propoxy)methyl]benzimidazole where $R_1$, $R_2$, $R_3$, $R_4$=Cl; $R_5$=NH$_2$; $R_6$=(1,3-dihydroxy-2-propoxy)methyl (denoted compound 156 in the text);

2-amino-1-benzyl-5,6-dichlorobenzimidazole where $R_1$, $R_4$=H; $R_2$, $R_3$=Cl; $R_5$=NH$_2$; $R_6$=benzyl (denoted compound 182 in the text);

and operative combinations thereof.

The present invention also comprises novel polysubstituted benzimidazoles, and, as later described, their synthesis and use in medicaments and methods of treatment. Novel polysubstituted benzimidazoles of the present invention include compounds 52, 61, 83a, 85, 95, 99, 107, 111, 112, 7, 12c, 13, 19, 26, 32, 41, 41c, 57, 65, 65a, 67, 81b, 81c, 87, 90, 92, 103, 113, 134, 182, 42a, 52b, 42, 52a, 81, 155, 156, 166, 166a, 167 of the above-described group. The structures of compounds 81, 155, 156, 166, 166a, and 167 were depicted in Abstracts submitted to the April 1990 meeting of the American Chemical Society in Boston, Mass. The structures of compounds 45, 44 and 54 were also previously proposed in Townsend et al., Chore. Reviews 70:389 (1970) and Smith et al, Cancer Treat. Rep. 60:1567–1584 (1976), but without a description of synthesis and without recognition of any antiviral activity or therapeutic value as antiviral agents. Preferred novel compounds of the present invention include compounds 52, 85, 111, 65, 65a, 81 c, 87, 90, 92 and 182.

B. Pharmaceutical Compositions and Administration

The polysubstituted benzimidazoles used in the practice of the present invention all exhibit antiviral activity, many with acceptable cytotoxicity. it will be appreciated that compounds of the present invention which exhibit relatively high antiviral activity versus cytotoxicity, i.e. good selectivity, are preferred. It will also be appreciated that antiviral treatment in accordance with the present invention encompasses the treatment of viral infections, as well as prophylactic treatment which may be desired in certain situations, e.g. in immuno-compromised patients, such as bone marrow transplant patients.

The polysubstituted benzimidazoles of the invention have been demonstrated as particularly effective against viruses of the herpes family. They are thus useful in treatment against human cytomegalovirus (HCMV) and herpes simplex viruses types 1 and 2. Other viruses contemplated to be treated within the scope of the present invention include, but are not limited to: varicella-zoster virus (vadcella; zoster, .chickenpox; shingles); Epstein-Barr virus (infectious mononucleosis; glandular fever; and Burkittis lymphoma); $HHV_6$; human immunodeficiency virus (HIV) and hepatitis viruses.

The compounds and compositions of the present invention can be used in the manufacture of medicaments and in antiviral treatment of humans and other animals by administration in accordance with conventional procedures, such as an active ingredient in pharmaceutical compositions. The compounds of the invention can be provided as pharmaceutically acceptable formulations and/or "prodrugs," including but not limited to esters, especially carboxylic acid esters (perferably $C_1$ to $C_{20}$), such as 5'- acetyl and 2',3',5'-triacetyl prodrugs (e.g. compounds 42a, 52b, 42 and 52a) and pharmaceutical salts such as thiolate, citrate and acetate salts.

The pharmaceutical compositions can be administeredtopically, orally, or parentally and may take the form of tablets, lozenges, granules, capsules, pills, ampoules or suppositories. They may also take the form of ointments, gels, pastes, creams, sprays, lotions, suspensions, solutions and emulsions of the active ingredient in aqueous or non-aqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, buccal and sublingual), vaginal, parental (including subcutaneous, intramuscular, intravenous and intradermal) and pulmonary. It will also be appreciated that the preferred route will vary with the condition and age of the recipient and the nature of the infection.

In general, a suitable dose for each of the above-named viral infections, e.g., CMV, EBV, and HHV6 infections, is in the range of about 0;1 to about 250 mg per kilogram body weight of the recipient per day, preferably in the range of about 1 to about 100 mg per kilogram body weight per day and most preferably in the range of about 5 to about 20 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses amy be administered in unit dosage forms, for example, containing about 10 to about 1000 mg, preferably about 20 to about 500 mg, and most preferably about 100 to about 400 mg of active ingredient per unit dosage form. It will be appreciated that appropriate dosages of the compounds and compositions of the invention may depend on the type and severity of the viral infection and can vary from patient to patient. Determining the optimal dosage will generally involve the balancing of the level of therapeutic benefit against any risk or deleterious side effects of the antiviral treatments of the present invention.

Ideally, the active ingredient should be administered to achieve peak plasma concentrations of the active compound of from about 0.25 to about 100 µM, preferably about 0.5 to about 70 µM, most preferably about 1 to about 50 µM. This may be achieved, for example, by the intravenous injection of about 0.1 to about 5% solution of the active ingredient, optionally in saline, or orally administered, for example, as a tablet, capsule or syrup containing about 0.1 to about 250 mg per kilogram of the active ingredient. Desirable blood levels may be maintained by a continuous infusion to provide about 0.01 to about 5.0 mg/kg/hour or by intermittent infusions containing about 0.4 to about 15 mg per kilogram of the active ingredient.

While it is possible forthe active ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product. Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylemthyl cellulose), lubricant, inert diluent, preservative, disintegrant (e.g., sodium starch glycollate, cross-linked povidone, cross-linked sodium carboxmethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For infections of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the active ingredient may be employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxlde and related analoguas.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topicel administration to the eye also include eye drops wherein the active ingredient is dissolved or suspended in a suitable carrier, especially an aqueous solvent for the active ingredient. The active ingredient is preferably present in such formulation in a concentration of about 0.5 to about 20%, advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented es pessaries, tampens, creams, gels, pastes, foams or spray formulations containing, in addition to the active ingredient, such carriers as are known in the art to be appropriate.

Formulations suitable for nasal administration, wherein the carrier is a solid, include a coarse powder having a particle size, for example, in fie range of about 20 to about 500 microns which is administered in the manner in which snuff is taken, i.e., by rapid inhalation through the nasal passage from a container of the powder held close up to the nose. Suitable formulations wherein the carrier is a liquid for administration as for example, a nasal spray or a nasal drops, include aqueous or oily solutions of the active ingredient.

Formulations suitable for parenteral administration include aqueous and non- aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other micorparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared frgm sterile powders, granules and tablets of the kind previously described.

Preferred unit dosage formulations are those containing a daily dose or unit, daily subdose, as herein above-recited, or an appropriate fraction thereof, of an active ingredient.

It should be understood that in addition to the ingredients particularly mentioned above, the formulations of this invention my include other agents conventional in the art having regard to the type of formulation in question, for example, those suitable of oral administration my include such further agents as sweeteners, thickeners and flavoring agents.

Compounds of the formula of the present invention may also be presented for the use in the form of veterinary formulations, which may be prepared, for example, by methods that are conventional in the art.

C. Methods of Synthesis

The present invention also comprises methods of synthesis of polysubstituted benzimidazoles of the invention. The present invention provides a process for the preparation of polysubstituted benzimidazoles of the following formula:

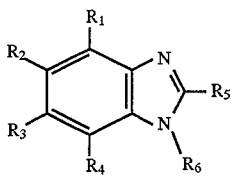
(I)

wherein $R_1$ is H, $R_2$ is Cl, $R_3$ is Cl, $R_4$ is H, $R_5$ is Cl and $R_6$ is β-D-ribofuranosyl (denoted compound 45 in the text);

$R_1$ is H, $R_2$ is Cl, $R_3$ is Cl, $R_4$ is H, $R_5$ is Br and $R_6$ is β-D-ribofuranosyl (denoted compound 52 in the text);

$R_1$ is H, $R_2$ is $NO_2$, $R_3$ is $NO_2$, $R_4$ is H, $R_5$ is Cl and $R_6$ is β-D-ribofuranosyl (denoted compound 61 in the text);

$R_1$ is Cl, $R_2$ is H, $R_3$ is Cl, $R_4$ is H, $R_5$ is Cl and $R_6$ is β-D-ribofuranosyl (denoted compound 81 in the text);

$R_1$ is H, $R_2$ is Cl, $R_3$ is Cl, $R_4$ is H, $R_5$ is I and $R_6$ is β-D-ribofuranosyl (denoted compound 83a in the text);

$R_1$ is Br, $R_2$ is Br, $R_3$ is H, $R_4$ is H, $R_5$ is Cl and $R_6$ is β-D-ribofuranosyl (denoted compound 85 in the text);

$R_1$ is H, $R_2$ is Br, $R_3$ is Cl, $R_4$ is H, $R_5$ is Cl and $R_6$ is β-D-ribofuranosyl (denoted compound 95 in the text);

$R_1$ is H, $R_2$ is Cl, $R_3$ is Br, $R_4$ is H, $R_5$ is Cl and $R_6$ is β-D-ribofuranosyl (denoted compound 99 in the text);

$R_1$ is H, $R_2$ is I, $R_3$ is I, $R_4$ is H, $R_5$ is Cl and $R_6$ is β-D-ribofuranosyl (denoted compound 107 in the text);

$R_1$ is H, $R_2$ is Cl, $R_3$ is Cl, $R_4$ is H, $R_5$ is Cl and $R_6$ is 2'-deoxy-β-D-erythro-pentofuranosyl (denoted compound 111 in the text);

$R_1$ is H, $R_2$ is Cl, $R_3$ is Cl, $R_4$ is H, $R_5$ is Br and $R_6$ is 2'-deoxy-β-D-erythro-pentofuranosyl (denoted compound 112 in the text);

$R_1$ is H; $R_2$ is Cl, $R_3$ is Cl, $R_4$ is H, $R_5$ is Br and $R_6$ is H (denoted compound 7 in the text);

$R_1$ is H, $R_2$ is Cl, $R_3$ is F, $R_4$ is H, $R_5$ is Cl and $R_6$ is H (denoted compound 12c in the text);

$R_1$ is Cl, $R_2$ is Cl, $R_3$ is Cl, $R_4$ is H, $R_5$ is Cl and $R_s$ is H (denoted compound 13 in the text);

$R_1$ is H, $R_2$ is $NO_2$, $R_3$ is H, $R_4$ is H, $R_5$ is Cl and $R_6$ is H (denoted compound 19 in the text);

$R_1$ is H, $R_2$ is I, $R_3$ is $NO_2$, $R_4$ is H, $R_5$ is Cl and $R_6$ is H (denoted compound 26 in the text);

$R_1$ is Cl, $R_2$ is H, $R_3$ is Cl, $R_4$ is H, $R_5$ is Cl and $R_6$ is H (denoted compound 32 in the text);

$R_1$ is H, $R_2$ is I, $R_3$ is I, $R_4$ is H, $R_5$ is Cl and $R_6$ is H (denoted compound 41 in the text);

$R_1$ is Cl, $R_2$ is H, $R_3$ is $CF_3$, $R_4$ is H, $R_5$ is Cl and $R_6$ is H (denoted compound 41c in the text);

$R_1$ is H, $R_2$ is Cl, $R_3$ is Cl, $R_4$ is H, $R_5$ is $NH_2$ and $R_6$ is β-D-ribofuranosyl (denoted compound 44 in the text);

$R_1$ is H, $R_2$ is Cl, $R_3$ is Cl, $R_4$ is H, $R_5$ is $SCH_2 C_6 H_5$ and $R_6$ is β-D-ribofuranosyl (denoted compound 54 in the text);

$R_1$ is H, $R_2$ is Br, $R_3$ is Br, $R_4$ is H, $R_5$ is Cl and $R_6$ is β-D-ribofuranosyl (denoted compound 57 in the text);

$R_1$ is H, $R_2$ is F, $R_3$ is F, $R_4$ is H, $R_5$ is Cl and $R_6$ is β-D-ribofuranosyl (denoted compound 65 in the text);

$R_1$ is H, $R_2$ is Cl, $R_3$ is F, $R_4$ is H, $R_5$ is Cl and $R_6$ is β-D-ribofuranosyl (denoted compound 65a in the text);

$R_1$ is H, $R_2$ is H, $R_3$ is Cl, $R_4$ is H, $R_5$ is Cl and $R_6$ is β-D-ribofuranosyl (denoted compound 67 in the text);

$R_1$ is Cl, $R_2$ is H, $R_3$ is Cl, $R_4$ is H, $R_5$ is $CF_3$ and $R_6$ is β-D-ribofuranosyl (denoted compound 81b in the text);

$R_1$ is Cl, $R_2$ is H, $R_3$ is $CF_3$, $R_4$ is H, $R_5$ is Cl and $R_6$ is β-D-ribofuranosyl (denoted compound 81c in the text);

$R_1$ is H, $R_2$ is Br, $R_3$ is H, $R_4$ is H, $R_5$ is Cl and $R_6$ is β-D-ribofuranosyl (denoted compound 87 in the text);

$R_1$ is H, $R_2$ is H, $R_3$ is Br, $R_4$ is H, $R_5$ is Cl and $R_6$ is β-D-ribofuranosyl (denoted compound 90 in the text);

$R_1$ is Cl, $R_2$ is Cl, $R_3$ is Cl, $R_4$ is H, $R_5$ is Cl and $R_6$ is β-D-ribofuranosyl (denoted compound 92 in the text);

$R_1$ is Br, $R_2$ is Br, $R_3$ is Br, $R_4$ is H, $R_5$ is Cl and $R_6$ is β-D-ribofuranosyl (denoted compound 103 in the text);

$R_1$ is H, $R_2$ is Cl, $R_3$ is Cl, $R_4$ is H, $R_5$ is $NH_2$ and $R_6$ is 2'-deoxy-β-D-erythro-pentofuranosyl (denoted compound 113 in the text);

$R_1$ is H, $R_2$ is Cl, $R_3$ is Cl, $R_4$ is H, $R_5$ is Cl and $R_6$ is β-D-arabinofuranosyl (denoted compound 134 in the text);

$R_1$ is Cl, $R_2$ is Cl, $R_3$ is Cl, $R_4$ is Cl, $R_5$ is Cl and $R_6$ is (1,3-dihydroxy-2-propoxy)methyl (denoted compound 155 in the text);

$R_1$ is Cl, $R_2$ is Cl, $R_3$ is Cl, $R_4$ is Cl, $R_5$ is $NH_2$ and $R_6$ is (1,3-dihydroxy-2-propoxy)methyl (denoted compound 156 in the text);

$R_1$ is Cl, $R_2$ is Cl, $R_3$ is Cl, $R_4$ is Cl, $R_5$ is Cl and $R_6$ is 2-hydroxyethoxymethyl (denoted compound 166 in the text);

$R_1$ is Cl, $R_2$ is Cl, $R_3$ is Cl, $R_4$ is Cl, $R_5$ is $OCH_3$ and $R_6$ is 2-hydroxyethoxymethyl (denoted compound 166a in the text);

$R_1$ is Cl, $R_2$ is Cl, $R_3$ is Cl, $R_4$ is Cl, $R_5$ is $NH_2$ and $R_6$ is 2-hydroxyethoxymethyl (denoted compound 167 in the text);

$R_1$ is H, $R_2$ is Cl, $R_3$ is Cl, $R_4$ is H, $R_5$ is Cl and $R_6$ is 5-O-acetyl-β-D-ribofuranosyl (denoted compound 42a in the text);

$R_1$ is H, $R_2$ is Cl, $R_3$ is Cl, $R_4$ is H, $R_5$ is Br and $R_6$ is 5-O-acetyl-β-D-ribofuranosyl (denoted compound 52b in the text);

$R_1$ is H, $R_2$ is Cl, $R_3$ is Cl, $R_4$ is H, $R_5$ is Cl and $R_6$ is 2,3,5-tri-O-acetyl-β-D-ribofuranosyl (denoted compound 42 in the text);

$R_1$ is H, $R_2$ is Cl, $R_3$ is Cl, $R_4$ is H, $R_5$ is Br and $R_s$ is 2,3,5-tri-O-acetyl-β-D-ribofuranosyl (denoted compound 52a in the text);

which comprises reacting a compound of the following formula:

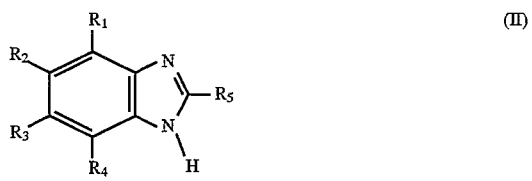
(II)

wherein $R_1$, $R_2$, $R_3$, $R_4$ and $R_5$ are defined as above, with a protected compound of formula $R_6^a X$, shown below, in which $R_6^a$ represents a protected carbohydrate or carbohydrate-like moiety and X represents a leaving group, and subsequently removing the protecting group from the moiety to form the desired compound.

The compound of formula $R_6^a X$ is represented by the formula:

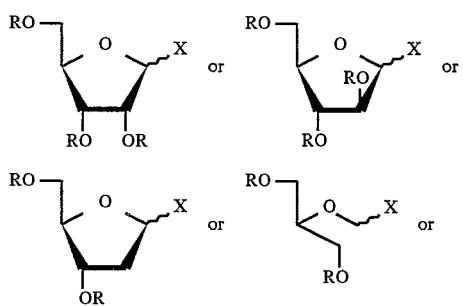

-continued

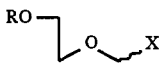

wherein X represents a leaving group such as a halo (e.g. chloro) or $C_{1-4}$ alkanoyloxy (e.g. acetoxy) group and R represents a hydroxy protecting group, for example, an acyl group such as $C_{1-4}$ alkanoyl (e.g. acetyl or aroyl, e.g. benzoyl, e.g. p-nitrobenzoyl and the like.

The reaction of the compound of formula II with the compound of formula $R_6{}^aX$ may be effected in the presence of BSA, TMSOTf, BSTFA and the like, advantageously in a solvent such as acetonitrile, dichloroethane and the like.

The removal of the protecting groups in the above process according to the invention may be effected, for example, by treatment with methanolic ammonia, boron trihalide, sodium carbonate, potassium cyanide and the like.

Additionally, compounds of formula II may be reacted with compounds of the formula:

wherein R'=aralkyl
to prepare a compound of general formula I, wherein $R_6$ is benzyl rather than a carbohydrate or carbohydrate-like moiety, and wherein, e.g. $R_1$ is H, $R_2$, $R_3$ is Cl, $R_4$ is H and $R_5$ is $NH_2$ or Cl.

Figure 2:
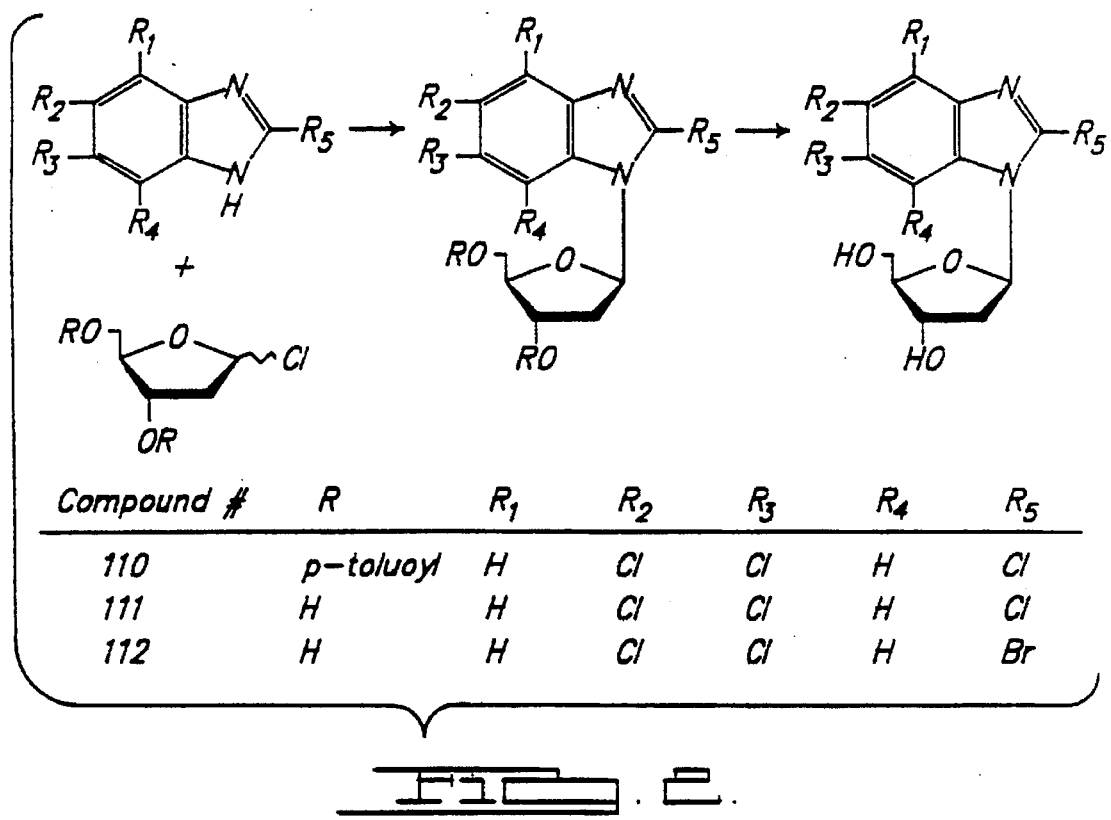
Figure 2A:
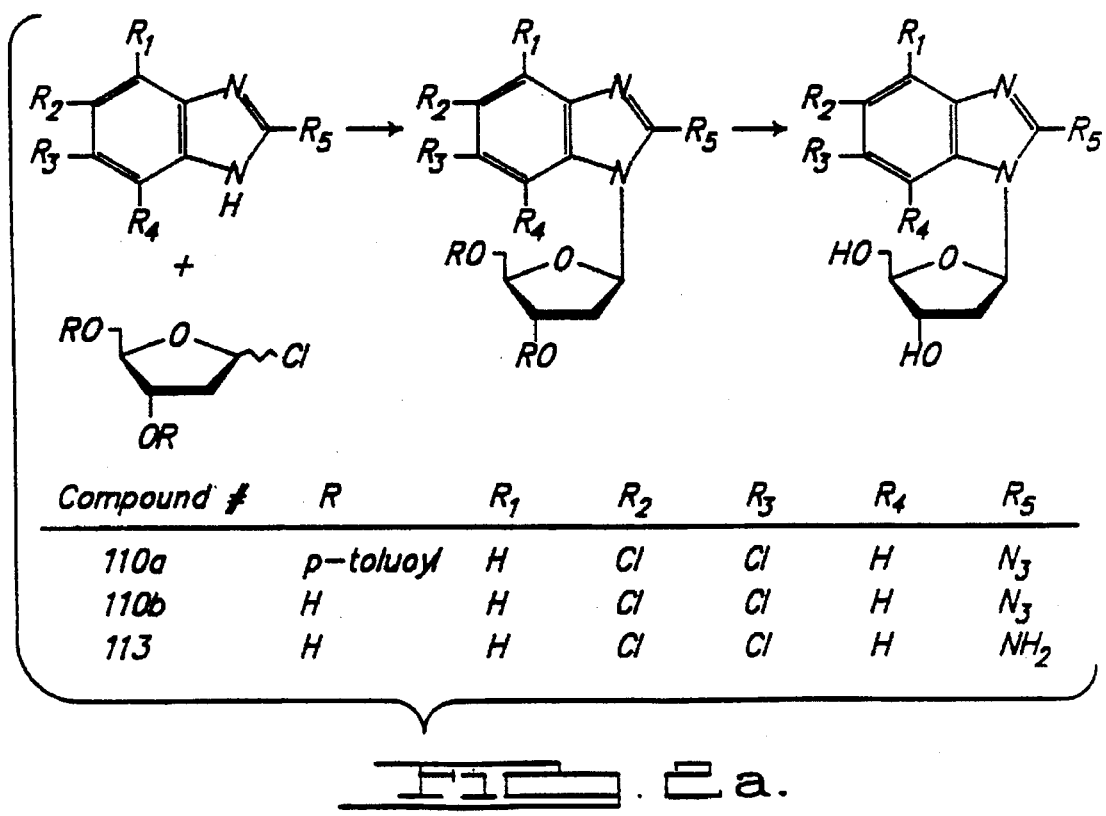
Figure 2B:
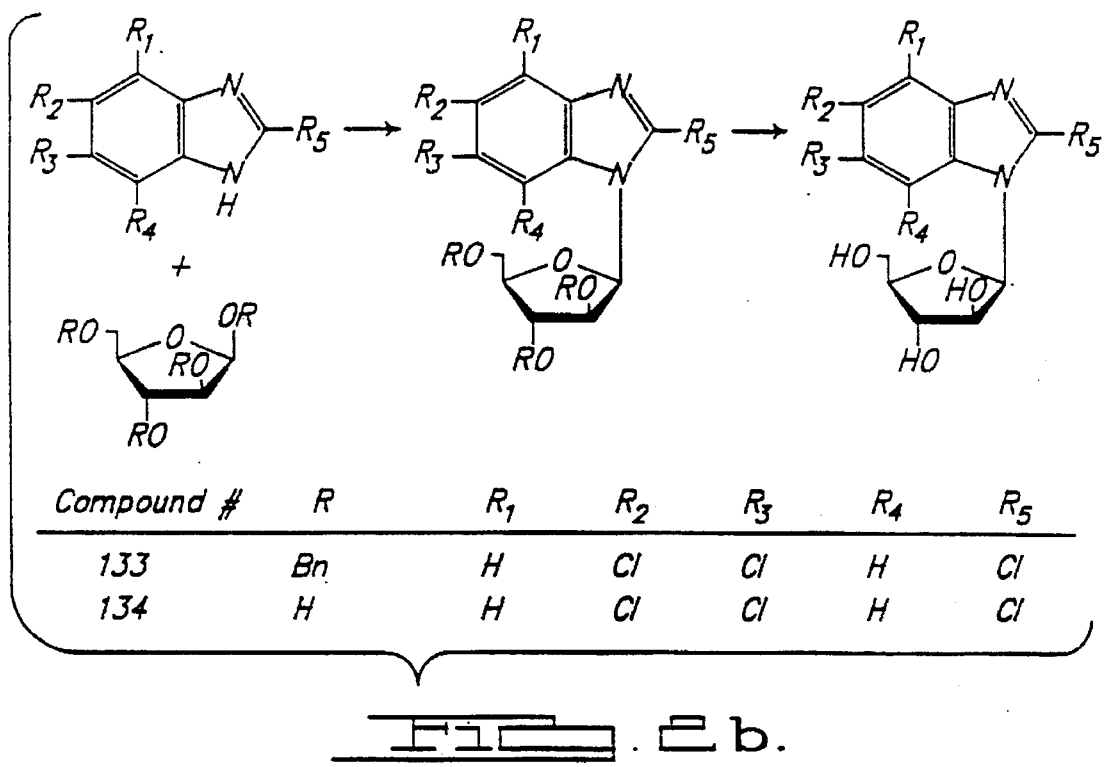
Figure 2C:
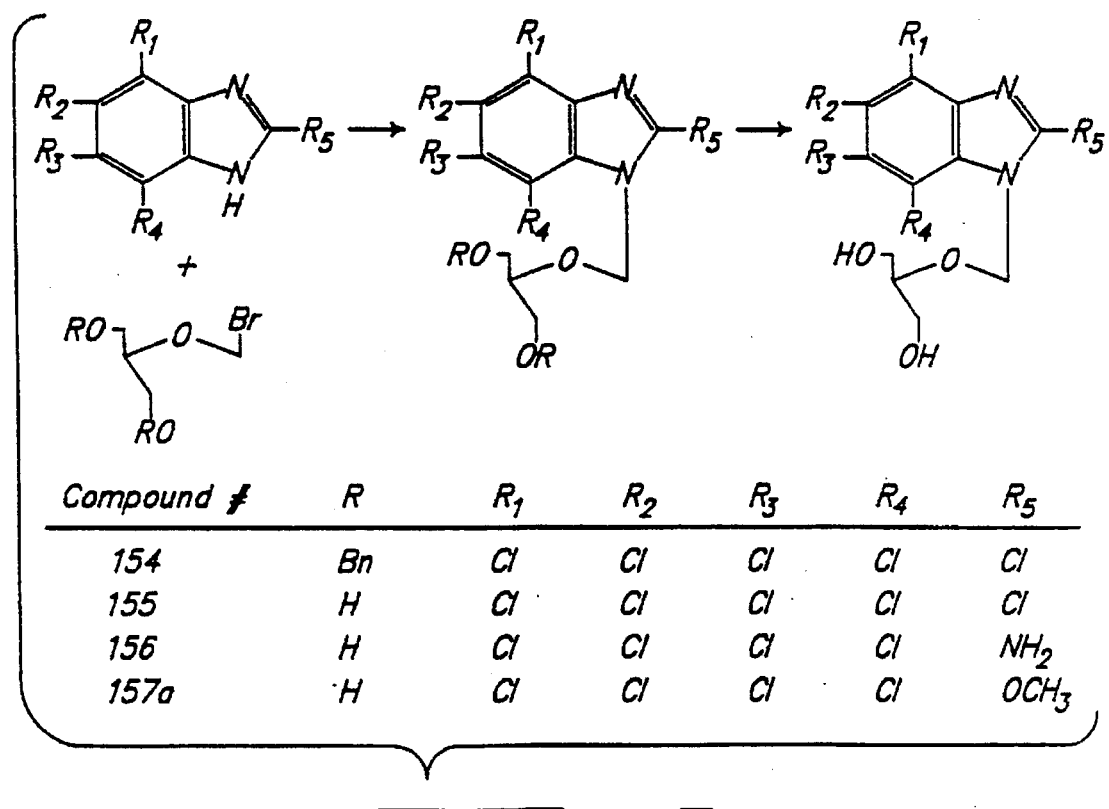
Figure 2D:
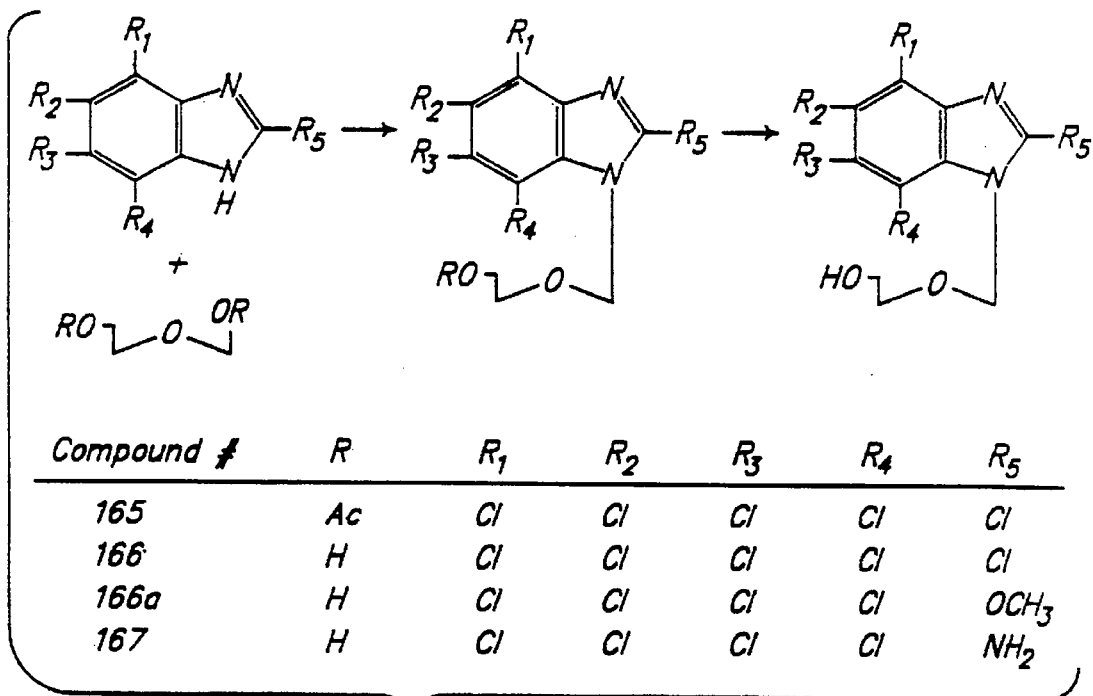
Figure 2D:
Figure 2E:
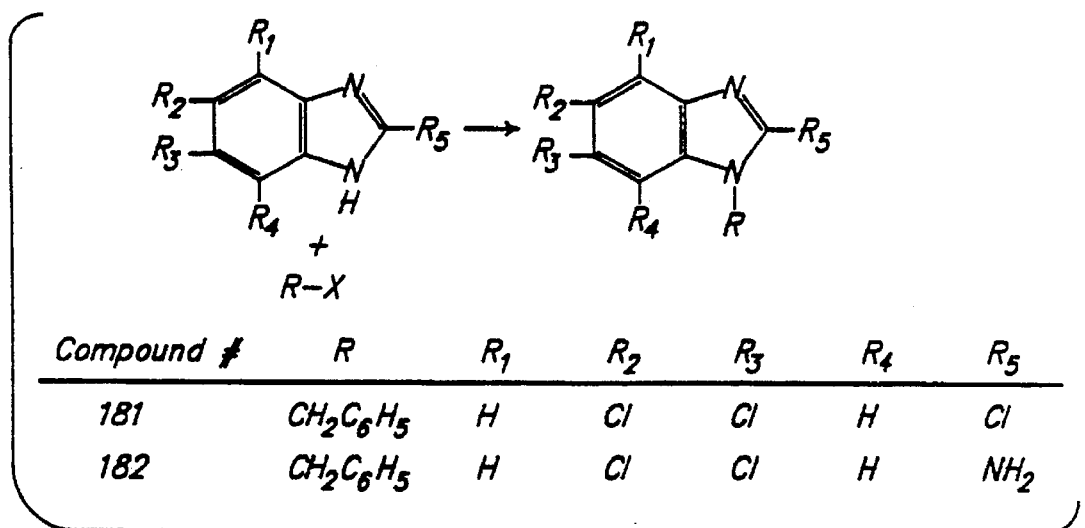
Figure 2E:
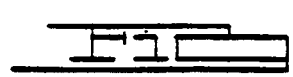

The compounds of the present invention, can be synthesized in accordance with the representative procedures dascdbed vide infra. In general, the appropriate benzimidazole was prepared and then condensed with the appropriate precursor for the ultimate $R_6$ group as represented by the schemes aRd substituent charts of FIGS. 1 and 2. This furnished polysubstituted banzimidazoles which had potential antiviral activity, and were also amenable toward subsequent chemical transformations to afford additional compounds. The solvents, reagents and reaction conditions for the preparation of some representative starting materials, intermediate and target compounds are presented in detail below. The compound numbering in this section and specification refers to the reaction scherhe and chartnumbers of the compounds.

SPECIFIC EXAMPLES 2, 5, 6-Trichlorobenzimidazole(5)

Method A(5)

A solution of 5,6-dichlorobenzimidazole-2-one (5 g, 2.5 mmole) in 75ml of $POCl_3$ was heated at reflux for 5 hr. HCl gas was passed into the mixture for the last ½ hr. Excess $POCl_3$ was removed in vacuo and the residue was decomposed with HCl (150 ml). The brown solid was removed by filtration and washed with $H_2O$ (100 ml). The filtrate was made slowly basic With $NH_4OH$. After cooling, the precipitate was filtered, the precipitate was dissolved in MeOH and an insoluble material was removed by filtration. The filtrate was evaporated under diminished pressure to dryness. The residue was applied to a column of silica gel (Kiesel Gel 70-230 mesh) and eluted with $CH_2Cl_2$. The fractions containing the product (5) were combined, and evaporated to dryness. Yield 1.36 g (25.0%).

Method B(5)

A $CuCl_2$ saturated aqueous solution (15 ml) was diluted to 25 ml with water. Sodium nitrite (1.035 g, 5 mmole) was dissolved in 5 ml of water and slowly added to the $CuCl_2$ solution. After two minutes, 2-amino-5,6-dichlorobenzimidazole(4) (0.935 g, 5 mmole) was slowly added in small portions. The mixture was stirred at room temperature for 1 hr. Excess $CuCl_2$ solution was added and the mixture was heated o,n a steam bath for 1 hr. The aqueous solution was then extracted with ethyl acetate (3×50 ml) and the organic layer was washed with brine, dried with $MgSO_4$, concentrated, and separated on a silica column using 2% $MeOH/CHCl_3$ to afford 545 mg (49.5%) of2,5,6-trichlorobenzimidazole(5). $^1H$ NMR, TLC, and MS analysis were identical to the same compound obtained by Method A.

Method C(5)

5,6-Dichlorobenzimidazole-2-thione (3) was prepared according to the method of Van. Allen and Deacon, as described in Van Allen, J. A. et al., Org. Syn. IV:569. Carbon disuffide (84.5 mL 107.0 g, 1.4M) was added to a solution of KOH (92.4 g, of 85% purity, 78.5 g, 1.4M) in EtOH (1.5 L) and the resulting yellow solution was stirred without heating until a white precipitate was obtained. To obtain the product in good yield, potassium ethyl xanthate must be prepared in situ. 4,5-Dichloro-1,2- phenylenediamine (201.8 g, 1.14M) dissolved in absolute EtOH (3 L) was then added and the reaction mixture was heated under reflux for 24 hr. After cooling to room temperature the solvent was removed (caution - stench) under reduced pressure and the residue dissolved in $H_2O$ (3.0 L). The solution was adjusted io pH 2 with AcOH to precipitate the product. This solid was collected by filtration, washed with $H_2O$, and the solid was dried under reduced pressure at 60° C. for 48 hr to yield 236.4 g (94.6%) of 5,6-dichlorobenzimidazole-2-thione (3), MP: 328°–330° C. Also commercially available from Maybridge Chemical Company, Ltd., lit. MP given as, >320° C. TLC: $R_f$=0.62 ($CHCl_3$-MeOH, 10:1; $SiO_2$).

To a five liter three neck roundbottom flask fitted with an overhead stirrer and a reflux condenser was added $H_2O$ (1500 mL) and sodium percarbonate commercially available from Fluka Corporation. (209.3 g, 1.2M, 90% pure). For a leading reference see Ando, T. et al., Chem. Letters 665–666 (1986). After a solution was obtained, 5,6-dichlorobenzimidazole-2-thione (3) (131.5 g, 0.6M) was added in several portions. (Caution: exothermic with foaming). After stirring overnight, without heating, an additional 21 g of sodium percarbonate was added and the mixture was heated under reflux until a clear solution was obtained. The hot solution was treated with charcoal, filtered through Celite, then cooled to 25° C. in an ice bath. With cooling, concentrated HCl was added very carefully until pH 1 was obtained. The product precipitated as a white crystalline solid. After storing at 5° C. for 24 hr, the precipitate was collected by filtration, washed with cold $H_2O$ (500 mL) then dried at 80° C. under reduced pressure for 20 hr to yield 135.0 g (84%) of 5,6-dichlorobenzimidazole-2-sulfonic acid (9). MP: 353°–354° C. (eff.). TLC: $R_f$=0.27 ($CHCl_3$-MeOH, 4:1, $SiO_2$).

A modified procedure of Balli and Kersting procedure described in Balli, H. et al., Justis Liebigs Am. Chem. 1:647 (1961), was followed. A one liter three neck roundbottom flask was fitted with an over head stirrer and a reflux condenser connected to a gas scrubber. To the flask was added in order, phosphorus oxychloride (80 mL), phosphorus pentachloride (104.0 g, 0.5M) and 5,6-dichlorobenzimidazole-2-sulfonic acid (9) (66.8 g, 0.25M). The resulting mixture was carefully heated until an exothermic reaction occurred. The heat source was removed. When the reaction had subsided, the mixture was carefully heated to reflux. After all gas evolution had ceased (5 hr) the mixture was protected from moisture and allowed to cool to 25° C. The resulting thick slurry was carefully added to cold H₂O (2.5 L) containing some ice. Ice was added as needed. The aqueous mixture was allowed to stand for 18 hr at 5° C. while the product precipitated. The pH of the mixture was adjusted to pH 8 with conc. NH₄OH then acidified to pH 3 with glacial AcOH. The solid was collected by filtration, washed with H₂O, then dried on the filter. The material was dissolved in THF, treated with charcoal, then filtered through Celite. The solvent was removed under reduced pressure. The solid residue was dried at 60° C. under reduced pressure for 18 hr to yield 39.9 g (72%) of 2,5,6-trichlorobenzimidazole (5). MP: 212°–214° C. (eff. then solidifies). See Kawashima, E. et al., *Nucleic Acid Chemistry: Improved and New Synthetic Procedures, Method and Techniques*, eds. Townsend, L. B. et al., Wiley Interscience New York, N.Y., Part IV p. 96 (1991). TLC: $R_f$=0.89 (EtOAc; SiO₂). Recrystallization from benzene-hexane raises the melting point to 223°–224° C.

2-Amino-5,6-dichlorobenzimidazole (4)

A modified procedure of the procedure described by Leonard, N. J., et al., *J. Am. Chem. Soc.* 69:2459 (1947), was followed. Cyanogen bromide (136.6 g, 1.3M, 260 mL of a 5M solution in CH₃CN from) was added to a solution of MeOH (250 mL) in H₂O (1500 mL). 4,5- Dichloro-1,2-phenylenediamine (available commercially from Aldrich Chemical Company) (222.4 g, 1.26M) was then added in five portions, as the initial reaction is exothermic. The reaction mixture was stirred without heating for 80 hr. then treated with activated charcoal (5 g). The 80 hr time period was for convenience alone, since the reaction is probably complete within 24 hr. After stirring for two hrs, the reaction mixture was filtered through Celite. The filter cake was washed with MeOH (250 mL) and H₂O (750 mL) and the filter cake was discarded. The filtrate was diluted with H₂O (1.5 L), adjusted to pH 10 with conc. NH4OH (1750 mL) and then allowed to stand overnight at 5° C. The precipitate (yellow leaflets) was collected by filtration, washed with H₂O and then dried under reduced pressure at 50° C. for 60 hr. Crude yield: 265 g. This product was purified by recrystallization from CH₃CN to yield: 205.6 g (80.7%) of 4. MP: 264°–266° C. TLC: $R_f$=0.22 (CHCl₃-MeOH), 10:1; SiO₂). See Homer, J. K. et al., *J. Med. Chem.* 11:946–949 (1968), lit. MP: 260°–262° C. As an alternative, the crude material is dissolved in absolute ethanol, treated with activated charcoal, and the solution diluted with an equal volume of H₂O and stored at 5° C. for 18–24 hr.

2-Bromo-5,6-dichlorobenzimidazole (7)

Method A(7)

2-Amino-5,6-dichlorobenzimidazole (3 g, 16 mmole) was suspended in 150 ml of water and brought into solution with 2 ml of HBr. Sodium nitrite (3.3 g, 55 mmole) was then added and the mixture was stirred at room temperature for 1 hr. Excess CuBr₂ was then added and the mixture was heated on a steam bath for 1 hr. The aqueous solution was extracted with ethyl acetate (3×100 ml), dried with MgSO₄, concentrated, and crystallized from ethyl ether to give 1.13 g (26%) of 2-bromo-5,6-dichlorobenzimidazole (7). ¹H NMR (DMSO-d₆) δ 7.81 ppm (s, 2H), 13.62 (s, 1H). GC/MS: m/e 266, 185, 158, 150, 133, 124, 107, 97, 88, 73; 62; 52, 37.

Method B (7)

This preparation was based on work reported by Doyle et al., *J. Org. Chem.* 42:2426 (1977). A two liter three neck roundbottom flask was fitted with an overhead stirrer and a reflux condenser with an attached bubbler. Acetone (225 mL), that had been filtered through anhydrous magnesium sulfate, and isopentyl nitrite (25.1 mL, 29.2 g, 0.25M) were added and the resulting solution stirred for 5 min. CuBr₂ (23.5 g, 0.105M) was then added and stirring was continued for an additional 75 min to give a yellow-black solution. Powdered 2-amino-5,6-dichlorobenzimidazole (3) (20.2 g, 0.1M) was added in one portion and the mixture stirred without heating. Gas evolution was almost immediate and very vigorous; the reaction was exothermic to the point that a gentle reflux was maintained. During this time, an orange solid began to separate. After 25 min, the rate of reflux began to decrease, and after 35 min was very slow. The mixture was then heated under reflux until gas evolution had almost ceased. The mixture was cooled for 20 min in an ice bath then treated with 48% aqueous HBr (100 mL) giving a black suspension. After stirring for 20 min, H₂O was added and an orange precipitate was obtained. Stirring was continued for 30 min and then the precipitate was removed by filtration. (Caution - strong lachrymator, probably bromoacetone, present). The solid was suspended in H₂O and the mixture adjusted to pH 7 with saturated NaHCO₃. The solid was collected by filtration washed with H₂O then dried at 50° C. under reduced pressure for 18 hr to yield 20.9 g (79%) of crude. (7). TLC: $R_f$=0.0, 0.36 (5,6-dichlorobenzimidazol-2-one), 0.80 (7) (EtOAc-hexanes, 5:1; SiO₂). TLC: $R_f$=EtOAc-hexanes, 5:1; SiO₂). NMR: (DMSO-d₆) d 7.804, s, 2H, H4, H7. UV (EtOH): pH7 224, 253, 260, 292, 299; pH1 211,251,289, 298; pH11 221,294, 301.

2,5,6-Trichloro-1-(2,3,5-tri-O-aetyl-β-D-ribofuranosyl)benzimidazole (42)

To a suspension of (5) (62.01 3 g, 280 mmol) in 1.4 L of dry MeCN under argon, was added 70 mL (280 mmol) of BSA. The reaction mixture was stirred at room temperature for 15 min to give a clear solution. To this solution were added 1,2,3,5-Tetra-O-acetyl-β-D-ribofuranose (89.096 g, 280 retool) and then 60 mL (31 0 mmol) of TMSOTf was added dropwise over 20 min. After the addition had been completed, stirring was continued at room temperature for an additional 30 min. The reaction mixture was diluted with 4 L of EtOAc. The EtOAc solution was washed with 1:1 saturated aqueous NaHCO₃/saturated aquenous NaCl (3×2 L), dried (with Na₂SO₄, 100 g), decolorized (activated charcoal, 8 g) and filtered through Celite. The filtrate was evaporated and the residue was recrystallized from MeOH to give 116.88 g (3 crops, 87%) of (42) as white needles. The recrystallization was accomplished by heating the crude product in MeOH at reflux on a steam bath for a few minutes and then decanting the supernatant while hot into a clean beaker. Immediate crystallization resulted. A second portion of fresh MeOH was added to the remaining solid and the whole process was repeated until all of the solid was dissolved. MP: 145°–146° C. This product was pure by ¹H NMR.

2,5,6-Trichloro-1-(β-D-ribofuranosyl)benzimidazole (45)

Method A (45)

2,5,6-Trichlorobenzimidazole (700 mg, 0.0032 moles) was dissolved in acetonitrile and BSTFA (1 ml, 0.0038 moles) was added. The mixture was heated at 75° C. for 20 minutes. TMSTf (1 ml, 0.0051 moles) and 1-O-acetyl-2,3, 5-tri-O-benzoyl-β-D-ribofuranose (1.9 g, 0.0038 moles) were added while heating was continued for 45 min. The acetonitrile was removed under reduced pressure and the protected nucleoside was separated on a silica column, eluting with chloroform. The benzoyl protecting groups were removed by overnight treatment at room temperature with methanolic ammonia. The nucleoside was separated on a column using 50% EtOAc/hexane and then 10% MeOH/CHCl$_3$. The isolated compound was recrystallized from methanol. Yield: (74%); MP: 185°–186° C.; TLC (10% MeOH/CHCl$_3$): Rf=0.20; $^1$H NMR (DMSO-d$_6$) δ 3.68 ppm (q, 2H), 4.00 (d, 1H), 4.12 (t, 1 H), 4.40 (q, 1H), 5.28 (d, 1H), 5.41 (t, 1H), 5.49 (d, 1H), 5.57 (d, 1H), 7.96 (s, 1H), 8.55 (s, 1H); $^{13}$C NMR (DMSO-d$_6$, Broad band decoupling): d 61.08 ppm, 69.80, 71.70, 86.47, 89.16, 114.93, 120.04, 125.77, 125.97, 132.30, 140.96, 142.16; MS (Fast Atom Bombardment): m/e (M$^+$6) 359, (M$^+$4) 357, (M$^+$2) 355, (M$^+$) 353, 319, 285, 263, 221, 187, 177, 133, 115, 103, 97, 85.

Method B (45)

To a solution of Na$_2$CO$_3$ (23.32 g, 220 mmol) in 440 mL of H$_2$O were added successively 2.0 L of EtOH, 2.0 L of MeOH, and 105.5 g (220 mmol) of 42. The reaction mixture was stirred at room temperature for 2 hr. AcOH (26.44 mL, 462 mmol) was added and stirring was continued at room temperature for 20 min. The reaction mixture was filtered. The solid product was triturated with H$_2$O (800 mL, 20 min), MeOH (500 mL, 30 min), and then recrystallized from EtOH/MeOH (1 L/1 L) to give 52.4 g of 45 as white crystals {2 crops, the 2nd crop (2.8 g) was obtained by evaporation of the mother liquid and recrystallization of the residue two more times from EtOH/MeOH}. Recrystallization was accomplished by dissolving the crude product in a minimum amount of boiling EtOH, diluting it immediately with an equal amount of hot MeOH and allowing it to slowly cool. The filtrate was evaporated and the residue was triturated with H$_2$O (500 mL, 20 min), MeOH (500 mL, 30 min), and then recrystallized twice from EtOH/MeOH to give an additional 15.34 g of 45 {2 crops, the 2nd crop (1.95 g) was obtained by evaporation of the mother liquid and recrystallization of the residue two more times from EtOH/MeOH}. The total of 45 was 67.74 g (87%). MP: 166°–168° C.

2-Bromo-5,6-dichloro-1-(2,3,5-tri-O-acetyl-β-D-ribofuranosyl)benzimidazole (52a)

To a suspension of (7) (47.867 g, 180 mmol) in 540 mL of dry MeCN, was added 45 mL (180 mmol) of BSA. The reaction mixture was stirred at room temperature for 15 min to give a clear solution. A small amount of solid impurity remained unsilylated, believed to be 5,6-dichlorobenzimidazol-2-one from the starting material(7). 1,2,3,5-Tetra-O-acetyl-β-D-ribofuranose (60.14 g, 189 mmole) was added to this solution and then TMSOTf (38.267 mL 198 mmol) was added dropwise over 20 min. After the addition had been completed, stirring was continued at room temperature for 30 min. The reaction mixture was diluted with 2 L of EtOAc. The EtOAc solution was washed with 1:1 saturated aqueous NaHCO$_3$/saturated aqueous NaCl (1.5 L×2), dried (Na$_2$SO$_4$, 100 g), decolorized (activated charcoal, 6 g), and filtered through Celite. The filtrate was evaporated and the residue was recrystallized from MeOH to give 82.21 g (4 crops, 87%) of 52a as white needles. MP: 140°–144° C. This product was pure by $^1$H NMR.

2-Bromo-5,6-dichloro-1-(β-D-ribofuranosyl)benzimidazole (52)

Method A (52)

2-Bromo-5,6-dichlorobenzimidazole (7) (1 g, 3.8 mmole) was dissolved in dry acetonitrile (150 ml) and stirred in an inert atmosphere at 60° C. BSA (1.03 ml, 4.2 mmole) was added and the mixture was stirred for 10 minutes. 1,2,3,5-Tetra-O-acetyl-β-D-ribofuranose (1.21 g, 3.8 mmole) and TMSTf (0.81 ml, 4.2 mmole) were added to the clear solution and the mixture was stirred for 10 min. An additional quantity of 1,2,3,5-tetra-O-acetyl-D-ribofuranose (1.21 g, 3.8 mmole) and TMSTf (0.81 ml, 4.2 mmole) were added to the clear solution and the mixture was allowed to stir at 60° C. for 1 hr. The mixture was concentrated under reduced pressure and separated on a silica column to give the protected 2-bromo-5,6-dichlorobenzimidazole nucleoside. $^{13}$C NMR (CDCl$_3$): δ 170.26 ppm, 169.50, 168.99, 142.97, 132.32, 130.71, 128.09, 128.06, 121.09, 112.98, 88.09, 80.76, 71.01, 69.50, 62.87, 20.97, 20.49, 20.13. $^1$H NMR (CDCl$_3$): δ 2.02 ppm (s, 3H), 2.16 (s, 3H), 2.29 (s, 3H), 4.38 (m, 1H), 4.46 (ddd, 2H), 5.43 (dd, 1H), 5.43 (t, 1H), 6.17 (d, 1), 7.78 (s, 1H), 7.81 (s, 1H). The protected nucleoside was stirred overnight at room temperature in a methanolic ammonia solution, concentrated, and suspended in methanol (3×25 ml) to yield 2-bromo-5,6-dichloro-1-(β-D-ribofuranosyl)benzimidazole nucleoside in 137%. $^{13}$C NMR (DMSO-d$_6$): δ 142.57 ppm, 132.60, 132.57, 125.76, 119.86, 114.73, 90.21, 86.35, 71.55, 69.76, 61.05. $^1$H NMR (DMSO-d$_6$): δ 3.69 ppm (m, 2H), 3.99 (m, 1H), 4.11 (m, 1H), 4.41 (q, 1H), 5.27 (d, 1H), 5.40 (t, 1H), 5.45 (d, 1H), 5.87 (d, 1H), 7.95 (s, 1H), 8.56 (s, 1H). MS (FAB): m/e 399, 351, 319, 285, 267, 219, 187, 153, 133, 103, 85.

Method B (52)

To a solution of Na$_2$CO$_3$ (2.12 g, 20 min) in 40 mL of H$_2$O, were added successively 180 mL of EtOH, 180 mL of MeOH, and 10.483 g (20 mmol) of 51a. The reaction mixture was stirred at room temperature for 1.5 hr. AcOH (2.404 mL, 42 mmol) was added and stirring was continued at room temperature for 10 min. The reaction mixture was evaporated and the solid product was triturated with H$_2$O (200 mL, 20 min), MeOH (100 mL, 30 min), and then recrystallized from EtOH/MeOH, by dissolving the crude product in a minimum amount of boiling EtOH, diluting It immediately with an equal amount of hot MeOH and allowing it to slowly cool, to give 6.87 g of 52 as white crystals {2 crops, the 2nd crop (0.609 g) was obtained by evaporation of the mother liquor and recrystallization of the residue two more times from EtOH/MeOH}. MP: 162°–162° C.

2-Chloro-5,6-dinitro-1-(2,3,5-tri-O-benzyl-β-D-ribofuranosyl)benzimidazole (60)

To a mixture of 0.541 g (2.23 mmol) of 2-chloro-5,6-dinitrobenzimidazole in 12 mL of MeCN, was added 0.558 mL (2.23 mmol) of BSA. The reaction mixture was stirred at 75° C. for 15 min to give a clear solution. This solution was treated with the above MeCN solution of 2,3,5-tri-O-benzyl-D-ribofuranosyl chloride and 0.56 mL (2.90 mmol) of TMSOTf at 75° C. for 30 min. The reaction mixture was cooled and diluted with EtOAc (50 mL). The EtOAc solution was washed with sat. NaHCO$_3$ solution (50 mL×2), sat. NaCl solution (50 mL), dried (Na$_2$SO$_4$), and evaporated. The residue was chromatographed on a silica column (2.2× 18 cm, eluted with 20% EtOAc/hexane). Evaporation of fractions 10–14 (20 mL per fraction) gave 0.502 g (35%) of 60 as a syrup. MS: (FAB) m/e 645 (1%, MH$^+$=645). $^1$H NMR (DMSO-$d_6$): δ 8.50, 8.49 (2×s, 2, 7-H and 4-H), 7.34, 6.90 (2×m, 15, 3×Ph), 6.09 (d, 1, 1'-H, $J_{1'-2'}$=8.0 Hz), 4.73–4.27 (m, 9, 2'-H, 3'-H, 4'-H, and 3×PhCH$_2$), 3.77 (dd, 1, 5'-H, $J_{4'-5'}$=2.0 Hz, $J_{5'-5''}$=11.0 Hz), 3.65 (dd, 1, 5''-H, $J_{4'-5''}$=2.5 Hz).

2-Chloro-5,6-dinitro-1-β-D-ribofuranosylbenzimidazole (61)

To a solution of 0.454 g (0.719 mmol) of 60 in 12 mL of CH$_2$Cl$_2$, was added dropwise 8.4 mL of 1M BCl$_3$ at −7° C. The reaction mixture was stirred at −78° C. for 2 hr and then at −40° C. for 2 hr. MeOH (5 mL) was added and stirring was continued at −40° C. for 10 min. The reaction mixture was diluted with EtOAc (75 mL). The EtOAc solution was washed with cold H$_2$O (50 mL), sat. NaHCO$_3$ solution (50 mL), sat. NaCl solution (50 mL), dried (Na$_2$SO$_4$), and evaporated. The residue was coevaporated with MeOH (3×) and then suspended in a small amount of CHCl$_3$ for a few hours. The solid product was filtered to give 0.209 g of 61. This sample was contaminated by a small amount of 2-chloro-5,6-dinitrobenzimidazole. A part of the sample (0.18 g) was purffied on a silica column (2.4×10 cm, eluted with pure EtOAc). Evaporation of the appropriate fractions and crystallization by addition of CHCl$_3$ gave 0.084 g of 61 as a white solid. MP: 132°–135° C. MS: (EI) m/e 374.0276 (1%, M$^+$=374.0265). $^1$H NMR (DMSO-$d_6$): δ 9.18 (s, 1, 7-H), 8.60 (s, 1, 4-H), 6.00 (d, 1, 1'-H, $J_{1'-2'}$=7.5 Hz), 5.59 (d, 1, 2'-OH, $J_{2'-2'OH}$=6.0 Hz), 5.52 (t, 1, 5'-OH, $J_{5=-5'OH}$=4.5 Hz), 5.38 (d, 1, 3'-OH, $J_{3'-3'OH}$=4.5 Hz), 4.01 (m, 1, 2'-H, $J_{2'-3'}$=5.5 Hz), 4.16 (m, 1, 3'-H, $J_{3'-4'}$=2.0 Hz), 4.07 (m, 1, 4'-H, $J_{4'-5'}$=$J_{4'-5''}$=2.5 Hz), 3.73 (m, 2, 5'-H and 5''-H, $J_{5'-5''}$=12.0 Hz). $^{13}$C NMR (DMSO-$d_6$): δ 146.55 (C2), 142.63 (C3a), 138.90, 138.60 (C5 and C6), 134.12 (C7a), 116.67 (C4), 111.62 (C7), 89.98 (C1'), 86.91 (C4'), 72.86 (C2'), 69.84 (C3'), 60.85 (C5'). Anal Calcd. for C$_{12}$H$_{11}$ClN$_4$O$_8$: C, 38.47; H, 2.96; N, 14.95. Found: C, 38.46; H, 2.98; N, 14.62.

1-(2,3,5-Tri-O-acetyl-β-D-ribofuranosyl)-2,4,6-trichlorobenzimidazole (80)

To a suspension of 1.362 g (6.15 mmol) of 2,4,6-trichlorobenzimidzole in 31 mL of MeCN, was added 1.52 mL (6.15 mmol) of BSA. The reaction mixture was stirred at 80° C. for 15 min to give a clear solution. This solution was treated with 2.153 g (6.675 mmol) of 1,2,3,5-tetra-O-acetyl-β-D-ribofuranose and 1.426 mL (7.380 mmol) of TMSOTf at 80° C. for 1 hr. The reaction mixture was cooled and diluted with EtOAc (150 mL). The EtOAc solution was washed with sat. NaHCO$_3$ solution (150 mL×2), sat. NaCl solution (150 mL), dried (Na$_2$SO$_4$), and evaporated. The residue was coevaporated with MeOH and then suspended in 50 mL of hot MeOH. The suspension was cooled, filtered, and the solid product was washed with MeOH to give 2.103 g of 80 as white crystals (This product showed one spot on TLC). The mother liqdor was evaporated and the residue was chromatographed on a silica column (2.5×20 cm, eluted with CHCl$_3$ and 0.5% MeOH/CHCl$_3$). Evaporation of fractions 20–24 (20 mL per fraction) and recrystallization from MeOH gave an additional 0.258 g of 80 as white crystals. The total yield of 80 was 2.361 g (80%). MP: 198°–200° C. MS: (EI) m/e 480.0069 (4%, for C$_{18}$H$_{17}$$^{35}$Cl$_2$$^{37}$ClN2O$_7$: M$^+$=480.0072). $^1$H NMR (DMSO-$d_6$): δ 7.89 (d, 1, 7-H, $J_{7-5}$=2.0 Hz), 7.58 (d, 1, 5-H), 6.26 (d, 1, 1'-H, $J_{1'-2'}$=7.0 Hz), 5.54 (t, 1, 2'-H, $J_{2'-3'}$=7.0 Hz), 5.44 (dd, 1, 3'-H, $J_{3'-4'}$=4.5 Hz), 4.48, 4.38 (2×m, 3, 4'-H and 5'-H), 2.14, 2.02 (2×s, 9, 3×Ac). $^{13}$H NMR (DMSO-$d_6$): δ 169.84, 169.37, 169.09 (3×COCH$_3$), 140.91 (C2), 137.39 (C3a), 134.14 (C7a), 128.47 (C6), 123.66 (C4), 123.25 (C5), 111.06 (C7), 86.91 (C1'), 79.58 (C4'), 70.54 (C2'), 68.55 (C3'), 62.47 (C5'), 20.48, 20.19, 19.90 (3×COCH$_3$). Anal. Calcd. for C$_{18}$H$_{17}$Cl$_3$N$_2$O$_7$: C, 45.07; H, 3.57; N, 5.84. Found: C, 45.08; H, 3.62; N, 5.87.

2,4,6-Trichloro-1-β-D-ribofuranosylbenzimidazole (81)

A mixture of 0.130 g (0.271 mmol) of 80 in 5 mL of conc. NH$_4$OH/dioxane (1:1 by volume) was stirred in a pressure bottle at room temperature for 1 day. Volatile materials were removed by evaporation and coevaporation with MeOH (3×, bath temperature 40° C.). The resulting solid was absorbed on silica gel and was chromatographed on a silica column (2×5 cm, eluted successively with 1%, 2%, 3% MeOH/CRCl$_3$). Evaporation of fractions 23–39 (5 mL per fraction) gave a white solid. This solid was washed with H$_2$O, dried to give 46 mg (48%) of 80 as a white solid. MP: 165°–167° C. $^1$H NMR (DMSO-$d_6$): δ 8.36 (d, 1, 7-H, $J_{7-5}$=2.0 Hz), 7.52 (d, 1, 5-H), 5.90 (d, 1, 1'-H, $J_{1'-2'}$=8.0 Hz), 5.49 (d, 1, 2'-OH, $J_{2'-2'OH}$=6.5 Hz), 5.38 (t, 1, 5'-OH, $J_{5'-5'OH}$=4.5 Hz), 5.28 (d, 1, 3'-OH, $J_{3'-3'OH}$=4.5 Hz), 4.41 (m, 1, 2'-H, $J_{2'-3'}$=5.5 Hz), 4.14 (m, 1, 3'-H, $J_{3'-4'}$=2.0 Hz), 4.02 (m, 1, 4'-H, $J_{4'-5'}$=$J_{4'-5''}$=2.5 Hz), 3.70 (m, 2, 5'-H and 5''-H, $J_{5'-5''}$=12.0 Hz). $^{13}$H NMR (DMSO-$d_6$): δ 141.64 (C2), 137.50 (C3a), 134.17 (C7a), 128.02 (C6), 123.22 (C4) 122.77 (C5), 112.56 (C7), 89.35 (C1'), 86.52 (C4'), 71.71 (C2'), 69.70 (C3'), 61.02 (C5'). Anal. Calcd. for C$_{12}$H$_{11}$Cl$_3$N$_2$O$_4$: C, 40.76; H, 3.14; N, 7.92. Found: C, 40.74; H, 3.37; N, 7.71.

2-Iodo-5,6-dichloro-1-β-D-ribofuranosylbenzimidazole (83a)

2-Amino-5,6-dichloro-1-(2,3,5-tri-O-acetyl-β-D-ribofuranosyl)benzimidazole nudeoside (43) (50 mg, 0.1 mmole) was added to 3 mL of diiodomethane and amyl nitrite (0.13 ml, 1 mmole) under an inert atmosphere and heated to 50° C. for 1 hr. The mixture was concentrated under reduced pressure and chromatographed on a silica gel column to give one product which was treated with methanolic ammonia for 18 hr. The product was isolated, recrystallized and characterized as compound 83a. $^1$H NMR (DMSO-$d_6$): δ 3.71 (m, 2H), 4.07 (m, 1H), 4.12 (m, 1H), 4.40 (q, 1H), 5.23 (m, 1H), 5.37 (m, 2H), 5.82 (d, 1H), 7.89 (s, 1H), 8.52 (s, 1H). $^{13}$C NMR (DMSO-$d_6$): δ 145.33 ppm, 132.51, 125.26, 125.18, 119.51, 114.22, 110.32, 92.11, 86.22, 71.47, 69.99, 61.11. MP: 180°–182° C. UV $\lambda_{max}$ nm (ε×10$^4$): (pH 7) 230 (0.490), 259 (0.216), 292 (0.277) 302 (0.305); (pH 1) 230 (0.342), 258 (0.095), 294 (0.301), 303 (0.313); (pH 11) 228 (0.560), 258 (0.198), 292 (0.249), 302 (0.267). Anal. Calcd. for C$_{12}$H$_{11}$Cl$_2$IN$_2$O$_4$ 1.5CH$_3$OH: C, 32.88; H, 3.47; N, 5.68. Found: C, 33.32; H, 3.21; N, 5.80.

2-Chloro-4,5-dibromo-1-(2,3,5-tri-O-acetyl-β-D-ribofuranosyl)benzimidazole (84)

To a stirred mixture of 1.228 g (5.498 mmol) of CuBr$_2$ and 0.654 mL (4.949 mmol) of 90% t-BuONO in 10 mL of CH$_3$CN, was added dropwise a solution of 1.170 g (2.748 mmol) of 5-amino-2-chloro-1-(2,3,5-tri-O-acetyl-β-D-ribofuranosyl)benzimidazole in 3 mL of CH$_3$CN. After the addition, stirring was continued at room temperature for 2 hr. The reaction mixture was diluted with 100 mL of EtOAc. The EtOAc solution was washed with H$_2$O (100 mL), sat. NaHCO$_3$ solution (100 mL×2), sat. NaCl solution (100 mL), dried (Na$_2$SO$_4$), and evaporated. The residue was chromatographed on a silica column (4.1×30 cm, eluted with CHCl$_3$). Evaporation of fractions 59–78 (20 mL per fraction) and recrystallization from MeOH gave 0.600 g (38%) of 84 as a white solid. MP 202°–203° C. MS (EI) m/e 565.9109 (4%, M$^+$=565.909.1). $^1$H NMR (DMSO-d$_6$): δ 7.74 (2×d, 2, 6-H and 7-H, J$_{6-7}$=8.5 Hz), 6.26 (d; 1, 1'-H, J$_{1'-2'}$=6.5 Hz), 5.53 (t, 1, 2'-H, J$_{2'-3'}$=7.0 Hz), 5.42 (dd, 1, 3'-H, J$_{3'-4'}$=4.5 Hz), 4.42.

2-Chloro-4,5-dibromo-1-β-D-ribofuranosylbenzimidazole

A solution of 0.529 g (0.930 mmol) of 84 in 25 mL of NH$_3$/MeOH was stirred in a pressure bottle at room temperature for 5 hr. Volatile materials were removed by evaporation and coevaporation with MeOH (3×, bath temperature <40° C.). The resulting solid was recrystallized from MeOH/H$_2$O to give 0.316 g (2 crops, 77%) of 85 as white crystals. MP: 167–169° C. MS: (CI) m/e 440.8837 (20%, MH$^+$=440.8852). $^1$H NMR (DMSO-d$_6$): δ 8.05 (d, 1, 7-H, J$_{7-6}$=8.5 Hz), 7.59 (d, 1, 6-H), 5.89 (d, 1, 1'-H, J$_{1'-2'}$=7.5 Hz), 5.51 (d, 1, 2'-OH, J$_{2'-2'OH}$=6.5 Hz), 5.28 (d, 1, 3'-OH, J$_{3'-3'OH}$=4.5 Hz), 5.27 (t, 1, 5'-OH, J$_{5'-5'OH}$=5.0 Hz), 4.40 (m, 1, 2'-H, J$_{2'-3'}$=5.5 Hz), 4.13 (m, 1, 3'-H, J$_{3'-4'}$=2.0 Hz), 4.00 (m, 1, 4'-H, J$_{4'-5'}$=J$_{4'-5''}$=3.5 Hz), 3.68 (m, 2, 5'-H and 5"-H, J$_{5'-5''}$=12.0 Hz). $^{13}$H NMR (DMSO-d$_6$): δ 141.70 (C2), 141.56 (C3a), 132.21 (C7a), 127.42 (C6), 118.06 (C5), 114.08 (C4), 113.87 (C7), 89.45 (C1'), 86.34 (C4'), 71.74 (C2'), 69.62 (C3'), 61.07 (C5'). Anal. Calcd. for C$_{12}$H$_{11}$Br$_2$ClN$_2$O$_4$: C, 32.57; H, 2.51; N, 6.33. Found: C, 32.70; H, 2.33; N, 6.33.

2-Chloro-5,6-diiodobenzimidazole (41)

Compound 6-amino-2-chloro-5-iodobenzimidazole (26a) (0.190 g, 0.647 mmol) was dissolved in a mixture of conc. H$_2$SO$_4$/ice-H$_2$O (2 ml/3 mL) at 0° C. To this mixture, was added dropwise, a solution of NaNO$_2$/H$_2$O (0.134 g, 1.942 mmol/5 mL). The reaction mixture was stirred at room temperature for 1 hr. A solution of KI/H$_2$O (0.537 g/5 mL) was added dropwise and stirring was continued at room temperature for 3 h and then 100° C. for 15 min. The reaction mixture was extracted with EtOAc (50 mL×2). The EtOAc solution was washed with Na$_2$S$_2$O$_3$/H$_2$O (1 g/50 mL), sat. NaHCO$_3$ (50 mL), sat. NaCl solution (50 mL), dried (Na$_2$SO$_4$), and evaporated. The residue was recrystallized from MeOH to give 0.169 g of a yellowish crystalline compound. The mother liquor was evaporated and the residue was chromatographed on a silica column (2×4 cm, eluted successively with 1%, 2% MeOH/CHCl$_3$). Evaporation of fractions 4–6 (20 mL per fraction) and recrystallization from MedH gave an additional 0.040 g of product. The total yield was 0.209 g (80%). MP: 228°–229° C. (dec). MS: (EI) m/e 403.8064 (100%, M$^+$=403.6074). $^1$H NMR (DMSO-d$_6$): δ 13.50 (br s, 1, 1-NH), 8.11 (s, 2, 4-H and 7-H). Anal. Calcd. for C$_7$H$_3$ClI$_2$N$_2$: C, 20.79; H, 0.75; N, 6.93. Found: C, 20.73; H, 0.83; N, 6.74.

2-Chloro-5,6-diiodo-1-β-D-ribofuranosylbenzimidazole (107)

To a suspension of 0.230 g (0.569 mmol) of 2-chloro-5,6-diiodobenzimidazole (41) in 5 mL of MeCN, was added 0.140 mL (0.509 mmol) of BSA. The reaction mixture was stirred at 80° C. for 15 min to give a clear solution. This solution was treated with 0.199 g (0.626 mmol) of 1,2,3,5-tetra-O-acetyl-β-D-ribofuranose and 0.132 mL (0.683 mmol) of TMSOTf at 80° C. for 45 min. The reaction mixture was cooled and diluted with EtOAc (50 mL). The EtOAc solution was washed with sat. NaHCO$_3$ solution (50 mL×2), sat. NaCl solution (50 mL), dried (Na$_2$SO$_4$), and evaporated. The residue was chromatographed on a silica column (2.4×15 cm, eluted with CHCl$_3$). Evaporation of fractions 18–25 (20 mL per fraction) and recrystallization from MeOH gave 0.157 g (42%) of the blocked nucleoside as white crystals. MP: 120°–123° C. MS: (EI) m/e 661.8823 (14%, M$^+$=661.8814). $^1$H NMR (DMSO-d6): δ 8.34 (s, 1,7-H), 8.25 (s, 1,4-H), 6.22 (d, 1, 1-H J$_{1'-2'}$=7.0 HZ), 5.54 (t, 1, 2'-H, J$_{2'-3'}$=7.0 Hz), 5.41 (dd, 1, 3'-H, J$_{3'-4'}$=4.5 Hz); 4.46, 4.36 (2×m, 3, 4'-H and 5'-H), 2.16, 2.14, 2.01 (3×s, 9, 3×Ac). $^{13}$H NMR (DMSO-d$_6$): δ 169.94, 169.45, 169.15 (3×COCH$_3$), 142.54 (C3a), 140.67 (C2), 134.08 (C7a), 128.88 (C4), 721.48 (C7), 101.98, 101.32 (C5 and C6), 86.53 (C1'), 79.48 (C4'), 70.51 (C2'), 68.71 (C3'), 62.57 (C5'), 20.90, 20.27, 19.98 (3×COCH$_3$). Anal. Calcd. for C$_{18}$H$_{17}$ClI$_2$N$_2$O$_7$: C, 32.63; H, 2.59; N, 4.23. Found: C, 32.81; H, 2.63; N, 4.25. This compound was deprotected to afford compound 107.

2,5,6-Trichloro-1-(2-deoxy-3,5-di-O-p-toluoyl-β-D-erythro-pentofuranosyl)benzimidazole (110)

To a suspension of 4.43 g (20 mmol) of 2,5,6-trichlorobenzimidazole (5) in 100 mL of dry MeCN, was added portionwise 1.2 g (30 mmol) of 60% NaH in oil at room temperature. After the addition had been completed, the reaction mixture was stirred at room temperature for 20 min. to give a nearly clear yellowish solution. To this solution, compound 3,5-di-O-p-toluyl-β-D-erythro-pentofuranosyl chloride (9.332 g, 24 mmol) was added portionwise over 20 min and stirring was continued at room temperature for an additional 2 h. The reaction mixture was filtered and the solid was washed with portions of EtOAc (~300 mL). The filtrate was evaporated and the residue was dissolved in the EtOAc washings. This ETOAc solution was washed with half sat. NaCl solution (150 mL×2), dded (Na$_2$SO$_4$), and evaporated. The residue was added to 100 mL of MeOH, the mixture was heated at reflux temperature for 5 min. and was then allowed to cool to room temperature. Filtration of the resulting suspension and washing the solid with portions of MeOH gave 10.21 g (89%, 2 crops) of 110 as white crystals. MP: 168°–169° C. MS: (EI) m/e 572.0664 (0.5%, M$^+$=572.0673). $^1$H NMR (DMSO-d$_6$): δ 8.04, 7.94 (2×s, 2, 7-H and 4-H), 7.97, 7.86, 7.37, 7.29 (4×d, 8, Ph, J=8.0 Hz), 6.56 (dd, 1, 1'-H, J$_{1'-2'}$=8.5 Hz, J$_{1'-2''}$=6.0 Hz), 5.75 (m, 1, 3'-H, J$_{3'-2'}$=8.0 Hz, J$_{3'-2''}$=2.0 Hz, J$_{3'-4'}$=3.5 Hz), 4.72 (dd, 1, 5'-H J$_{5'-4'}$=3.5 Hz, J$_{5'-5''}$=12.0 Hz), 4.69 (dd, 1, 5"-H, J$_{5''-4'}$=5.0 Hz), 4.61 (m, 1, 4'-H), 3.02 (m, 1, 2'-H, J$_{2'-2''}$=14.5 Hz), 2.72 (m, 1, 2"-H), 2.40, 2.36 (2×s, 6, 2×Me). $^{13}$C NMR (DMSO-d$_6$): δ 165.48, 165.34 (2×p-MePhCO), 144.05, 143.81 (2×p-MePhCO), 141.38 (C2), 140.81 (C3a), 132.43 (C7a), 129.48, 129.24 (2×p-MePhCO), 126.47, 126.39, 126.23, 125.91 (2×p-MePhCO, C6, and C5), 120.29 (C4), 113.43 (C7), 85.19 (C1'), 80.07 (C4'), 73.52 (C3'), 63.72 (C5'), 35.75 (C2'), 21.14, 21.09 (2×p-MePhCO). Anal. Calcd. for C$_{28}$H$_{23}$Cl$_3$N$_2$O$_5$: C, 58.60; H, 4.04; N, 4.88. Found: C, 58.35; H, 4.09; N, 4.83.

2,5,6-Trichlorobenzimidazole-1-2-deoxy-β-D-erythropentofuranosyl (111)

A suspension of 7.30 g (12.721 mmol) of 110 and 8.284 g (127.21 mmol) of KCN in 255 mL of 90% aq. EtOH was stirred at room temperature for 4 days. The reaction mixture was filtered and the filtrate was evaporated. The resulting solid was triturated successively with H$_2$O (50 mL×3), hexane (50 mL×3), CHCl$_3$ (50 mL), and was then recrystallized from MeOH to give 3.027 g (70%, 2 crops) of 111 as white crystals. MP: 178°–180° C. MS: (EI) m/e 335.9831

(12%, M$^+$=335.9835). $^1$H NMR (DMSO-d$_6$): δ 8.44 (s, 1, 7-H), 7.94 (s, 1, 4-H), 6.35 (dd, 1, 1'-H, J$_{1'-2'}$=9.0 Hz, J$_{1'-2''}$=6.0 Hz), 5.42 (d, 1, 3'-OH, J$_{3'-3'OH}$=4.5 Hz), 5.24 (t, 1, 5'-OH, J$_{5'-5'OH}$=5.0 Hz), 4.43 (m, 1, 3'-H, J$_{3'-2'}$=7.0 Hz, J$_{3'-2''}$=2.0 Hz, J$_{3'-4'}$=2.5 Hz), 3.90 (m, 1, 4'-H, J$_{4'-5'}$=3.0 Hz), 3.70 (dd, 2, 5'-H), 2.51 (m, 1, 2'-H, J$_{2'-2''}$=13.5 Hz), 2.19 (m, 1, 2"-H). $^{13}$C NMR (DMSO-d$_6$): δ 1 41.21 (C2), 140.95 (C3a), 132.27 (C7a), 125.91, 125.67 (C5 and C6), 120.02 (C4), 114.77 (C7), 87.68 (C4'), 85.70 (C1'), 69.99 (C3'), 60.86 (C5'), 38.96 (C2'). Anal. Calcd. for C$_{12}$H$_{11}$Cl$_3$N$_2$O$_3$: C, 42.69; H, 3.28; N, 8.30. Found: C, 42.40; H, 3.38; N, 8.07.

2-Bromo-5,6-dichloro-1-(deoxy-β-D-erythro-pentofuranosyl)benzimidazole (112)

To a suspension of 1.55 g (5.829 mmol) of 2-bromo-5,6-dichlorobenzimidazole (7) in 30 mL of dry MeCN, was added portionwise 0.35 g (8.750 mmol) of 60% NaH in oil at room temperature. After the addition had been completed, the reaction mixture was stirred at room temperature for 20 min to give a nearly clear yellowish solution. To this solution, the appropriate carbohydrate (2.72 g, 6.995 mmol) was added portionwise over 20 min and stirring was continued at room temperature for an additional 2.5 h. The reaction mixture was diluted with EtOAc (100 mL), filtered and the solid was washed with portions of EtOAc (20 mL). This EtOAc solution was washed with half sat. NaCl solution (1 00 mL×2), dried (Na$_2$SO$_4$), and evaporated. The residue was chromatographed on a silica column (4×16 cm, eluted with pure chloroform). Evaporation of fractions 18–91 and recrystallization of the residue from EtOH gave 2.927 g (81%, 2 crops) of the protected nucleoside as white crystals. MP: 157°–159° C. MS: (EI) m/e 616.0153 (0.2%, M$^{30}$=616.0167). $^1$H NMR (DMSO-d$_6$): δ 8.02, 7.95 (2×s, 2, 7-H and 4-H), 7.96, 7.86, 7.37, 7.29 (4×d, 8, Ph, J=8.0 Hz), 6.52 (dd, 1, 1'-H, J$_{1'-2'}$=9.0 Hz, J$_{1'-2''}$=6.0 Hz), 5.76 (m, 1, 3'-H, J$_{3'-2'}$=8.0 Hz, J$_{3'-2''}$=2.0 Hz, J$_{3'-4'}$=3.5 Hz), 4.71 (m, 2, 5'-H and 5"-H, J$_{5''-4'}$=4.0 Hz, J$_{5''-4'}$=4.5 Hz, J$_{5'-5''}$=12.0 Hz), 4.63 (m, 1, 4'-H), 3.00 (m, 1, 2'-H, J$_{2'-2''}$=14.5 Hz), 2.70 (m, 1,2"-H), 2.40, 2.36 (2×s, 6, 2×Me). $^{13}$C NMR (DMSO-d$_6$): δ 165.45, 165.27 (2×p-MePhCO), 144.00, 143.75 (2×p-MePhCO), 142.44 (C3a), 132.49 (C7a), 131.46 (C2), 129.40, 129.19 (2×p-MePhCO), 126.43, 126.36, 126.03, 125.77 (2×p-MePhCO, C6, and C5), 120.12 (C4), 113.29 (C7), 86.27 (C1'), 80.97 (C4'), 73.50 (C3'), 63.71 (C5'), 35.81 (C2'), 21.08, 21.03 (2×p-MePhCO). Anal. Calcd. for C$_{28}$H$_{23}$BrCl$_2$N$_2$O$_5$: C, 54.39; H, 3.75; N, 4.53. Found: C, 54.54; H, 3.59; N, 4.44.

A suspension of 0.618 g (1.0 mmol) of the protected nucleoside and 0.330 g (5.0 mmol) of KCN in 20 mL of 90% aq. EtOH was stirred at room temperature for 5 days. The reaction mixture was evaporated. The resulting solid was triturated successively with H$_2$O (10 mL×3), CHCl$_3$ (10 mL×3), and was then recrystallized from EtOH to give 0.300 g (79%, 3 crops) of 112 as white crystals. MP: 187°–188° C. MS: (EI) m/e 379.9332 (6%, M$^+$=379.9330). $^1$H NMR (DMSO-d$_6$): δ 8.48 (s, 1,7-H), 7.93 (s, 1,4-H), 6.33 (dd, 1, 1'-H, J$_{1'-2'}$=9.0 Hz, J$_{1'-2''}$=5.5 Hz), 5.48 (d, 1, 3'-OH, J$_{3'-3'OH}$=4.0 Hz), 5.31 (t, 1, 5'-OH, J$_{5'-5'OH}$=4.5 Hz), 4.43 (m, 1, 3'-H, J$_{3'-2''}$=6.5 Hz, J$_{3'-2''}$=1.5 Hz), 3.91 (m, 1, 4'-H), 3.71 (m, 2, 5'-H), 2.50 (m, 1, 2'-H, J$_{2'-2''}$=13.5 Hz), 2.15 (m, 1, 2'-H). $^{13}$C NMR (DMSO-d$_6$): δ 142.56 (C3a), 132.49 (C7a), 131.39 (C2), 126.75, 125.56 (C5 and C6), 119.63 (C4), 114.66 (C7), 87.68 (C4'), 68.94 (C1'), 70.02 (C3'), 60.68 (C5'), 39.00 (C2'). Anal. Calcd. for C$_{12}$H$_{11}$BrCl$_2$N$_2$O$_3$: C, 37.73; H, 2.90; N, 7.33. Found: C, 38.18; H, 2.80; N, 7.30.

5-Bromo-2,6-dichloro-1-β-D-ribofuranosylbenzimidazole (95)

To a suspension of 0.319 g (1.0 mmol) of 2,6-dichloro-1-β-D-ribofuranosylbenzimldazole (67) in 10 mL of H$_2$O, was added dropwise a sat. solution of Br$_2$/H$_2$O at room temperature. After the addition had been completed, stirring was continued for 3 hr. The reaction mixture was filtered and the solid was washed with portions of H$_2$O, and then recrystallized from MeOH to give 0.335 g (8%, as M MeOH) of 95 as white crystalline needles. MP 140°–142° C. MS (EI) m/e 395.9274 (2%, M$^+$=395.9279). $^1$H NMR (DMSO-d$_6$): δ 8.65 (s, 1, 7-H), 8.08 (s, 1, 4-H), 5.89 (d, 1, 1'-H, J$_{1'-2'}$=8.0 Hz), 5.49 (d, 1, 2'-OH, J$_{2'-2'OH}$=6.5 Hz), 5.40 (t, 5'-OH, J$_{5'-5'OH}$=4.0 Hz), 5.28 (d, 1, 3'-OH, J$_{3'-3'OH}$=4.5 HZ), 4.42 (m, 1, 2'-H, J$_{2'-3}$=5.5 Hz), 4.13 (m, 1, 3'-H, J$_{3'-4}$=1.5 Hz), 4.01 (m, 1, 4'-H, J$_{4'-5'}$=J$_{4'-5''}$=2.5 Hz), 3.70 (m, 2, 5'-H and 5"-H, J$_{5'-5''}$=12.0 Hz). Anal. Calcd. for C$_{12}$H$_{11}$BrCl$_2$N$_2$O$_4$ MeOH: C, 36.30; H, 3.51; N, 6.51. Found: C, 35.98; H, 3.60; N, 6.39.

6-Bromo-2,5-dichloro-1-β-D-ribofuranosylbenzimidazole (99)

To a suspension of 0.110 g (0.313 mmol, as C$_{12}$H$_{12}$Cl$_2$N$_2$O$_4$ MeOH) of 2,5-dichloro-1-β-D-ribofuranosylbenzimidazole (73) in 3 mL of H$_2$O was added dropwise 10 mL of a sat. solution of Br$_2$/H$_2$O at room temperature. After the addition had been completed, stirring was continued for 6 hr. The reaction mixture was filtered and the solid was washed with portions of H$_2$O, and then recrystallized from MeOH to give 0.091 g (73%, 2 crops) of 99 as white crystalline needles. MP 158°–159° C. MS (EI) m/e 395.9274 (5% M$^+$=395.9279). $^1$H NMR (DMSO-d$_6$): 6 8.69 (s, 1, 7-H), 7.96 (s, 1, 4-H), 5.88 (d, 1, 1'-H, J$_{1'-2}$=8.0 Hz), 5.51 (d, 1, 2+-OH, J$_{2'-2'OH}$=6.5 Hz), 5.41 (t, 5'-OH, J$_{5'-4'OH}$=4.5 Hz), 5.30 (d, 1, 3'-OH, J$_{3'-3'OH}$=4.5 Hz), 4.42 (m, 1, 2'-H, J$_{2'-3}$=5.5 Hz), 5.30 (d, 1, 3'-OH, J$_{3'-4}$=1.5 Hz), 4.01 (m, 1, 4'-H, J$_{4'-5'}$=J$_{4'-5''}$=2.5 Hz), 371 (m, 2, 5'-H and 5"-H, J$_{5'-5''}$=1.20 Hz). Anal. Calcd. for C$_{12}$H$_{11}$BrCl$_2$N$_2$O$_4$: C, 36.21; H, 2.79; N, 7.04. Found: C, 36.14; H, 2.90; N, 6.90.

4,5-Difluoro-1,2-phenylenediamine (10)

To a solution of 5.55 g (31.876 mmole), of 4,5-difluoro-2-nitroaniline in 50 mL of MeOH, were added 100 mL of 2N HCl and 8.90 g (159.380 mmole) of iron powder. The reaction mixture was stirred at room temperature for 2 hr and then filtered. The filtrate was neutralized with conc. NH$_4$OH to ~pH 8. The resulting suspension was filtered again and the filter cake was washed thoroughly with MeOH. The filtrate and washings were combined, concentrated to ~100 mL and extracted with CHCl$_3$ (100 mL×3). The CHCl$_3$ solution was washed with a sat. NaCl solution (100 mL×2), dried (Na$_2$SO$_4$), and evaporated. The residue was coevaporated with CHCl$_3$ to give 3.515 g (77%) of 10. This material was used in the next reaction without further purification. A brown crystalline sample of 10 was obtained by recrystallization from CCl$_4$. $^1$H NMR (DMSO-d$_6$): d 6.44 (t, 2, 3-H and 6-H, J$_{F-H}$=10.5 H), 4.59 (br. s, 4, 2×NH$_2$).

2-Amino-5,6-difluorobenzimidazole (11)

To a stirred solution of 4.9 mL of 5M BrCN/MeCN in 50 mL of H$_2$O, was added dropwise a solution of 3.515 g (24.389 mmole) of 10 in 50 mL of MeOH over 20 min. After the addition, stirring was continued at room temperature for 2 h. The reaction mixture was concentrated to ~50 mL arid was extracted with BOAc (50 mL×3). The combined EtOAc solution was back washed with 100 mL of H$_2$O and then discarded. The combined H$_2$O phase was basified with sat. NaHCO$_3$ solution (precipitation occurred) and was extracted again with EtOAc (70 mL×3). The EtOAc solution was dried (Na$_2$SO$_4$) and evaporated to dryness. The residue was suspended in 50 mL of CHCl$_3$ and filtered. The yellowish solid was washed with portions of CHCl$_3$ to give 3.40 g of 11. The filtrate and washings were evaporated to dryness and the procedure was repeated to give an additional 0.355 g of 11. The total yield of 11 was 3.755 g (91%). $^1$H NMR (DMSO-d$_6$) d 10.79 (br. s, 1, 1-NH), 7.06 (dd, 2, 4-H and 7-H, $^3J_{F-H}$=11.0 Hz, $^4J_{F-H}$=7.5 Hz), 6.30 (br. s, 2, 2-NH$_2$).

2-Chloro-5,6-difluorobenzimidazole (12)

To a stirred mixture of 40 mL of aqueous CuCl$_2$ solution (60% by weight) and 20 mL of H$_2$O was added a solution of NaNO$_2$/H$_2$O (2.08 g/10 mL), Compound 11 (1.69 g, 10 mmole) was then added portionwise over 5 min. The reaction mixture was stirred at room temperature for 1 hr. An additional 30 ml of the aqueous CuCl$_2$ solution (60% by weight) was added and the reaction mixture was heated on a steam bath for 10 min (a small amount of MeOH was added to suppress the formation of foam). The mixture was extracted with EtOAc (150 mL×2). The EtOAc solution was washed with sat. NaCl solution (100 mL×2), dried (Na$_2$SO$_4$) and evaporated. The residue was chromatographed on a silica column (3×15 cm) using 2% and 3% MeOH/CHCl$_3$ as eluants. Evaporation of the appropriate fractions gave a brownish solid. This solid was washed with Et$_2$O and dried to give 0.962 g of 12. The Et$_2$O washings were evaporated and the residue was repurified through a silica column (2×10 cm, eluted successively with 1%, 2% MeOH/CHCl$_3$). Evaporation of the appropriate fractions and washing of the residue with Et$_2$O gave an additional 0.152 g of 12. The total yield of 12 was 1.114 g (59%). MS m/e 187.9954 (100%, M$^+$=187.9953). $^1$H NMR (DMSO-d$_6$): d 13.5 (br. s, 1, 1-NH), 7.62 (t, 2, 4-H and 7-H, J$_{F-H}$=9.0 Hz.

2-Amino-5(6)-chloro-6(5)-fluorobenzimidazole (12b)

4-Chloro-5-fluoro-1,2-phenylenediamine (12a, 3.212 g, :20 mmol) was dissolved in 40 mL of MeOH and then added dropwise to a stirred solution of 4.4 mL of 5M BrCN/MeCN in 40 mL of H$_2$O over 30 min. After the addition, stirring was continued at room temperature for 3 hr. The reaction mixture was concentrated to ~40 mL and then was washed with EtOAc (100 mL). The EtOAc phase was extracted with H$_2$O (60 mL). The combined H$_2$O phase was neutral/zed with sat. NaHCO$_3$ solution to ~pH 8 and the resulting suspension was extracted with EtOAc (200 mL). The BOAc phase was washed with a mixture of sat. NaHCO$_3$/sat. NaCl solution (20 mL/180 mL), dried (Na$_2$SO$_4$), and evaporated. The residue was coevaporated with CHCl$_3$ (20 mL×2) and then was suspended in 50 mL of CHCl$_3$. The suspension was filtered to give 3.340 g. of 12b as a grey solid. The filtrate was evaporated and coevaporated with CHCl$_3$. The resulting solid was again suspended in a small amount of CHCl$_3$ and the suspension was filtered to give an additional 0.235 g of 12b. The total yield of 12b was 3.575 g (96%). This product showed a single spot on TLC. MP: 194°–196° C.. MS: (El) m/e 185.0156 (100%, M$^+$=185.0156). $^1$H NMR (DMSO-d$_6$): d 10.85, (br s, 1, 1-NH), 7.16 (d, 1, 4-H, $^4J_{F-H}$=7.0 Hz), 7.06 (d, 1, 7-H, $^3J_{F-H}$=10.0 Hz), 6.43 (br s, 2, 2-NH$_2$). Anal. Calcd. for C$_7$H$_5$ClFN$_3$: C, 45.30; H, 2.72; N, 22.64. Found: C, 45.14; H, 2.67; N, 22.44.

2,5(6)-Dichloro-6(5)-fluorobenzimidazole (12c)

Compound 12b (0.928 g, 5.0 mmol) was suspended in a solution of CuCl$_2$/H$_2$O (10 g/25 mL). To this suspension, was added dropwise a solution of NaNO$_2$/H$_2$O (3.45 g, 50 mmol/25 mL) at 70° C. over 30 min (5 mL of t-BuOH was added portionwise to suppress foaming). After the addition, stirring was continued at 70° C. for 15 min. The reaction mixture was cooled and extracted with EtOAc (75 mL×2). The EtOAc solution was filtered and the filtrate was washed with half sat. NaCl solution (100 mL), dried (Na$_2$SO$_4$), and evaporated. The residue was chromatographed on a silica column (2.4×25 cm, eluted successively with 1%, 2% MeOH/CHCl$_3$). Evaporation of fractions 23–35 (20 mL per fraction) gave 0.744 g (73%) of 12c as a yellowish solid. MP: 197°–198° C. MS: (El) m/e 203.9657 (100%, M$^+$=203.9657). $^1$H NMR (DMSO-d$_6$): d 13.50 (br s, 1, 1-NH), 7.76 (d, 1, 4-H, $^4J_{F-H}$=7.0 Hz), 7.61 (d, 1, 7-H, $^3J_{F-H}$=10.5 Hz). Anal. Calcd. for C$_7$H$_3$Cl$_2$FN$_2$: C, 41.01; H, 1.47; N, 13.66. Found: C, 41.00; H, 1.39; N, 13.59.

2,4,5,6-Tetrachlorobenzimidazole (13)

To a mixture of CuCl$_2$ (1.345 g, 10 mmol) and 0.99 mL of 90% t-BuONO (30 mmol) in 25 mL of acetone, was added portionwise 1.280 g (5 mmol) of 13b over a period of 3 min. After the addition had been completed, stirring was cohtinued at 60° C. for 2 h (with the addition of 0.99 mL of fresh 90% t-BuONO every 30 min). The reaction mixture was cooled to room temperature, poured into 50 mL of 2N HCl, and extracted with 150 mL of EtOAc. The EtOAc layer was washed with 2N HCl (50 mL×2), sat. NaCl solution (100 mL×2), dried (Na$_2$SO$_4$), and evaporated. The residue was chromatographed on a silica column (4×7 cm, eluted with CHCl$_3$, 1% MeOH/CHCl$_3$). Evaporation of fractions 31–45 (15 mL per fraction) and recrystallization from MeOH gave 0.531 g (2 crops, 49%) of 13 as slightly brownish crystals. MP: 243°–244° C. MS: (El) m/e 253.8952 (81%, M$^+$=253.5972). $^1$H NMR (DMSO-d$_6$): d 14.09 (br s, 1, 1-NH), 7.83 {s, 1, 7(4)-H}. Anal. Calcd. for C$_7$H$_2$Cl$_4$N$_2$: C 32.85, H 0.78, N 10.95. Found: C, 32.69; H, 0.84; N, 10.76.

2-Amino-4,5,6-trichlorobenzimidazole (13b)

To a stirred solution of 3.62 mL of 5M BrCN/MeCN in 35 mL of H$_2$O, was addrid dropwise a solution of 3,4,5-trichloro-1,2-phenylenediamine (13a) (3.478 g, 16.446 mmol) in 35 mL of MeOH. After the addition had been completed, stirring was continued at room temperature for 2 hr. The reaction mixture was concentrated to [18] 35 mL and was washed with EtOAc (50 mL). The EtOAc phase was extracted with H$_2$O (50 mL). The combined H$_2$O phase was neutralized with sat. NaHCO$_3$ solution to ~pH 8 and the resulting suspension was extracted with EtOAc (150 mL). The EtOAc phase was washed with a mixture of sat. NaHCO$_3$ and sat. NaCl solution (20 mL/130 mL), dried (Na$_2$SO$_4$), and evaporated. The residue was dissolved in MeOH, decolorized with charcoal, and then recrystallized from MeCN to give 3.098 g (2 crops, 80%) of 13b as a slightly grey crystals. MP: 255°–258° C. MS: (El) m/e 234.9473 (100%, M$^+$=234.9471). $^1$H NMR (DMSO-d$_6$): d 11.25 (br s, 1, 1-NH), 7.29 {s, 1, 7(4)-H}, 6.75 (br s, 2, 2-NH$_2$). Anal. Calcd. for C$_7$H$_4$Cl$_3$N$_3$: C 35.55, H 1.70, N 17.77, Found: C 35.72, H 1.78, N 17.89.

2-Chloro-5,6-dibrcmobenzimidazole (17)

To a suspension of 0.763 g (5 mmole) of 2-chlorobenzimidazole in 50 mL of 1:1 MeOH/H$_2$, was added dropwise a solution of 1 mL of Br$_2$ .in 10 mL of MeOH over a period of 30 min. The reaction mixture was stirred at room temperature overnight and was then filtered. The solid was washed with portions of H$_2$O until the washings were neutral. This solid was air dried and recrystallized from MeOH to give 1.115 g (3 crops, 72%) of 17. mp 228° C.; $^1$H NMR (DMSO-d$_6$) d 13–14 (br. s, 1, 1-NH), 7.93 (s, 2, 4-H, 7-H).

2-Chloro-5-nitrobenzimidazole (19)

To 21 0 mL of fuming HNO$_3$, 2-chlorobenzimidazole (13.42 g, 87.95 mmole) was added portionwise over a period of 10 min with stirring and ice-H$_2$O cooling. After the addition, the cooling bath was removed and stirring was continued at room temperature overnight. This reaction mixture was cooled to ~0° C., poured into 300 mL of ice, and neutralized carefully with conc. NH$_4$OH to ~pH 8. The resulting suspension was filtered. The yellowish solid product was washed with portions of H$_2$O and air-dried. The filtrate and washings were combined and extracted with EtOAc (200 mL×2). The EtOAc solution was washed with sat. NaCl solution (200 mL×2), dried (Na$_2$SO$_4$), and evaporated to give 1.3 g of a yellowish solid. The solid was combined with the major part of the product and was recrystallized from MeOH to give 16.34 g (5 crops, 94%) of 19 as yellowish crystals. mp 235°–237° C. MS (EI) m/e 196.9984 (100%, M$^+$=196.9992). $^1$H NMR (DMSO-d$_6$) d 14.06 (br. s, 1, 1-NH), 8.41 (s, 1, 4-H), 8.14 (dd,, 1, 6-H, J$_{6-4}$=2.0 Hz, J$_{6-7}$=9.0 Hz), 7.71 (d, 1, 7-H).

2-Chloro-4,5,6-tribromobenzimidazole (20)

To a suspension of 4.578 g (30 mmol) of 2-chlorobenzimidazole (16) in a mixture of MeOH/t-BudH/H$_2$O (20 mL/25 mL/100 mL), was added dropwise a solution of Br$_2$/MeOH (7.728 mL/20 mL) over 2 h. After the addition had been completed, the reaction mixture was stirred at room temperature for 1 day. More solvents (MeOH/H$_2$O, 25 mL/100 mL) were added, stirring was continued at room temperature for 2 days. Fresh Br$_2$/MeOH (1.546 mL/10 mL) was added, stirring was continued at room temperature for 1 day and then at 50° C. for 6 hr. The reaction mixture was cooled and filtered. The filter cake was washed with portions of H$_2$O, air-dried, and fractionally recrystallized from MeOH to give 1.70 g (15%) of 20 as crystalline needles (mainly one spot on TLC). {the major fraction (6.154 g) was a mixture of compounds 17, 20, and 2-chloro-4,5,6,7-tetrabromobenzimidazole (23}. MP: 263°–266° C. $^1$H NMR (DMSO-d$_6$): d 14.00 (br s, 1, 1-NH), 7.96 {s, 1, 7(4)-H}.

5(6)-Amino-2-chloro-6(5)-nitrobenzimidazole (25)

A mixture of 1.213 g (5.0 mmol) of 2-chloro-5,6-dinitrobenzimidazole (22) and 1.398: g (25 mmol) of iron powder In 50 mL of AcOH was stirred at room temperature for 4 h. The reaction mixture was diluted with 100 mL of EtOAc, filtered, and the solid was washed with portions of EtOAc (total EtOAc used ~100 mL). The filtrate and washings were combined and washed with H$_2$O (100 mL×3). The H$_2$O layer was extracted with 100 mL of EtOAc. The EtOAc solutions were combined, evaporated, coevaporated with toluene (10 mL×3), MeOH (10 mL×2) to give a brown solid.

The brown solid was absorbed on 30 mL of silica gel and was chromatographed on a silica column (3×25 cm, eluted successively with 2%, 4%, 8% MeOH/CHCl$_3$). Evaporation of fractions 30–58 (20 mL per fraction) and recrystallization from MeOH gave 0.431 g (2 crops, 41%) of 25 as red crystals. MP:>250° C. (dec). MS: (EI) m/e 212.0096 (100%, M$^+$=212.0101). $^1$H NMR (DMSO-d$_6$): d 13.07 (br s, 1, 1-NH), 8.15 (s, 1,7-H), 7.06 (s, 2, 5-NH$_2$), 6.91 (s, 1, 4-H). Anal. Calcd. for C$_7$H$_5$ClN$_4$O$_2$: C, 39.55; H, 2.37; N, 26.35. Found: C, 39.81; H, 2.11; N, 26.43.

2-Chloro-5(6)-iodo-6(5)-nitrobenzlmidazole (26) from 2-chloro-5,6-dinitrobenzimidazole (22)

A mixture of 1.213 g (5.0 mmol) of 22 and 1.398 g (25 mmol) of iron powder in 50 mL of AcOH was stirred at room temperature for 4 hr. The reaction mixture was diluted with 100 mL of BOAc, filtered, and the filtrate was washed with portions of EtOAc (total EtOAc used ~100 mL). The filtrate and washings were combined and washed with H$_2$O (50 mL×3). The H$_2$O layer was extracted with 100 mL of BOAc. The EtOAc solutions were combined, evaporated, coevaporated with toluene (10 mL×3), MeOH (10 mL×2) to give a brown solid.

The brown solid was dissolved in a mixture of Conc, H$_2$SO$_4$/ice-H$_2$O (14 mL/20 mL) at 0° C. To this mixture, was added dropwise a solution of NaNO$_2$/H$_2$O (0.994 g, 13.688 mmol/5 mL). The reaction mixture was stirred at )° C. for 1 hr. A solution of urea/H$_2$O (0.411 g/3 mL) was added and stirring was continued at 0° C. for 10 min. A solution of KI/H$_2$O (2.272 g/5 mL) was added and stirring was continued at room temperature for 18 h. The reaction mixture was extracted with EtOAc (100 mL×2). The EtOAc solution was washed with H$_2$O (100 mL), sat. NaHCO$_3$ (100 mL), sat. NaCl solution (100 mL), dried. (Na$_2$SO$_4$), and evaporated. The residue was chromatographed on a silica column (2.2× 25 cm, eluted successively with 1%, 2% MeOH/CHCl$_3$). Fractions 20–41 (20 mL per fraction) were collected, washed with Na$_2$S$_2$O$_3$/H$_2$O (1 g/100 mL), dried(Na$_2$SO$_4$), and evaporated. The residue was recrystallized from MeOH to gave 0.593 g (3 crops, 40%) of 26 as yellowish crystals. MP: ~213° C. (dec). MS: (EI) m/e 322.8968 (100%, M$^+$=322.8959). $^1$H NMR (DMSO-d$_6$): d 13.98 (br s, 1, 1-NH), 8.24, 8.16 (2×s, 2, 4-H and 7-H). Anal. Calcd. for C$_7$H$_3$ClIN$_3$O$_2$: C, 25.99; H, 0.93; N, 12.99. Found: C, 25.74; H, 0.73; N, 12.71.

6(5)-Amino-2-chloro-5(6)-iodobenzimidazole (26a)

A mixture of 0.339 g (1.048 mmol) of 26 and 0.090 g (wet) of Ra-Ni in 10 mL of EtOH was hydrogenated at room temperature, 50 psi of H$_2$ for 7 h. The reaction mixture was filtered and the filtrate was evaporated. The residue was chromatographed on a silica column (2×6 cm, eluted successively with 1%, 2%, 3% MeOH/CHCl$_3$). Evaporation of fractions 11–17 (20 mL per fraction) gave 0.190 g (62%) of 26a as a foam. An analytical sample (a yellowish crystalline compound) was obtained by recrystailization from MeOH. MP: >200° C. (dec). MS: (EI) m/e 292.9202 (100%, M$^+$=292.9217). $^1$H NMR (DMSO-d$_6$): d 12.80 (br s, 1, 1-NH), 7.75 ( s, 1, 4-H), 6.87 (s, 1, 7-H), 5.03 (s, 2, 6-NH$_2$). Anal. Calcd. for C$_7$H5ClIN$_3$: C, 28.65; H, 1.72; N, 14.32. Found: C, 28.84; H, 1.66; N, 14.17.

2,4,6-Trichlorobenzimidazole (32)

To a solution of CuCl$_2$/H$_2$O (45 g/100 mL), were added a solution of NaNO$_2$/H$_2$O (4.14 g, 60 mmol/20 mL) and then a solution of 29/MeOH (4.04 g, 20 mmol/20 mL). After the addition, stirring was continued at room temperature for 1 hr. The reaction mixture was then heated on a stem bath for 1 hr. During this period of heating, an additional fresh NaNO$_2$/H$_2$O solution (4.14 g, 60 mmol/20 mL) was added dropwise. The reaction mixture was cooled and extracted with EtOAc (200 mL×2). The EtOAc solution was filtered and the filtrate was washed with half sat. NaCl solution (200 mL×2), dried (Na$_2$SO$_4$), and evaporated. The residue was chromatographed on a silica column (4×25 cm, eluted with 2% MeOH/CHCl$_3$). Evaporation of fractions 46–68 (20 mL per fraction) gave 1.796 g (41%) of 8 as a white foam. An analytical sample was obtained by recrystallization from MeOH. MP: 233°–234° C. MS: (EI) m/e 219.9357 (100%, M$^+$=219.9362). $^1$H NMR (DMSO-d$_6$): d 13.92 (br s, 1, 1-NH), 7.58 "s", 1, 5-H or 7-H), 7.44 ("d", 1, 5-H or 7-H, J$_{5-7}$=1.5 Hz). Anal. calcd. for C$_7$H$_3$Cl$_3$N$_2$: C 37.96, H 1.37, N 12.65. Found: C 38.13, H 1.68, N 12.67.

2-Amino-5(6)-chlorobenzimidazole (34)

To a solution of 5M BrCN/CH$_3$CN (10 ml) in 100 ml of H$_2$O) was added dropwise a solution of 7.13 grams (50 mmoles) of 4-chloro-o-phenylenediamine in methanol (100 ml) over a period of 30 minutes while stirring. The contents were reacted at room temperature for an additional two hours. The reaction solution was concentrated to approximately 100 ml and extracted with EtOAc (200 ml/100 ml H$_2$O). The organic phase was extracted a second time with an additional 100 ml of distilled water and then discarded. The combined water phases were neutralized with 40 ml of saturated sodium bicarbonate. The resultant precipitate was collected by flitration. The filter cake was washed with portions of H$_2$O (100 ml) and air dried. The filtrate and washings were combined and extracted with EtOAc (100 ml×2). The EtOAc solution was dried (Na$_2$SO$_4$) and evaporated to give a solid. This was combined with the major part of the solid product and was coevaporated with EtOH (2×): The resulting solid was suspended in 100 ml of CHCl$_3$ and the suspension was filtered. The filter cake was washed with portions of CHCl$_3$, and air dried to give 6.62 grams of 34 as a yellowish solid. The filtrate and washings were evaporated and the residue was again suspended in a small amount of CHCl$_3$. Filtration of the suspension gave an additional 0.68 grams of 34 as a yellowish solid. This material was used for subsequent reactions without further purification. The total yield of 34 was 7.50 grams (90%). mp 159°–161° C. MS (EI) m/e 167.0243 (100%, M$^+$=167.0250). $^1$H NMR (DMSO-d$_6$) d 10.81 (br. s, 1, 1-NH), 7.09 (d, 1,4-H, J$_{4-6}$=2.0 Hz), 7.06 (d, 1, 7-H, J$_{7-6}$=8.5 Hz), 6.84 ("d", 1, 6-H), 6.33 br. s, 2, 2-NH$_2$).

2,5(6)-Dichlorobenzimidazole (35)

2-Amino-5(6)-chlorobenzimidazole (34) (10.06 grams, 60 mmoles) was added portionwise to an aqueous solution of cupric chloride (120 grams) and sodium nitrite (12.42 grams) while stirring. The reaction mixture was stirred for one hour at room temperature. At this time the reaction mixture was extracted with EtOAc (200 ml×3) to provide a brownish discoloration of the organic phase. The EtOAC phase was washed with saturated NaCl solution, dried with Na$_2$SO$_4$, and evaporated in vacuo to reveal a brown precipitate which was added to a silica column. Elution with 2% MeOH/CHCl$_3$, while increasing the polarity gradually to 5% MeOH/CHCl$_3$, and evaporation of the appropriate fractions provided a brownish-white precipitate which was suspended in Et$_2$O and filtered to yield 53.1% (grams) of 35. mp 209°–212° C. MS (EI) m/e 185.9751 (100%, M$^+$=185.9752). $^1$H NMR (DMSO-d$_6$) d 13.5 (br. s, 1, 1-NH), 7.59 (d, 1, 4-H, J$_{4-6}$=2.0 Hz), 7.52 (d, 1, 7-H, J$_{7-6}$=8.5 Hz), 7.25 (m, 1, 6-H).

2-Chloro-5,6-diiodobenzimidazole (41)

Compound 26a (0.190 g, 0.647 mmol) was dissolved in a mixture of conc. H$_2$SO$_4$/ice-H$_2$O (2 mL/3 mL) at 0° C. To this mixture, was added dropwise a solution of NaNO$_2$/H$_2$O (0.134 g, 1.942 mmol/5 mL). The reaction mixture was stirred at room temperature for 1 hr. A solution of KI/H$_2$O (0.537 g/5 mL) was added dropwise and stirring was continued at room temperature for 3 h and then 100° C. for 15 min. The reaction mixture was extracted with EtOAc (50 mL×2). The EtOAc solution was washed with Na$_2$S$_2$O$_3$/H$_2$O (1 g/50 mL), sat. NaHCO$_3$ (50 mL), sat. NaCl solution (50 mL), dried (Na$_2$SO$_4$), and evaporated. The residue was recrystallized from MeOH to give 0.169 g of 41 as a yellowish crystalline compound. The mother liquor was evaporated and the residue was chromatographed on a silica column (2×4 cm, eluted successively with 1%, 2% MeOH/CHCl$_3$). Evaporation of fractions 4–6 (20 mL per fraction) and recrystailization from MeOH gave additional 0.040 g of 41. The total yield of 41 was 0.209 g (80%). MP: 228°–229° C (dec). MS: (EI) m/e 403.8064 (100%, M$^+$=403.8074). $^1$H NMR (DMSO-d$_6$): d 13.50 (br s, 1, 1-NH), 8.11 (s, 2, 4-H and 7-H). Anal. Calcd. for C$_7$H$_3$Cl I$_2$N$_2$: C, 20.79; H, 0.75; N, 6.93. Found: C, 20.73; H, 0.83; N, 6.74.

2-Amino-4(7)-chloro-6(5)-trifluoromethylbenzimidazole (41b)

To a stirred solution of 4.8 mL of 5M BrCN/MeCN in 40 mL of H$_2$O, was added dropwise a solution of 3-chloro-5-trifluoromethyl-1,2-phenylenediamine (41a) (4.212 g, 20 mmol) in 40 mL of MeOH at room temperature over 30 min. After the addition had finished, stirring was continued at room temperature for 3 hr. The reaction mixture was concentrated to ~40 mL and then was washed with EtOAc (50 mL). The EtOAc phase was extracted with H$_2$O (50 mL). The combined H$_2$O phase was neutralized with sat. NaHCO$_3$ solution to ~pH 8 and the resulting suspension was extracted with EtOAc (100 mL×2). The EtOAc phase was washed with sat. NaCl solution (150 mL), dried (Na$_2$SO$_4$), and evaporated to give 3.913 g (53%) of 41b as a white foam. This product showed a single spot on TLC. An analytical sample was obtained by addition of CHCl$_3$ to the above foam to effect crystallization. MP: 180°–182° C. MS: (EI) m/e 235.0121 (100%, M$^+$=235.0124). $^1$H NMR (DMSO-d$_6$): d 11.77, 11.25 (2×br s*, 1, 1-NH), 7.35, 7.26 (2×s, 2, Ph), 6.90, 6.53 (2×br s*, 2, 2-NH$_2$). Anal. Calcd. for C$_8$H$_5$ClF$_3$N$_3$: C, 40.79; H, 2.14; N, 17.84. Found: C, 40.90; H, 2.34; N, 17.79.

*It indicated the existence of two tautomers.

2,4(7)-Dichloro-6(5)-trifluoromethylbenzimidazole (41c)

To a solution of CuCl$_2$/H$_2$O (20 g/50 mL), was added a solution of NaNO$_2$/H$_2$O (3.45 g, 50 mmol/20 mL). Compound 41b (2.356 g, 10 mmol) was then added portionwise over 10 min (2 mL of t-BuOH was added to help the mix). After the addition had finished, stirring was continued at room temperature for 1 h. The reaction mixture was then heated at 70° C. for 30 min. During this period of heating, an additional fresh NaNO$_2$/H$_2$O solution (3.45 g, 50 mmol/20 mL) was added dropwise. The reaction mixture was cooled and extracted with EtOAc (75 mL×2). The EtOAc solution was filtered and the filtrate was washed with sat. NaCl solution (100 mL×2), dried (Na$_2$SO$_4$), and evaporated. The residue was chromatographed on a silica column (3×25 cm, eluted with CHCl$_3$, 1% MeOH/CHCl$_3$). Evaporation of fractions 35–42 (20 mL per fraction) gave 1.369 g (54%) of 41c as a yellowish solid. An analytical sample was obtained by recrystallization from MeOH. MP: 187°–189° C. MS: (EI) m/e 253.9629 (100%, M$^+$=253.9625). $^1$H NMR (DMSO-d$_6$): d 14.22 (br s, 1, 1-NH), 7.86, 7.68 (2×s, 2, Ph). Anal. Calcd. for C$_8$H$_3$Cl$_2$F$_3$N$_2$: C, 37.68; H, 1.19; N, 10.98. Found: C, 37.81; H, 1.08; N, 11.06.

1-(5-O-Acetyl-β-D-ribofuranosyl)-2,5,6-trichlorobenzimidazole (42a)

A mixture of 42 (0.48 g, 1.0 mmol) and KOAc (0.49 g, 5.0 mmol) in MeOH/H$_2$O (20 mL/2 mL) was stirred at room temperature for 24 h. AcOH (0.286 mL, 5.0 mmol) was added and stirring was continued at room temperature for 15 min. The reaction mixture was evaporated and the residue was partitioned between $H_2O/CHCl_3$ (50 mL/50 mL). The $CHCl_3$ layer was washed with sat. NaCl solution (50 mL), dried ($Na_2SO_4$), and evaporated. The residue was chromatographed on a silica column (1.9×20 cm, eluted with $CHCl_3$, 1%, 2%, 4% MeOH/$CHCl_3$). Evaporation of fractions 42–51 (15 mL per fraction) and recrystlllization from MeOH gave 0.178 g (2 crops, 45%) of 42a as White crystals. MP: 82°–87° C. MS: (EI) m/e 393.9875 (20%, $M^+$=393.9890). $^1H$ NMR (DMSO-$d_6$): d 8.00, 7.96 (2×s, 2, 7-H and 4-H), 5.91 (d, 1, 1'-H, $J_{1'-2'}$=7.5 Hz), 5.59 (d, 1, 2'-OH, $J_{2'-2'OH}$=6.0 Hz), 5.45 (d, 1, 3'-OH, $J_{3'-3'OH}$=4.5 Hz), 4.44 (dd, 1, 5'-H, $J_{5'-4}$=4.5 Hz, $J_{5'-5}$=12.5 Hz), 4.42 (m, 1,2'-H, $J_{2'-3}$=6.0 Hz), 4.25 (dd, 1,5"-H, $J_{5'-4}$=2.5 Hz), 4.17 (m, 1,4'-H, $J_{3'-4}$=3.5 Hz), , 4,11 (m, 1, 3'-H), 2.14 (s, 3, 5'-OAc). $^{13}C$ NMR (DMSO-$d_6$): d 169.95 ($COCH_3$), 142.03 (C2), 140.92 (C3a), 132.30 (C7a), 125.96, 125.86 (C5 and C6), 120.28 (C4), 113.47 (C7), 89.32 (C1'), 82.53 (C4'), 71.41 (C2'), 69.03 (C3'), 63.35 (C5'), 20.56 ($COCH_3$). Anal Calcd. for $C_{14}H_{13}Cl_3N_2O_5$: C, 42.50; H, 3.31; N, 7.08. Found: C, 42.45; H, 3.20; N, 6.97.

2-Amino-5,6-dichloro-1-(2,3,5-tri-O-acetyl-β-D-ribofuranosyl) benzlmidazole (43)

2-Amino-5,6-dichlorobenzimidazole (4) (3 g, 16 mmole) was dissolved in dry acetonitrile (150 ml) and stirred in an inert atmosphere at 60° C. BSA (4.37 ml, 17 mmole) was added and the mixture was stirred for 10 minutes. 1,2,3,5-tetra-O-acetyl-β-D-ribofuranose (5.09 g, 16 mmole) and TMSTf (3.29 ml, 17 mmole) were added to the clear solution and the mixture was allowed to stir at 60° C. for 1 hr. The mixture was concentrated under reduced pressure and separated on a silica column to yield 1.14 g (15%) of 2-amino-5,6-dichloro-1-(2,3,5,tri-O-acetyl-β-D-ribofuranosyl) benzimidazole (43). $^{13}C$ NMR ($CDCl_3$): d 170.04ppm, 169.56, 169.11, 154.57, 141.64, 132.53, 125.90, 1123.45, 117.72, 109.49, 85.78, 80.99, 70.95, 69.83, 62.91, 20.74, 20.54, 20.20. $^1H$ NMR ($CDCl_3$): d 0.96 ppm (s, 3H), 1.09 (s, 3H), 1.13 (s, 3H), 3.75 (m, 2H), 4.08 (dd, 1H), 5.00 (dd, 1H), 5.13 (t, 1H), 5.42 (s, 2H), 5.61 (d, 1H), 7.27 (s, 1H), 7.42 (s, 1H). MS (FAB): m/e 758, 718, 676, 460, 426, 259, 217, 139.

2-Amino-5,6-dichloro-1-(β-D-ribofuranosyl) benzimidazole (44)

2,5,6-Trichloro-1-(2,3,5-tri-O-acetyl-β-D-ribofuranosyl) benzimidazole (42, 0.48 g; 1 mmole) was dissolved in dry MeOH (10 ml). Liq. $NH_3$(10 ml) was added and the mixture heated in a steel bomb at 100° C. for 2 hr. This mixture was stirred at room temperature for 24 hr. Excess $NH_3$ was allowed to evaporate and the solution evaporated to dryness, absorbed onto silica gel (2 g), and chromatographed on a silica gel column using silica gel (20 g; 60–200 mesh). Bution of the column with $CH_2Cl_2$:$CH_3OH$ (96:4) gave the desired compound 44 as the major nucleoside. Evaporation of the solvent and crystallization of the residue from EtOH gave 44 (0.62 g; yield 6.06%). top. 145° C.; UV $l_{max}$. (MeOH): 259 (7941) and 301 (8348) nm; $l_{max}$ (pH1): 215 (26000) and 292 (7520) nm; $l_{max}$ (pH11): 257 (7967) and 298 (7107) nm. $^1H$ NMR(DMSO- $d_6$): d 8.70 (s, 1H, $C_7$-H, 8.28(s,1H, $C_4$-H), 7.90 (bs,2H, $D_2O$ exchangeable, $NH_2$), 6.75(d,C1'H$J_{1,2}$=4.5 $H_z$) and the rest of the sugar protons.

1-(5-O-Acetyl-β-D-ribofuranosyl)-2-bromo-5,6-dichlorobenzimidazole (52b)

A mixture of 52a (1.048 g, 2.0 mmol) and KOAc (0.98 g, 10.0 mmol) in MeOH/$H_2O$ (40 mL/4 mL) was stirred at room temperature for 24 hr. AcOH (0.572 mL 10.0 mmol) was added and stirring was continued at room temperature for 15 min. The reaction mixture was evaporated and the residue was partitioned between. EtOAc/$H_2O$ (75 mL/75 mL). The EtOAc layer was washed with sat. NaCl solution (75 mL), dried ($Na_2SO_4$), and evaporated. The residue was chromatographed on a silica column (1.9×24 cm, eluted with $CHCl_3$, 2%, 3%, 4% MeOH/$CHCl_3$). Evaporation of fractions 15–27 (15 mL per fraction) and recrystallization from MeOH gave 0.50 g (2 crops, 57%) of 52b as white crystals. MP: 85°–95° C. (melted slowly over a large range) MS: (EI) m/e 437.9398 (15%, $M^+$=437.9385). $^1H$ NMR (DMSO-$d_6$): d 8.00, 7.95 (2×s, 2, 7-H and 4-H), 5.90 (d, 1, 1'-H, $J_{1'-2}$=7.5 Hz), 5.58 (d, 1, 2'-OH, $J_{2'-2'OH}$=6.5 Hz), 5.46 (d, 1, 3'-OH, $J_{3'-3'OH}$=4.5 Hz), 4.44 (dd, 1, 5=-H, $J_{5'-4}$=4.5 Hz, $J_{5'-5}$=12.5 Hz), 4.43 (m, 1,2'-H, $J_{2'-3}$=6.0 Hz), 4.24 (dd, 1,5"-H, $J_{5"-4}$=2.0 Hz), 4.16 (m, 1, 4'-H, $J_{3'-4}$=3.0 Hz), 4.11 (m, 1, 3'-H), 2.15 (s, 3, 5'-OAc). $^{13}C$ NMR (DMSO-$d_6$): d 169.96 ($COCH_3$), 142.57 (C3a), 132.49, 132.42 (C2 and C7a), 125.78, 125.74 (C5 and C6), 120.14 (C4), 113.28 (C7), 90.32 (C1'), 82.56 (C4"), 71.27 (C2"), 68.99 (C3'), 63.34 (C5'), 20.58 ($COCH_3$). Anal. Calcd. for $C_{14}H_{13}BrCl_2N_2O_5$: C, 38.21; H, 2.98; N, 6.37. Found: C, 38.37; H, 2.86; N; 6.27.

5,6-Dichloro-1-(β-D-ribofuranosyl)benzimidazol-2-thione (53)

A mixture of dry 5,6-dichlorobenzimidazole-2-thione (3, 2.19 g 10 mmole), hexamethyldisilazane (4 ml) and ($NH_4$)$_2SO_4$ (0.1 g) was heated at reflux temperature with stirring for 15 hr under anhydrous conditions. The clear brown reaction mixture was fractionated to remove unreacted HMDS under reduced pressure (water aspirator) to afford the disilylated compound. The silylated compound was mixed with 1-bromo-2,3,5-tri-O-acetyl-D-ribofuranose (from 3.5 g (11 mmole) of tetraacetylsugar) and sodium iodide (0.05 g). The mixture was then fused at 110° C. (oil bath temperature) with stirring for 45 minutes under reduced pressure. The reaction mixture which had been cooled to room temperature was dissolved in $CHCl_3$. The $CHCl_3$ solution was washed with a cold saturated aqueous sodium bicarbonate solution (100 ml×4) and then cold water (100 ml×4). The $CHCl_3$ phase was dried over $Na_2SO_4$ and evaporated on a water bath (40° C.) to dryness to yield a syrup [5,6-dichloro-1-(2,3,5-tri-O-acetyl-β-D-ribofuranosyl) benzimidazole-2-thione]. The syrup was dissolved in methanolic ammonia (methanol saturated with ammonia at 0° C., 100 ml) and allowed to stand at room temperature for 24 hours. After the methanolic ammonia had been removed at room temperature, a syrup remained which was triturated with cold water (30 ml). The solid material (2.548 g) which separated was collected by filtration and was applied to a flash column chromatography on silica gel with $CH_2Cl_2$-MeOH (15:1) as eluant. Fractions were collected (25 ml each), and fractions containing the desired compound were combined and evaporated to obtain 53 which was crystallized from aq. EtOH. Overall yield 2.0 g, 57.0%, mp 241° C.

2-Benzylthio-5,6-dichloro-1-(β-D-ribofuranosyl) benzimidazole (54)

Compound 53 (0.5 g) was dissolved in cold water (10 ml) containing concentrated ammonium hydroxide (2.5 ml). Benzyl chloride (0.5 ml) was added to this solution with stirring and the stirring continued at room temperature for 5 hours. The white solid (0.41 g) which had separated from solution was collected by filtration, washed with cold water. The solid was extracted with ethyl acetate (100 ml) and the ethyl acetate phase was dried over anhydrous $Na_2SO_4$ and then evaporated by aspirator to give a syrup. The syrup was subjected to a flash column of silica gel with $CH_2Cl_2$-MeOH (15:1) as eluant. Fractions were collected (25 ml each) and fractions conbining the desired compound were combined and evaporated to afford 54 which was crystallized from $CH_2Cl_2$-MeOH (15:1), mp. 149° C., Yield 0.223 g (35.5%).

2-Chloro-5,6-dibromo-1-(2,3,5-tri-O-acetyl-β-D-ribofuranosyl)benzimidazole (56) and 2-Chloro-5,6-dibromo-1-(2,3,5-tri-O-acetyl-α-D-ribofuranosyl)benzimidazole A suspension of 931 mg (3 mmole) of 2-chloro-5,6-dibromobenzimidazole (17) in 15 ml of dry $CH_3CN$ was treated with 0.8 mL (3 mmole) of N,O-bis(trimethylsilyl)trifluoroacetamide (BSTFA) at 75° C. for 10 min to give a clear solution. To this solution, was added 955 mg (3 mmole) of 1,2,3,5-tetra-O-acetyl-β-D-ribofuranose and 0.64 mL (3.3 mmole) of trimethylsilyl triflate (TMSTf). Stirring was continued at 75° C. for 1 hr. The reaction mixture was cooled to room temperature and then diluted with 100 mL of EtOAc. The EtOAc solution was washed with a sat. $NaHCO_3$ solution (100 mL×2), sat. NaCl solution (100 mL), dried ($Na_2SO_4$), and evaporated. The residue was chromatographed on a silica column (3×20 cm, eluted with $CHCl_3$). Evaporation of fractions 4–10 and recrystallization of the residue from MeOH gave 946 mg (56%) of 56 as white crystals. mp 140°–142° C.; MS m/e 565.9082 (0.9%, $M^+$=565.9091); $^1H$ NMR (DMSO-$d_6$) d 8.20 (s, 1,7-H), 8.11 (s, 1, 4-H), 6.25 (d, 1, 1'-H), 5.55 (t, 1, 2'-H), 5.43 (dd, 1,3'-H), 4.47 (m, 2, 5'-H, 4'-H), 4.37 (m, 1, 5"-H), 2.15, 2.14, 2.02 (3×s, 3×, 3.3×Ac). Evaporation of fractions 13–15 gave 392 mg (23%) of the a anomer as a white foam. $^1H$ NMR (DMSO-$d_6$) d 8.07, 8.06 (2×s, 2, 4-H, 7-H), 6.70 (d, 1, 1'-H), 5.71 (t, 1, 2'-H), 5.50 (dd, 1, 3'-H), 4'-H), 4.36 (dd, 1, 5'-H), 427 (dd, 1, 5"-H).

2-chloro-5,6-dibromo-1-(β-D-ribofuranosyl)benzimidazole (57)

Method A (57)

A solution of 569 mg (1 mmole) of (56) in 20 mL of $NH_3$/MeOH was stirred in a sealed flask at room temperature for 5 hr. Volatile materials were removed by evaporation. The residue was recrystallized from MeOH to give 337 mg (2 crops, 76%) of 57. Its $^1H$ NMR spectrum was Identical to that of (57) prepared by a direct bromination; see Method B.

Method B (57)

To a suspension. of 570 mg (2 mmole) of 2-chloro-1-(β-D-ribofuranosyl)-benzimidazole in 50 mL of $H_2O$, was added dropwise 50 mL of $Br_2/H_2O$ over a period of 30 min. The reaction mixture was stirred at room temperature for an additional 3 hr. (Though the reaction mixture remained as a suspension, the shape of the crystals changed and TLC indicated a clean reaction). The reaction mixture was allowed to stand in an ice bath for 30 min. and then filtered. The solid was washed with portions of $H_2O$ until the washings were neutral. This solid was air dried and recrystallized from MeOH to give 757 mg of product (57) (80%) as white crystalline needles. MP 126°–129° C.; MS (FAB) m/e 440.8862 (3%, $MH^+$=440.8852); $^1H$ NMR (DMSO-$d_6$) d 8.68 (s, 1, 7-H) 8.09 (s, 1, 4-H), 5.88 (d, 1, 1'-H), 5.51 (d, 1, 2'-OH), 5.40 (t, 1, 5'-OH ), 5.30 (d,l, 3'-OH), 4.42 (m, 1, 2'-H), 4.14 (m, 1, 3'-H), 4.01 (m, 1, 4'-H), 3.70 m, 2, 5'-H).

2-Chloro-5,6-difluoro-1-(2,3,5-tri-O-acetyl-β-D-ribofuranosyl)benzimidazole (64) and 2-Chloro-5,6-difluoro-1-(2,3,5-tri-O-acetyl-α-D-ribofuranosyl)benzimidazole To a suspension of 0.943 g (5 mmole) of 12 in 25 mL of $ClCH_2CH_2Cl$, was added 1.25 mL (5 mmole) of BSA at 75° C. The reaction mixture was stirred at 75° C. for 30 min. To this solution, was added 1.75 g (5.5 mmole) of 1,2,3,5-tetra-O-acetyl-β-D-ribofuranose and 1.07 mL (5.5 mmole) of TMSOTf. Stirring was continued at 75° C. for 30 min. The reaction mixture was cooled to room temperature, diluted with 100 mL of $CHCl_3$, and extracted with sat. $NaHCO_3$ solution (100 mL×2) and sat. NaCl solution (100 mL). The $CHCl_3$ phase was dried ($Na_2SO_4$) and evaporated. The residue was chromatographed on a silica column (3×25 cm, eluted successively with 0.5%, 1% MeOH/$CHCl_3$). Evaporation of the appropriate fractions and recrystallization of the residue from MeOH gave 1.257 g (3 crops, 56%) of 64 as crystalline needles. MP 90°–91° C.; MS m/e 446.0694 (5%, $M^+$=446.0692); $^1H$ NMR (DMSO-$d_6$) d 7.93 (dd, 1, 7-H, $^3J_{F-H}$=10.5 Hz, $^4J_{F-H}$=7.5 Hz), 7.82 (dd, 1, 4-H, $^3J_{F-H}$=10.5 Hz, $^4J_{F-H}$=7.5 Hz), 6.23 (d, 1, 1'-H, $J_{1'-2'}$=7.0 Hz), 5.55 (t, 1,2'-H, $J_{2'-3'}$=7.0 Hz), 5.44 (m, 1, 3'-H, $J_{3-4}$=4.5 Hz), 4.45 (m, 3, 4'-H and 5'-H), 2.13, 2.10, 2.02 (3×s, 9, 3×Ac); $^{13}C$ NMR (DMSO-$d_6$) d 169.95, 169.50, 169.18 (3×OCOCH$_3$), 148.76, 148.62, 148..10, 148.93 (C5 and C6, $^1J_{F-C}$=242 Hz), 140.16 (C2), 137.01 (C3a, $^3J_{F-C}$=12 Hz), 128;54 (c7a, $^3J_{F-C}$=12 Hz), 107.31 107.09 (C4, $J_{F-C}$=20 Hz), 100.93, 100.66 (C7, $J_{F-C}$=24 Hz), 86.89 (Cl'), 79.41 (C4'), 70.40 (C2'), 68.62 (C3'), 62.67 (C5'), 20.48, 20.28, 20.00 (3×OCOCH$_3$).

Further elution and evaporation of the appropriate fractions gave 0.456 g (20%) of the a anomer as a syrup. MS m/e 446.0680 (12%, $M^+$=446.0692); $^1H$ NMR (DMSO-$d_6$): d 7.75 (m, 2, 7-H and 4-H), 6.69 (d, 1, 1'-H, $J_{1'-2'}$=4.0 Hz), 5.69 (t, 1, 2'-H, $J_{2'-3'}$=5.0 Hz), 5.49 (dd, 1, 3'-H, $J_{3'-4'}$=7.0 Hz), 4.90 (m, 1, 4'-H), 4.37 (dd, 1, 5'-H, $J_{5'-4'}$=3.5 Hz, $J_{5'-5'}$=12.0 Hz), 4.26 (dd, 1, 5"-H, $J_{5'-4}$=5.5 Hz), 2.09, 2.03, 1.54 (3's, 9, 3×Ac); $^{13}C$ NMR (DMSO-$d_6$): d 170.03, 169.27, 168.34 (3×OCOCH$_3$), 148.54, 148.37, 148.19, 145.88, 145.71, 145.54 (C5 and C6, $^1J_{F-C}$=241 Hz, $^2J_{F-C}$=16 Hz), 139.68 (C2), 136.71 136.58 (C3a, $^3J_{F-C}$=11 Hz), 129.45, 129.32 (C7a, $^3J_{F-C}$=12 Hz), 106.66, 106.44 (C4, $^2J_{F-C}$=20 Hz), 101.79, 101.52 (C7, $^2J_{F-C}$=24 Hz), 86.43 (Cl'), 78.16 (C4"), 70.97 (C2'), 70.39 (C3'), 62.69 (C5'), 20.49, 20.09, 19.48 (3×OCOCH$_3$).

2-Chloro-5,6-difluoro-1-(β-D-ribofuranosyl)benzimidazole (65)

Compound 64 (0.894 g, 2 mmole) was treated with 20 mL of $NH_3$/MeOH in a pressure bottle at room temperature for 3 hr. The reaction mixture was evaporated and coevaporated with MeOH to give a solid. This was recrystallized from MeOH to give 0.573 g (3 crops, 89%) of 65 as a crystalline compound. MP ~215° C. (dec.); MS m/e 320.0385 (20%, $M^+$=320.0375); $^1H$ NMR (DMSO-$d_6$): d 8.34 (dd, 1,7-H, $^3J_{F-H}$=11.5 Hz, $^4J_{F-H}$=7.5 Hz), 7.77 (dd, 1, 4-H, $^3J_{F-H}$=11.0 Hz, $J_{F-H}$=7.5 Hz), 5.88 (d, 1, 1'-H, $J_{1'-2}$=8.0 Hz), 5.50 (d, 1, 2'-OH, $J_{2-2-OH}$=6.5 Hz), 5.45 (t, 1, 5'-OH, $J_{5'-5'OH}$=4.5 Hz), 5.30 (d, 1, 3'-OH, $J_{3'-3'OH}$=4.5 Hz), 4.40 (m, 1,2'-H, $J_{2'-3}$=5.5Hz), 4.14 (m, 1, 3'-H, $J_{3'-4}$=1.5 Hz), 4.01 (m, 1, 4'-H), 3.72 (m, 2, 5'-H, $J_{5'-4}$=2.5 Hz, $J_{5'-5}$=12.0 Hz); $^{13}C$ NMR (DMSO-$d_6$): d 148.53, 148.42, 148.37, 148.26, 148.88, 145.76, 145.72, 145.60 (C5 and C6, $^1J_{F-C}$=241 Hz, $^2J_{F-C}$=16 Hz ), 140.84 (C2), 137.16, 137.04 (C3a, $^3J_{F-C}$=11 Hz), 128.55, 128.42 (C7a, $^3J_{F-C}$=12 Hz), 106.77, 106.54 (C4, $^2J_{F-C}$=20 Hz), 102.12, 101.84 (C7, $^2J_{F-C}$=25 Hz), 89.10 (C1'), 86.39 (C4'), 71.55 (C2'), 69.81 (C3'), 6.12 (C5').

2,5-Dichloro-6-fluoro-1-(2,3,5-tri-O-acetyl-β-D-ribofuranosyl)benzimidazole (2,5-β-anomer) &2,6-Dichloro-5-fluoro-1-(2,3,5-tri-O-acetyl-β-D-ribofuranosyl)benzimidazole(2,6-β-anomer) and 2,5-Dichloro-6-fluoro-1-(2,3,5-tri-O-acetyl-α-D-ribofuranosyl) benzimidazole (2,5-α-anomer) & 2,6-Dichloro-5-fluoro-1-(2,3,5-tri-O-acetyl-α-D-ribofuranosyl)benzimidazole (2,6-α-anomer)

To a suspension of 0.410 g (2.0 mmol) of 12c in 10 mL of MeCN, was added 0.5 mL (2.0 mmol) of BSA. The reaction mixture was stirred at 75° C. for 10 min to give a clear solution. This solution was treated wtth 0.70 g (2.2 mmol) of 1,2,3,5-tetra-O-acetyl-β-D-ribofuranose and 0.464 mL (2.4 mmol) of TMSOTf at 75° C. for 30 min. The reaction mixture was cooled and diluted with EtOAc (50 mL). The EtOAc solution was washed with sat. NaHCO$_3$ solution (50 mL×2), sat. NaCl solution (50 mL), dried (Na$_2$SO$_4$), and evaporated. The residue was chromatographed on a silica column (2.4×20 cm, eluted with CHCl$_3$ and 0.5% MeOH/CHCl$_3$). Evaporation of fractions 21–32 (20 mL per fraction) and recrystallization from MeOH gave 0.438 g (47%) of the β-anomers (2,5-β-anomer and 2,6-β-anomer) as white crystals. MP: 117°–119° C. MS: (EI) m/e 462.0414 (7%, M$^+$=462.0397). $^1$H NMR (DMSO-d$_6$): d 8.03 [d, 0.4, 7-H (2,6-β-anomer), $^4J_{F-H}$=6.5 Hz], 7.96 [d, 0.6, 4-H (2,5-β-anomer), $^3J_{F-H}$=7.0 Hz], 7.62 [d, 0.6, 7-H (2,5-β-anomer), $^3J_{F-H}$=9.5 Hz], 7.80 [d, 0.4, 4-H (2,6-β-anomer), $^3J_{F-H}$=9.5 Hz], 6.25 [d, 0.4, 1'H (2,6-β-anomer), J$_{1'-2'}$=7.0 Hz], 6.24 [d, 0.6, 1'-H (2,5-β-anomer), J$_{1'-2'}$=7.0 Hz], 5.55[t, 0.4, 2'-H (2,6-β-anomer), J$_{2'-3'}$=7.0 Hz], 5.54 [t, 0.6, 2"-H (2,5-β-anomer), J$_{2'-3'}$=7.0 Hz], 5.45 [m, 1, 3'-H (2,5-β-anomer+2,6-β-anomer)], 4.45 [m, 3, 4'-H and 5'-H (2,5-β-anomer+2,6-β-anomer)], 2.14, 2.11, 2.02 [3×s, 9, 3×Ac (2,5-β-anomer+2,6-β-anomer)]. Anal. Calcd. for C$_{18}$H$_{17}$Cl$_2$FN$_2$O$_7$: C 46.67, H 3.70, N 6.05. Found: C 46.76, H 3.66, N 5.97.

Evaporation of fractions 35–36 (20 mL per fraction) gave 0.153 g (17%) of the α-anomers (2,5-α-anomer and 2,6-α-anomer) as a foam. MS: (EI) m/e. 462.0399 (9%, M$^+$=462.0397). $^1$H NMR (DMSO-d$_6$): d 7.88, 7.37 [2×two overlapping d, 2, 4-H and 7-H (2,5-α-anomer+2,6-α-anomer), $^3J_{F-H}$=9.5 Hz, $^4J_{F-H}$=7.0 Hz], 6.70 [2×d, 1, 1'-H (2,5-α-anomer+2,6-α-anomer), J$_{1'-2'}$=4.0 Hz], 5.70 [m, 1, 2'-H (2,5-α-anomer+2,6-α-anomer)], 5.50 [m, 1, 3'-H (2,5-α-anomer+2,6-α-anomer)], 4.88 [m, 1, 4'-H (2,5-α-anomer+2,6-α-anomer)], 4.37 [m, 1, 5'-H(2,5-α-anomer+2,6-α-anomer)], 4.27 [m, 1, 5"-H (2,5-α-anomer+2,6-α-anomer)], 2.090, 2.086, 2.043, 2.028, 1.548, 1.544 [6×s, 9, 3×Ac (2,5-α-anomer+2,6-α-anomer)].

2,5-Dichloro-6-fluoro-1-β-D-ribofuranosylbenzimidazole 65a (2,5) & 2,6-Dichloro-5-fluoro-1-β-D-ribofuranosylbenzimidazole 65a (2,6)

A solution of 0.323 g (0.50 mmol) of the β-anomers (2,5+2,6) in 10 mL of NH3/MeOH was stirred in a pressure bottle at room temperature for 5 h. Volatile materials were removed by evaporation and coevaporation with MeOH (3×, bath temperature<40° C). The resulting solid was recrystallized from MeOH to give 0.141 g (2 crops, 84%) of white crystals (65a (2,5+2,6)). MP: 170°–172° C. MS: (EI) m/e 336.0082 (14%, M$^+$=336.0080). $^1$H NMR (DMSO-d$_6$): d 8.49 [d, 0.4, 7-H (65a-2,6), $^4J_{F-H}$=7.0 Hz],8.31 [d, 0.6, 7-H (65a-2,5), $^3J_{F-H}$=10.0 Hz], 7.91 [d, 0.6, 4-H (65a-2,5), $^4J_{F-H}$=7.0 Hz], 7.74 [d, 0.4, 4-H (65a-2,6), $^3J_{F-H}$=9.5 Hz], 5.89 [d, 1, 1'-H (65a (2,5+2,6)), J$_{1'-2'}$=7.0 Hz], 5.50 [d, 1,2'-OH (65a (2,5+2,6)), J$_{2'-2'OH}$=6.5 Hz], 5.43 [2×overlapping t, 1, 5'-OH (65a(2,5+2,6)), J$_{5'-5'OH}$=4.5 Hz], 5.29 [d, 1, 3'-OH (65a (2,5+2,6)), J$_{3'-3'OH}$=4.5 Hz], 4.41 [m, 1, 2'-H (65a (2,5+2,6))], 4.14 [m, 1, 3'-H (65a (2,5+2,6))], 4.02 [m, 1 ,4'-H(65a(2,5+2,6))], 3.70 [m, 2, 5'-H (65a(2,5+2,6))]. Anal. Calcd. for C$_{12}$H$_{11}$Cl$_2$FN$_2$O$_4$: C, 42.75; H, 3.29; N, 8.31. Found: C, 42.81; H, 3.43; N, 8.16.

2,6-Dichloro-1-(2,3,5-tri-O-acetyl-β-D-ribofuranosyl)benzimidazole (66)

Method A (66) 6.24 grams (33.4 mmoles) of 35 was suspended in 150 ml of 1,2-dichloroethane while stirring. To this material at 80° C., 8.5 ml (33.4 mmoles) of BSA was added via a syringe to give a clear solution. To this solution were added 10.62 grams (33.4 mmoles) of 1,2,3,5-tetra-O-acetyl-β-D-ribofuranose and 7.0 ml (36.7 mmoles) of TMSOTf. The reaction mixture was allowed to stir at 80° C. for one hr. EtOAc (100 ml) was added to the reaction mixture. The EtOAc solution was extracted with saturated NaHCO$_3$ solution (300 ml×2), saturated NaCl solution (50 ml), dried (Na$_2$SO$_4$), and evaporated in vacuo. The resulting yellowish-brown syrup was dissolved in a minimum volume of chloroform and transferred to a silica column (30×3 cm). The column was eluted with CHCl$_3$ while ultimately increasing solvent polarity to 1% MeOH/CHCl$_3$. The first spot eluted from the column was collected and evaporated in vacuo to reveal an oily yellow residue. The syrup was coevaporated with EtOH (25 ml×2) to reveal a white precipitate. Recrystallization from MeOH afforded 4.47 grams (30.0%) of a mixture of the 2,5-dichloro and 2,6-dichloro isomers as colorless crystals. Fractional recrystallization yielded 2.815 grams (19%) of colorless crystalline 66. MP 154°-154° C. MS (EI) m/e 444.0492 (6%, M$^+$=444.0491). $^1$H NMR (DMSO-d$_6$): d 7.89 (d, 1,7-H, J$_{7-5}$=2.0 Hz), 7.68 (d, 1,4-H, J$_{4-5}$=8.5 Hz), 7.37 (dd, 1, 5-H), 6.25 (d, 1, 1'-H, J$_{1'-2'}$=7:0 Hz), 5.57 (t, 1, 2'-H, J$_{2'-3'}$=7.0 Hz), 5.44 (dd, 1, 3'-H, J$_{3'-4'}$=4.5 Hz), 4.47, 4.39 (2×m, 3, 4'-H and 5'-H), 2.15, 2.14. 2.02 (3×s, 9, 3×Ac). $^{13}$C NMR (DMSO-d$_6$): d 169.94, 169.48, 169.15 (3×OCOCH$_3$), 140.06 (C3a and C2), 133.48 (C7a), 128.34 (C6), 123.78 (C5), 120.52 (C4), 111.71 (C7), 86.65 (C1'), 79.40 (C4'), 70.35 (C2'), 68.64 (C3'), 62.58 (C5'), 20.65, 20.26, 19.97 (3×OCOCH$_3$).

Method B (66)

To a stirred mixture of 0.419 g (3.116 mmole) of CuCl$_2$ and 0.371 mL(2.807 mmole) of 90% t-BuONO in 5 mL of CH$_3$CN, was added dropwise a solution of 0.633 g (1.487 mmole) of 2-amino-6-chloro-1-(β-D-ribofuranosyl) benzimidazole in 3 mL of CH$_3$CN. After the addition, stirring was continued at room temperature for 2 hr. The reaction mixture was diluted with 60 mL of EtOAc. The EtOAc solution was washed with H$_2$O (50 mL), sat. NaHCO$_3$ solution (,50 mL×2), sat. NaCl solution (50 mL), dried (Na$_2$SO$_4$), and evaporated. The residue was chromatographed on a silica column (1.9×35 cm, eluted with CHCl$_3$). Evaporation of the appropriate fractions and recrystallization from MeOH gave 0.380 g (57%) of 66 as a white crystalline compound. MP 155°–157° C. MS (EI) m/e 444.0487 (7%,M$^+$=444.0491). $^1$H NMR (DMSO-d$_6$): d 7.89 (d, 1,7-H, J$_{7-5}$=2.0 Hz), 7.68 (d, 1,4-H, J$_{4-5}$=8.5 Hz), 7.37 (dd, 1, 5-H), 6.25 (d, 1, 1'H, J$_{1'-2'}$=7.0 Hz), 5.57 (t, 1, 2'-H, J$_{2'-3'}$=7.0 Hz), 5.45 (dd, 1, 3'-H, J$_{3'-4'}$=4.5 Hz), 4.47, 4.35 (2×m, 3, 4'-H and 5'-H), 2.15, 2.14, 2.02 (3×s, 9, 3×Ac). $^{13}$H NMR (DMSO-d$_6$) d 169.91, 169.45, 169.12 (3×OCOCH$_3$), 140.06, 140.02 (C3a and C2), 133.49 (C7a), 128.34 (C6), 123.78 (C5), 120.51 (C4), 111.69 (C7), 86.65 (C1'), 79.39 (C4'), 70.35 (C2'), 68.64 (C3'), 62.68 (C5=), 20.54, 20.25, 19.96 (3×OCOCH$_3$).

2,6-Dichloro-1-(β-D-ribofuranosyl)benzimidazole (67)

2,6-Dichloro-1-(2,3,5-tri-O-acetyl-β-D-ribofuranosyl) benzimidazole (66) (1.8 grams) was dissolved in methanolic ammonia (35 ml). The reaction material was stirred in a pressure bottle for 5 hours at room temperature. Volatile materials were evaporated in vacuo to provide a white powdery precipitate. This residue was recrystallized from MeOH to yield 561 mg (2 crops, 85%) of 67 as colorless needles. MP 162°–163° C. $^1$H NMR (DMSO-d$_6$): d 8.30 (d, 1, 7-H, J$_{7-5}$=2.0 Hz), 7.64 (d, 1, 4-H, J$_{4,5}$=8.5 Hz), 7.31 (dd, 1, 5-H), 5.89 (d, 1, 1'-H, J$_{1'-2'}$=8.0 Hz), 5.49 (d, 1, 2'-OH, J$_{2'-2'}$=6 5 Hz), 5.35 (t, 1, 5'-OH, J$_{5'-5'OH}$=5.0 Hz), 5.28 (d, 1,3'-OH, J$_{3'-3'OH}$=4.5 Hz), 4.46 (m, 1,2'-H, J$_{2'-3'}$=5.5 Hz), 4.14 (m, 1,3'-H, J$_{3'-4'}$=2.0 Hz), 4.00 (m, 1,4'-H, J$_{4'-5'}$=J$_{4'-5'}$=3.0 Hz), 3.70 (m, 2, 5'-H and 5"-H. J$^{5'-5'}$=12.0 Hz). $^{13}$C NMR (DMSO-d$_6$) d 140.72 (C2), 140.17 (C3a), 133.56 (C7a), 127.86 (C6), 123.23 (C5), 128.34 (C6), 120.03 (C4), 113.15 (C7), 89.00 (C1'), 86.26 (C4'), 71.37 (C2'), 69.72 (C3'), 61.12 (C5').

2,5-Dichloro-1-(2,3,5-tri-O-acetyl-β-D-ribofuranosyl)benzimidazole (72)

To a stirred mixture of 0.292 g (2.172 mmole) of CuCl$_2$ and 0.259 mL (1.960 mmole) of 90% t-BuONO in 4 mL of CH$_3$CN, was added dropwise a solution of 0.463 g (1.087 mmole) of 2-amino-5-chloro-1-(β-D-ribofuranosyl) benzimidazole in 2 mL of CH$_3$CN. After the addition, stirring was continued at room temperature for 2 hr. The reaction mixture was diluted with 50 mL of EtOAc. The EtOAc solution was washed with H$_2$O (50 mL), sat. NaHCO$_3$ solution (50 mL×2), sat. NaCl solution (50 mL), dried (Na$_2$SO$_4$), and evaporated. The residue was chromatographed on a silica column (2×15 cm, eluted with CHCl$_3$). Evaporation of the appropriate fractions and recWstallization from MeOH gave 0.265 g (55%) of 72 as a white crystalline compound. MP 98°–100° C. MS (EI) m/e 444.0487 (8%, M$^+$=444.0491). $^1$H NMR (DMSO-d$_6$): d 7.81 (d, 1, 7-H, J$_{7-6}$=9.0 Hz), 7.77 (d, 1, 4-H, J$_{4-6}$=2.0 Hz), 7.42 (dd, 1,6-H), 6.25 (d, 1, 1'-H, J$_{1'-2'}$=7.0 Hz), 5.57 (t, 1,2'-H, J$_{2'-3'}$=7.0 Hz), 5.42 (dd, 1, 3'-H, J$_{3-4'}$=5.0 Hz), 4.40 (m, 3, 4'-H and 5'-H), 2.13, 2.11, 2.02 (3×s, 9, 3×Ac). $^{13}$H NMR (DMSO-d$_6$): d 170.01, 169.52, 169.20 (3×OCOCH$_3$), 142.17 (C3a), 140.66 (C2), 131.73 (C7a), 127.94 (C5), 123.91 (C6), 118.80 (C4), 113.19 (C7), 86.88 (C1'), 79.26 (C4'), 70.46 (C2'), 68;73 (C3'), 52.68 (C5'), 20.52, 20.29, 20.01 (3×OCOCH$_3$).

2,5-Dichloro-1-(β-D-ribofuranosyl)benzimidazole (73)

A solution of 0.226.g (0.508 mmole) of 72 in 10 mL of NH$_3$/MeOH was stirred in a pressure bottle at room temperature for 5 hr. The reaction mixture was evaporated and coevaporatad with MeOH (3×) to give a solid. This solid was recrystallized from MeOH to give 0.136 g (76%, based on C$_{12}$H$_{12}$Cl$_2$N$_2$O$_4$ MeOH) of 73 as white crystals. MP 102°–150° C. (melted over a large range of temperature). MS (CI) m/e 319.0242 (37%, MH$^+$=319.0252). $^1$H NMR (OMSO-d$_6$): d 8.08 (d, 1, 7-H, J$_{7-6}$=9.0 Hz), 7.73 (d, 1, 4-H, J$_{4-6}$=2.0 Hz), 7.30 (dd, 1, 6-H), 5.89 (d, 1, 1'-H, J$_{1-2}$=8.0 Hz), 5.51 (d, 1, 2'-OH, J$_{2'-2'OH}$=6-5 Hz), 5.29 (d, 1, 3'-OH J$_{3'-3'}$OH=4.5 Hz),5.26 (t, 1, 5'-OH, J$_{5'-5'OH}$=5-0 Hz), 4.45 (m, 1, 2'-H, J$_{2'-3'}$=5.5 Hz), 4.12 (m, 1, 3'-H, J$_{3'-4'}$=2.0 Hz), 3.99 (m, 1, 4'-H, J$_{4'-5'}$=J$_{4'-5'}$=3.5 Hz), 3.69 (m, 2, 5'-H and 5'-H, J$_{5'-5'}$=12.0 Hz). $^{13}$C NMR (DMSO-d$_6$) d 142.36 (C3a), 141.40 (C2), 131.88 (C7a), 127.49 (C5), 123.32 (C6), 118.40 (C4), 114.51 (C7), 89.07 (C1'), 86.23 (C4'), 71.49 (C2'), 69.75 (C3'), 61.23 (C5').

2-Chloro-5-nitro-1-(2,3,5-tri-O-acetyl-β-D-ribofuranosyl)benzimidazole (74) and 2-Chloro-6-nitro-1-(2,3,5-tri-O-acetyl-β-D-ribofuranosyl)benzimidazole (75)

To a suspension of 3.952 g (20 mmole) of 19 in 100 mL of 1,2-dichloroethane was added 5 mL (20 mmole) of BSA. The reaction mixture was stirred at 75° C. for 15 min to give a clear solution. This solution was cooled to ¯202 C. and treated with 7.0 g (22 mmole) of 1,2,3,5-tetra-O-acetyl-b-D-ribofuranose and 4.638 mL (24 mmole) of TMSOTf at room temperature for 2 h. The reaction mixture was diluted with 200 mL of CHCl$_3$. The CHCl$_3$ solution was washed with sat. NaHCO$_3$ solution (200 mL×2), sat. NaCl solution (200 mL); dried (Na$_2$SO$_4$), and evaporated. The residue was chromatographed on a silica column (5×35 cm, eluted with CHCl$_3$ and 0.5% MeOH/CHCl$_3$). Evaporation of the appropriate fractions gave 6.50 g (71%, one spot on TLC) of 74 and 75 as a white foam. Fractional recrystailization of this foam (5 times from MeOH) give 1.59 g (17%) of the pure 6-nitro isomer 75. MP 127°–129° C. MS (EI) m/e 455.0750 (2%, M$^+$=455.0732). $^1$H NMR (DMSO-d$_6$): d 8.68 (d, 1, 7-H, J$_{7-5}$=2.0 Hz), 8.21 (dd, 1, 5-H, J$_{5,4}$=9.0 Hz), 7.88 (d, 1, 4-H), 6.41 (d, 1, 1'-H, J$_{1'-2'}$7.0 Hz), 5.68 (t, 1, 2'-H, J$_{2'-3'}$=7.0 Hz), 5.45 (dd, 1, 3'-H, J$_{3'-4'}$4.0 Hz), 4.50, 4.40 (2×m, 3, 4'-H and 5'-H), 2.15, 2.12, 2.03 (3×s,9, 3×Ac). $^{13}$C NMR (DMSO-d$_6$): d 170.12, 169.49, 169.25 (3×OCOCH$_3$), 145.60 (C3a), 143.96 (C2), 143.65 (C6), 132.46 (C7a). 119.65 (CA), 118.92 (C5), 108.47 (C7), 86.96 (C1'), 79.67 (C4'), 71.12 (C2'), 68.75 (C3'), 62.56 (C5'), 20.39, 20.31, 20.03 (3×OCOCH$_3$).

5-Amlno-2-chloro-1-(2,3,5-tri-O-acetyl-β-D-ribofuranosyl)-benzimidazole (76) and 6-Amino-2-chloro-1-(2,3,5-tri-O-acetyl-β-D-ribofuranosyl)benzimidazole (77)

A sample of the foam containing 14 and 15 (3.96 g, 8.688 mmole, one spot on TLC) was dissolved in 90 mL of EtOH and was hydrogenated at room temperature, 50 psi for 1 day using ¯0.30 g of Raney Nickel as catalyst (the reaction was monitored by TLC). The reaction mixture was then filtered and the filtrate was evaporated. The residue was chromatographed on a silica column (5×45 cm, eluted with 0.5% MeOH/CHCl$_3$). Evaporation of the appropriate fractions gave 1.54 g (42%) of 77 as a white foam. MS (EI) m/e 425.0987 (14%, M$^+$=425.0990). $^1$H NMR (DMSO-d$_6$): d 7.29 (d, 1,4-H, J$_{4-5}$=8.5 Hz), 6.75 (d, 1, 7-H, J$_{7,5}$=1.5 Hz), 6.61 (dd, 1, 5-H), 6.09 (d, 1, 1'-H, J$_{1'-2'}$=6.5 Hz), 5.57 (t, 1, 2'-H, J$_{2'-3'}$=7-5 Hz), 5.37 (dd, 1,3'-H, J$_{3'-4'}$=5.5 Hz), 5.19 (s, 2, 6-NH$_2$). 4.43 (dd, 1.5'-H, J$_{5'-4}$=2.5 Hz, J$_{5'-5'}$=11.0 Hz), 4.40 (m, 1, 4'-H), 4.36 (dd, 1, 5'-H, J$_{5'-4}$=2.09, 2.04 (3×s, 9, 3×Ac). $^{13}$C NMR (DMSO-d$_6$): d 170.10, 169.45, 169.19 (3×OCOCH$_3$), 146.03 (C6), 134.83 (C2), 134.06 (C7a), 132.92 (C3a), 119.35 (CA), 112.17 (C5), 94.72 (C7), 86.67 (C1'), 78:46 (C4'), 69.75 (C2'), 68.58 (C3'), 62.51 (C5'), 20.50, 20.21, 19.99 (3×OCOCH$_3$).

Further elution and evaporation of the appropriate fractions gave 1.86 g (50%) of 76 as a White foam. MS (EI) m/e 425.0976 (9%, M$^+$=425.0990). $^1$H NMR (DMSO-d$_6$): d 7.40 (d, 1,7-H, J$_{7,6}$=8.5 Hz), 6.76 (d, 1,4-H, J$_{4,6}$=2.0 Hz), 6.66

(dd, 1,6-H), 6.10 (d, 1, 1'-H, $J_{1'-2'}$=6.5 Hz), 5.56 (t, 1,2'-H, $J_{2'-3'}$=7.0 Hz), 5.39 (dd, 1, 3'-H, $J_{3'-4'}$=5.0 Hz), 5.10 (br. s, 2, 5-NH$_2$), 4.40 (m, 3, 4'-H and 5'-H), 2.13, 2.10, 2.02 (3×s, 9, 3×Ac). $^{13}$C NMR (DMSO-d$_6$): d 169.91,169.52, 169.11 (3×OCOCH$_3$), 145.31 (C5), 142.74 (C3a), 137.80 (C2), 124.66 (C7a), 112.50 (C6), 111.62 (C7), 102.23 (C4), 86.57 (C1'),78.89 (C4'), 70.05 (C2'), 68.78 (C3'), 62.69 (C5'), 20.45, 20.26, 19.98 (3×OCOCH$_3$).

5-Amino-2-chloro-1-(β-D-ribofuranosyl) benzimidazole (78)

A solution of 0.363 g (0.852 mmole) of 76 in 10 mL of NH$_3$/MeOH was stirred in a pressure bottle at room temperature for 5 hr. The reaction mixture was evaporated and coevaporated with MeOH (3×, bath temperature <40° C. The residue was recrystallized from MeOH/Et$_2$O to give 0.203 g (2 crops, 79%) of 18 as beige crystals. MP ~154° C. (dec.). MS (EI) m/e 299.0675 (1096, M$^+$=299.0673). $^1$H NMR (DMSO-d$_6$): d 7.56 (d, 1, 7-H, $J_{7-6}$=8.5 Hz), 6.73 (d, 1,4-H, $J_{4-6}$=2.0 Hz), 6.57 (dd, 1,6-H), 5.77 (d, 1,1'-H, $J_{1'-2}$=7 5 Hz), 5.39 (d, 1, 2'-OH, $J_{2'-2'OH}$=6.5 Hz), 5.18 (d, 1, 3'-OH, $J_{3'-3'OH}$=4.5 Hz), 5.11 (t, 1, 5'-OH, $J_{5'-5'OH}$=5.0 Hz), 4.90 (s, 2, 5-NH$_2$), 4.44 (m, 1, 2'-H, $J_{2'-3'}$=6.0 Hz 3'-H, $J_{3'-4'}$2.5 Hz), 3.91 (m, 1, 4'-H, $J_{4'-5'}$=3.5 Hz), 3.65 ("t", 2, 5'-H). $^{13}$C NMR (DMSO-d$_6$): d 144.82 (C5), 142.77 (C3a), 138.25 (C2), 125.13 (C7a), 112.67 (C7), 112.22 (C6), 101.88 (C4), 88.81 (C1'), 85.48 (C4'), 70.89 (C2'), 69.61 (C3'), 61.31 (C5').

6-Amino-2-chloro-1-β-D-ribofuranosyl) benzimidazole (79)

A solution of 0.283 g (0.665 mmole) of 77 in 10 mL of NH$_3$/MeOH was stirred in a pressure bottle at room temperature for 5 hr. The reaction mixture was evaporated and coevaporated with MeOH (3×, bath temperature <40° C.). The residue was recrystallized from MeOH to give 0.170 g (2 crops, 85%) of 19 as beige crystals. MP ~170° C. (dec.). MS (EI) m/e 299.0862 (16%, M$^+$=299.0673). $^1$H NMR (DMSO-d$_6$): d 7.25 (d, 1, 4-H, $J_{4-5}$=8.5 Hz), 6.87 (d., 1, 7-H, $J_{7-5}$=2.0 Hz), 6.57 (dd, 1, 5-H), 5.75 (d, 1, 1'-H, $J_{1'-2}$=7 5 Hz), 5.43 (d, 1,2'-OH, $J_{2'-2'OH}$=6-5 Hz), 5.18 (d, 1, 3'-OH, $J_{3'-3'OH}$=5.0 Hz), 5.04 (s, 2, 6-NH$_2$), 5.03 (t, 1,5'-OH, $J_{5'-5'OH}$=5.5 Hz), 4.48 (m, 1, 2'-H, $J_{2'-3'}$=6.0 Hz), 4.07 (m, 1,3'-H, $J_{3'-4'}$=3.0 Hz), 3.90 (m, 1, 4'-H, $J_{4'-5}$=4.0 Hz, $J_{4'-5}$= 5.0 Hz), 3.66 (m, 2, 5'-H and 5"-H, $J_{4'-5''}$=12.0 Hz). $^{13}$C NMR (DMSO-d$_6$): d 145.34 (C6), 135.63 (C2), 134.34 (C7a), 133.18 (C3a), 118.83 (C4), 111.71 (C5), 95.79 (C7), 88.79 (C1'), 85.24 (C4'), 70.17 (C2'), 69.70 (C3'), 61.55 (C5").

4,6-Dichloro-2-trifluoromethyl-1-(2,3,5-tri-O-acetyl-1-β-D-ribofuranosyl)benzimidazole(81a)

A mixture of 4,6-dichloro-2-trifluoromethylbenzimidazole (28a, 0.99 g, 3.4 mmole) and 1,2,3,5-tetra-O-acetyl-β-D-ribofuranose (1.71 g, 5.36 mmole) was heated at 170° C. for 1.5 hr under reduced pressure. The resulting mixture was dissolved in 20 mL of CHCl$_3$ and was chromatographed on a SiO$_2$ column, (2×20 cm). Elution of the column with hexane:EtOAc (80:20, v/v) and evaporation of appropriate fraction gave 0.67 gm (34%) of 81a: m.p. 116°–120° C.; $^1$H NMR (DMSO-d$_6$): d 8.00 (d, $^1$H, J=1.6 Hz, 7H), 7.74 (d, 1H, J=1.5 Hz, 5H), 6.15 (d, 1H, $J_{1'-2}$=6.8 Hz, 1'H), 5.53 (t, 1H, $J_{2'-3}$=6.7 Hz, 2'H), 5.49-5.45 (m, 1H, 3'H), 4.56-4.53 (m, 2H, 4'H and 5'H), 4.37-4.33 (m, 2H, 5"H), 2.15, 2.12, 1.92 (3s, 9H, 3×Ac).

4,6-Dichloro-2-trifluoromethyl-1-(β-D-ribofuranosyl)benzimidazole (81b)

A mixture of 81a (0.57 g, 1.1 mmole) and MeOH-NH$_3$ (20 mL) were stirred at room temperature for 10 hr. The excess of MeOH and NH$_3$, was removed under reduced pressure. The product thus obtained was chromatographed over SiO$_2$ column (2×14 cm) (230–400 mesh). Elution of the column with CHCl$_3$:MeOH (98:2, v/v) the product which was crystallized from the mixture of MeOH-H$_2$O to give 0.268 g (62.4%) of 81 b: m.p. 162° C.; $^1$H NMR (DMSO-d$_6$): d 8.59 (d, 1H, J=1.7 Hz, 7H), 7.68 (d, 1H, J=1.7 Hz, 5H), 5.82 (d, 1H, $J_{1-2}$=7.62 Hz, 1'H), 5.50-5.47 (m, 2H, exchanges with D$_2$O, 2'OH and 5'OH), 5.29 (d, 1H, exchanges with D$_2$O), 4.41 (q, 1H, $J_{2'3}$=6.06 Hz, 2'H ), 4.16 (bs, 1H, 3'H), 4.04 (bs, 1H, 4'H), 3.75 (m, 2H, S'H and 5"H). Anal. Calcd. for (C$_{13}$H$_{11}$N$_2$O$_4$F$_3$Cl$_2$): C, 40.33; H, 268; N, 7.23; Found: C, 40.02; H, 2.66; N, 6.74.

2,4-Dichloro-1-(2,3,5-tri-O-benzyl-β-D-ribofuranosyl)-6-trifluoromethylbenzimidazole and 2,4-Dichloro-1-(2,3,5-tri-O-benzyl-α-D-ribofuranosyl)-6-trifluoromethylbenzimidazole For the preparation of 1-O-chloro-2,3,5-tri-O-benzyl-D-ribofuranose, HCl gas was allowed to pass through a solution of 1-O-p-nitrobenzoyl-2,3,5-tri-O-benzyl-β-D-ribofuranose (0.774 g, 1.36 mmol) in 5 mL of dry CH$_2$Cl$_2$ at 0° C. for 15 min. The resulting suspension was quickly filtered and the filtrate was evaporated. The residue was coevaporated with MeCN and then dissolved in 5 mL of dry MeCN for immediate use in the subsequent glycosylation reaction.

To a mixture of 0.289 g (1.133 mmol) of 41c in 5 mL of MeCN, was added 0.283 mL (1.133 mmol) of BSA. The reaction mixture was stirred at 80° C. for 25 min. This solution was reacted with the above MeCN solution of the carbohydrate and 0.285 mL mL (1.133 mmol) of BSA. The reaction mixture was stirred at 80° C. for 25 min. This with EtOAc (60 mL). The EtOAc solution was washed with sat. NaHCO$_3$ solution (50 mL (1.473 mmol) of TMSOTf at 80° C. for 30 min. The reaction mixture was cooled and diluted with EtOAc (60 mL). The EtOAc solution was washed with sat. NaHCO$_3$ solution (50 mL×2); sat. NaCl solution (50 mL), dried (Na$_2$SO$_4$), and evaporated. The residue was the α-anomer as a syrup. MS: (Cl) m/e 657.1561 (1%, MH+= 657.1535). 1H NMR EtOAc/hexane). Evaporation of fractions 20–26 (20 mL per fraction) gave 0.31 g (42%) of the β-anomer as a syrup. MS: (Cl) m/e 657.1561 (1%, MH$^+$= 657.1535). $^1$H NMR (DMSO-d$_6$): d 8.05(s, 1,7-H),7.69(s, 1, 5-H),7.35, 6.95 (2×m, 15, 3×Ph),6.08(d, 1, 1'-H, $J_{1'-2}$=8.0 Hz), 4.73 ~4.24 (m, 9, 2'-H, 3'-H, 4'-H, and 3×PhCH$_2$), 3.75 (dd, 1, 5'-H, $J_{4'-5}$=2.0 Hz, $J_{5'-5}$=11.0 Hz), 3.58 (dd, 1, 5"-H, $J_{4'-5}$=3.0 Hz).

Evaporation of fractions 34–41 (20 mL per fraction) gave 0.262 g (35%) of the a-anomer as a syrup. MS: (Cl) m/e 657.1517 (1%, MH$^+$=657.1535). $^1$H NMR (DMSO-d$_6$): d 7.94 (s, 1, 7-H), 7.66 (s, 1, 5-H), 7.30, 7.08, 6.72 (3×m, 15, 3×Ph), 6.51 (d, 1, 1'-H, $J_{1'-2}$=4.5 Hz), 4.69 ~4.07 (m, 9, 2'H, 3'-H, 4'-H, and 3×PhCH$_2$), 3.73 (dd, 1, 5'-H, $J_{4'-5}$=2.5 Hz, $J_{5'-5}$=11.0 Hz), 3.62 (dd, 1, 5"-H, $J_{4'-5}$=4.5 Hz).

2,4-Dichloro-1-(β-D-ribofuranosyl)-6-trifluoromethylbenzimidazole (81c)

To a solution of 0.29 g (0.441 mmol) of the β-anomer (see previous prep.) in 6 mL of CH$_2$Cl$_2$, was added dropwise 4.41 mL of 1M BCl$_3$ at –78° C. The reaction mixture was stirred at –78° C. for 2 hr and then at –40° C. for 2 hr MeOH (3 mL) was added and stirring was continued at –40° C. for 10 min. The reaction mixture was diluted with EtOAc (50 mL). The EtOAc solution was washed with H$_2$O (50 mL), sat. NaHCO$_3$ solution (50 mL), sat. of CHCl$_3$ and dded in vacuo to give 0.146 g (86%) of 81% as a white solid. MS: (EI) m/e a small mount of CHCl₃ and then filtered. The solid product was washed with portions of CHCl₃ and dried in vacuo to give 0.146 g (86%) of 81c as a white solid. MS: (EI) m/e 386.0038 (14%, M⁺=386.0048). $^1$H NMR (DMSO-d₆): d 8.75 (s, 1, 7-H), 7.76 (s, 1, 5-H), 5.97 (d, 1, 1'-H, $J_{1'-2'}$=8.0 Hz), 5.55 (d, 1, 2'-OH, $J_{2'-2'OH}$=6.0 Hz), 5.43 (t, 1, 5'-OH, $J_{5'-5'OH}$=4.5 Hz), 5.35 (d, 1,3'-OH, $J_{3'-3'OH}$=4.5 Hz), 4.43 (m, 1,2'-H, $J_{2'-3}$=5.5 Hz), 4.15 (m, 1, 3'-H, $J_{3'-4}$=1.5 Hz), 4.06 (m, 1, 4'-H, $J_{4'-5'}=J_{4'-5''}$=2.5 Hz), 3.69 (m, 2, 5'-H and 5''-H).

2-Chloro-4,5-dibromo-1-(2,3,5-tri-O-acetyl-β-D-ribofuranosyl)benzimidazole (84) and 2-Chloro-5-bromo-1-(2,3,5-tri-O-acetyl-6-D-ribofuranosyl) benzimidazole (86)

To a stirred mixture of 1.228 g (5.498 mmole) of CuBr₂ and 0.654 ml (4.949 mmole) of 90% t-BuONO in 10 mL of CH₃CN, was added dropwise a solution of 1.170 g (2.748 mmole) of 78 in 3 mL of Cl₃CN. After the addition, stirring was continued at room temperature for 2 hr. The reaction mixture was diluted with 100 mL of EtOAc. The EtOAc solution was washed with H₂O (100 mL), sat Na HCO₃ solution (100 mL×2), sat NaCl solution (100 mL), dried (Na₂SO₄), and evaporated. The residue was chromatographed on a silica column (4.1×30 cm, eluted with CHCl₃). Evaporation of fractions 59–78 (20 mL per fraction) and recrystallization for MeOH gave 0.600 g (38%) of 84 as a white solid. MP 202°–203° C. MS (EI) m/e 565.9109 (4%,M⁺=565.9091). $^1$H NMR (DMSO-d₆): d 7.74 (2×d, 2, 6-H and 7-H, $J_{6-7}$=8.5 Hz), 6.26 (d, 1, 1'-H, $J_{1'-2'}$=6.5 Hz), 5.53 (t, 1, 2'-H, $J_{2'-3}$=7.0 Hz), 5.42 (dd, 1,3'-H, $J_{3'-4}$=4.5 Hz), 4.42 (m, 3, 4'-H and 5'-H), 2.14, 2.11, 2.01 (3×s, 9, 3×Ac). $^{13}$C NMR (DMSO-d₆): d 169.92, 169.42, 169.14 (3×OCOCH₃), 141.56 (C3a), 140.91 (C2), 132.12 (C7a), 128.03 (C6), 118.58 (C5), 114.56 (C4), 112.60 (C7), 87.12 (C1'), 79.41 (C4'), 70.60 (C2'), 68.66 (C3'), 62.55 (C5'), 20.47, 20.22, 19.94 (3×OCOCH₃).

Evaporation of fractions 89–125 (20 mL per fraction) and recrystallization from MeOH gave 0.405 g (30%) of 86 as a white crystals. MP 129°–130° C. MS (EI) m/e 487.9973 (5%, M⁺=487.9968). $^1$H NMR (DMSO-d₆) d 7.91 (d, 1, 4-H, $J_{4-6}$=2.0 Hz), 7.76 (d, 1, 7-H, $J_{7-6}$=8.5 Hz), 7.53 (dd, 1,6-H), 6.25 (d, 1, 1'-H, $J_{1'-2}$=6.5 Hz), 5.56 (t, 1, 2'-H, $J_{2'-3}$=7.0 Hz), 5.42 (dd, 1, 3'-H, $J_{3'-4}$=5.0 Hz), 4.43 (m, 3, 4'-H and 5'-H), 2.14, 2.11, 2.02 (3×s, 9, 3×Ac). $^{13}$C NMR (DMSO-d₆): d 170.01, 169.52, 169.19 (3×OCOCH₃), 142.61 (C3a), 140.50 (C2), 132.05 (C7a), 126.51 (C6), 121.73 (C4), 115.71 (C5), 113.58 (C7), 86.87 (C1'), 79.26 (C4'), 70.44 (C2'), 68.73 (C3'), 62.64 (C5'), 20.53, 20.29, 20.01 (3×OCOCH₃).

5-Bromo-2-chloro-1-(β-D)-ribofuranosyl) benzimidazole (87)

A solution of 0.304 g (0.621 mmole) of 86 in 10 mL of NH₃/MeOH was stirred in a pressure bottle at room temperature for 5 h. The reaction mixture was evaporated and coevaporated with MeOH (3×, bath temperature <40° C.). The residue was recrystallized from MeOH to give 0.192 g (85%) of 87 as white crystals. MP 154°–155° C. MS (Cl) m/e 362.9735 (40%, MH⁺=362.9747). $^1$H NMR (DMSO-d₆): d 8.01 (d, 1, 7-H, $J_{7-6}$=8.5 Hz), 7.87-(d, 1,4-H, $J_{4-6}$=2.0 Hz), 7.41 (dd, 1, ,6-H), 5.89 (d, 1, 1'-H, $J_{1'-2}$=8.0 Hz), 5.51 (d, 1, 2'-OH, $J_{2'-2'-OH}$=6-5 Hz), 5.28 (d, 1,3'-OH, $J_{3'-3'-OH}$=4.5 Hz), 5.25 (t, 1,5'-OH, $J_{5'-5'OH}$=5.0 Hz), 4.44 (m, 1, 2'-H, $J_{2'-3}$=5.5 Hz), 4.13 (m, 1, 3'-H, $J_{3'-4}$=2.5 Hz), 3.98 (m, 1, 4'-H, $J_{4'-5'}=J_{4'-5''}$=3.5 Hz), 3.68 (m, 2, 5'-H and 5''-H, $J_{5'-5''}$=12.0 Hz). $^{13}$C NMR (DMSO-d₆): d 142.81 (C3a), 141.23 (C2), 132.20 (C7a), 125.92 (C6), 121.32 (C4), 115.27 (C5), 114.89 (C7), 89.05 (C1'), 86.21 (C4'), 71.47 (C2'), 69.73 (C3'), 61.22 (C5').

2-Chloro-6,7-dibromo-1-(2,3,5-tri-O-acetyl-6-D-ribofuranosyl)-benzimidazole (88) and 2-Chloro-6-bromo-1-(2,3,5-tri-O-acetyl-β-O-ribofuranosyl) benzimidazole (89)

To a stirred mixture of 0.564 g (2.525 mmole) of CuBr₂ and 0.300 mL (2.270 mmole) of 90% t-BuONO in 5 mL of CH₃CN, was added dropwise a solution of 0.538 g (1.263 mmole) of 77 in 3 mL of. CH₃CN. After the addition, stirring was continued at room temperature for 2 hr. The reaction mixture was diluted with 60 mL. of EtOAc. The EtOAc solution was washed with H₂O (50 mL), sat. NaHCO₃ solution (50 mL×2), sat. NaCl solution (50 mL), dried (Na₂SO₄), and evaporated. The residue was chromatographed on a silica column (1.9×45 cm, eluted with CHCl₃). Evaporation of fractions 11–22 (20 mL per fraction) and recrystallization from MeOH twice gave 0.198 g of 89 as white crystals. Evaporation of fractions 23–26 and recrystallization from MeOH gave 0.015 g of 88. The mother liquors were evaporated and the residue was rechromatographed on a silica column (1.9×45 cm, eluted with CHCl₃). Evaporation of fractions 24–34 and recrystallization from MeOH twice gave an additional 0.072 g of 89 as white crystals. Fractions 37–56 were evaporated and the residue was repurified by repeating the column chromatography. Evaporation of the appropriate fractions and recrystailization from MeOH gave an additional 0.070 g of 88 as white crystals. The total yield of 88 was 0.085 g (12%). MP 121°–122° C. MS (EI) m/e 565.9092 (1%, M⁺=565.9091). 1H NMR (DMSO-d₆): d 7.74 (d, 1, 5-H,, $J_{5-4}$=8.5 Hz), 7.65 (d, 1, 4-H), 7.25 ("br. s", 1, 1'-H), 5.80 (dd, 1,2'-H, $J_{2'-1}$=5.0 Hz, $J_{2'-3}$=7.5 Hz), 5.44 (t, 1, 3'-H, $J_{3'-4}$=7.5 Hz), 4.46 (dd, 1, 5'-H, $J_{5'-4}$=3.0 Hz, $J_{5'-5}$=12.0 Hz), 4.39 (m, 1, 4'-H), 4.29 (dd, 1, 5''-H, $J_{5'-4}$=6.0 Hz), 2.13, 2.08, 2.05 (3×s, 9, 3×Ac). $^{13}$C NMR (DMSO-d₆): d 169.97, 169.46, 169.33 (3×OCOCH₃), 141.51 (C3a), 141.09 (C2), 133.28 (C7a), 128.37 (C5), 121.92 (C6), 120.07 (C4), 105.20 (C7), 86.58 (C1'), 78.08 (C4'), 71.34 (C2'), 68.24 (C3'), 62.08 (C5'), 20.46, 20.08, 20.01 (3×OCOCH₃). The total yield of 89 was 0.270 g (44%). MP 169°–170° C. MS (EI) m/e 467.9973 (9%, M⁺=487.9986). $^1$H NMR (DMSO-d₆): d 8.01 (d, 1, 7-H, $J_{7,5}$=1.5 Hz), 7.63 (d, 1, 4-H $J_{4,5}$=8.5 Hz), 7.49 (m, 1, 5-H), 6.25 (d, 1, 1 '-H, $J_{1'-2}$=7.0 Hz), 5.57 (t, 1, 2'-H. $J_{2'-3}$=7.0 Hz), 5.44 (dd, 1, 3'-H, $J_{3'-4}$=4.5 Hz), 4.47, 4.39 (2×m, 3, 4'-H and 5'-H), 2.16, 2.14, 2.02 (3×s, 9, 3×Ac). $^{13}$C NMR (DMSO-d₆): d 169.99, 169.52, 169.19 (3×OCOCH₃), 140.38 (C3a), 139.68 (C2), 133.97 (C7a), 126.52 (C5), 120.91 (C4), 116.33 (C6), 114.50 (C7), 86.61 (C1'), 79.43 (C4'), 70.39 (C2'), 68.68 (C3'), 62.61 (C5'), 20.71, 20.31, 20.02 (3×OCOCH₃).

6-Bromo-2-chloro-1-(β-D-ribofuranosyl (benzimidazole (90)

A solution of 0.176 g (0.359 mmole) of 89 in 10 mL of NH₃/MeOH was stirred in a pressure bottle at roomtemperature for 5 hr. The reaction mixtures was evaporated and coevaporated wtth MeOH (3×, bath temperature <40° C.). The resulting solid was recrystallized from MeOH to give 0.097 g (2 crops, 74%) of 90 as white crystals. MP 152°–153° C. MS (EI) m/e 681.9685 (10%, M⁺=361.9669). $^1$H NMR (DMSO-d₆): d 8.43 (d, 1, 7-H, $J_{7,5}$=2.0 Hz), 7.59 (d, 1, 4-H, $J_{4,5}$=8.5 Hz), 7.43 (dd, 1, 5-H), 5.88 (d, 1, 1'-H, $J_{1'-2}$=8.0 Hz), 5.49 (d, 1,2'-OH, $J_{2'-2'OH}$=6.5 Hz), 5.34 (t, 1,5'-OH, J$_{5'-5'OH}$=4.5 Hz), 5.27 (d, 1, 3'-OH, J$_{3'-3'OH}$=4.5 HZ), 4.45 (m, 1,2'-H, J$_{2'-3'}$=5.5 Hz), 4.14, (m, 1,3'-H, J$_{3'-4'}$=2.0 Hz), 4.00 (m, 1,4'-H, J$_{4'-5}$J$_{4'-5}$=3.5 Hz), 3.70 (m, 2, 5'-H and 5'-H, J$_{5'-5}$"=12.0 Hz). $^{13}$C NMR (DMSO-d$_6$): d 140.70 (C2), 140.49 (C3a), 134.02 (C7a), 125.95 (C5), 120.46 (C4), 116.01 (C7), 115.87 (C6), 88.99 (C1'), 86.32 (C4'), 71.40 (C2'), 69.79 (C3'), 61.15 (C5').

1-1,2,3,5-Tri-O-benzyl-β-D-ribofuranosyl)-2,4,5,6-tetrachlorobenzimidazole (91a) and 1-(2,3,5-Tri-O-benzyl-α-ribofuranosyl)-2,4,5,6-tetrachlorobenzimidazole For the preparation of 1-O-chloro-2,3,5-tri-O-benzyl-D-ribofuranose, HCl gas was allowed to pass through a solution of 1-O-p-nitrobenzoyl-2,3,5-tri-O-benzyl-β-D-ribofuranose (1.479 g, 2.6 mmol) in 10 mL of dry CH$_2$Cl$_2$ at 0° C. for 15 min. The resulting suspension was quickly filtered and the filtrate was evaporated. The residue was coevaporated with dry MeCN and then dissolved in 5 mL of dry MeCN for immedate use in the subsequent glycosylation reaction. To a mixture of 13 (0.51 2 g, 2 mmol) in 10 mL of dry MeCN, was added 0.5 mL (2 mmol) of BSA. The reaction mixture was stirred at 75° C. for 20 min. This solution was treated with the above MeCN solution of the blocked carbohydrate and 0.464 mL (2.4 mmol) of TMSOTf at 70° C. for 20 min. The reaction mixture was cooled and diluted with EtOAc (,50 mL). The EtOAc solution was washed with sat. NaHCO$_3$ solution (50 mL×2), sat. NaCl solution (,50 mL), dried (Na$_2$SO$_4$), and evaporated. The residue was chromatographed on a silica column (1.9×38 cm, eluted with hexane, 10%, 15% EtOAc/hexane). Evaporation of fractions 30–37 (15 mL per fraction) gave 0.593 g (45%) of 91 a as a colorless syrup. MS: (EI) m/e 658.0780 (2%, M$^+$=658.0774). $^1$H NMR (DMSO-d$_6$): d 7.93 (s, 1, 7-H), 7.35, 6.92 (2×m, 15, 3×PhCH$_2$), 5.99 (d, 1, 1'-H, J$_{1'-2}$=8.0 Hz), 4.72, 4.58, 4.35 (3×m, 9, 2'-H, 3'-H, 4'-H, and 3×PhCH$_2$), 3.76 (dd, 1, 5'-H, J$_{4'-5'}$=2.0 Hz, J$_{5'-5''}$=11.0 Hz), 3.65 (dd, 1, 5"-H, J$_{4'-5''}$=2.5 Hz). $^{13}$C NMR (DMSO-d$_6$): d 142.00 (C2), 138.40 (C3a),137.81,137.44, 136.74 (3×PhCH$_2$), 131.34 (C7a), 128.08, 128.08, 127.58, 127.40, 127.32, 127.28, 126.97 (3×PhCH$_2$ and G4), 124.64, 122.52 (C5 and C6), 112.65 (C7), 87.46 (C1'), 83.03, 77.08, 74.92 (C2', C3', and C4'), 72.43, 71.44, 71.26 (3×PhCH$_2$), 69.22 (C5').

Evaporation of fractions 44–68 (15 mL per fraction) gave 0.69 g of the α-anomer as a syrup. This sample contained a small amount of the startign material (13) and was further purified on a silica column (1.9×16 cm, eluted with CHCl$_3$, 0.5% MeOH/CHCl$_3$). Evaporation of fractions 5–10 (15 mL per fraction) gave 0.619 g (47%) of the α-anomer as a syrup. MS: (EI) m/e 658.0781 (1%, M$^+$=658.0774). $^1$H NMR (DMSO-d$_6$): d 7.82 (s, 1, 7-H), 7.32, 7.15, 6.77 (3×m, 15, 3×PhCH$_2$), 6.42 (d, 1, 1'-H, J$_{1'-2}$=4.5 Hz), 4.58, 4.34, 4.13 (m, t, d, 9, 2'-H, 3'-H, 4'-H, and 3×PhCH$_2$), 3.68 (m, 2, 5'-H and 5'-H, J$_{5'-5''}$=11.0 Hz). $^{13}$C NMR (DMSO-d$_6$): d 141.18 (C2), 138.16, 137.89, 137.43, 136.81 (C3a and 3×PhCH$_2$), 133.19 (C7a), 127.99, 127.93, 127.56, 127.49, 127.38, 127.22, 126.98, 126.38 (3 PhCH$_2$), 133.19 (C7a), 127.99, 127.93, 127.56, 127.49, 127.38, 127.22, 126;98, 126.38 (3×PhCH$_2$ and C4), 123.91, 1 21.91 (C5 and C6), 113.95 (C7), 87.56 (C1'), 80.77, 77.60 77.31 (C2', C3', and C4'), 72.77, 71.36, 71.82 (3×PhCH$_2$), 69.50 (C5').

1-(β-D-Ribofuranosyl)-2,4,5,6-tetrachlorobenzimidazole (92)

To a solution of 0.565 g (0.858 mmol) of 91a in 8 mL of CH$_2$Cl$_2$, was added dropwise 8.58 mL of 1M BCl$_3$/CH$_2$Cl$_2$ at −78° C. The reaction mixture was stirred at −78° C. for 2 hr and then at −40° C. for 2 hr. MeOH (2.5 mL) was added dropwise and stirring was continued at −40° C. for 10 min. The reaction mixture was diluted with EtOAc (75 mL). The EtOAc solution was washed with H$_2$O (50 mL), sat. NaHCO$_3$ solution (50 mL), sat. NaCl solution (50 mL), dried (Na$_2$SO$_4$), and evaporated. The residue was suspended in a small amount of CHCl$_3$ and then filtered. The solid product was washed with portions of CHCl$_3$ and recrystallized from MeOH to give 0.271 g (81%) of 92 as white crystals. MP: 172°–175° C. (dec). $^1$H NMR (DMSO-d$_6$): d 8.62 (s, 1, 7-H), 5.89 (d, 1, 1'-H, J$_{1'-2}$=8.0 Hz), 5.52 (d, 1, 2'-OH, J$_{2'-2'OH}$=6.5 Hz), 5.46 (t, 1, 5'-OH, J$_{5'-5'OH}$=4.5 Hz), 5.31 (d, 1, 3'-OH, J$_{3'-3'OH}$=4.5 Hz, 4.39 (m, 1, 2'-H, J$_{2'-3}$=5.5 Hz), 4.14 (m, 1, 3'-H, J$_{3'-4}$=2.0 Hz), 4.04 (m 1, 4'-H, J$_{4'-5}$=J$_{4'-5''}$=2.5 Hz), 3.72 (m, 2, 5'-H and 5"-H, J$_{5'-5''}$=12.0 Hz). $^{13}$C NMR (DMSO-d$_6$): d 142.44 (C2), 138.56 (C3a), 131.95 (C7a), 126.91 (C4), 124.52, 122.39 (C5 and C$_6$), 113.55 (C7), 89.58 (C1'), 86.44 (C4'), 71.95 (C2'), 69.53 (C3'), 60.82 (C5'). Anal. Calcd. for C$_{12}$H$_{10}$Cl$_4$N$_2$O$_4$: C, 37.14; H, 2.50; N, 7.22. Found: C, 37.01.; H, 2.50; N, 7.01.

2-Chloro-1-(2,3,5-tri-O-acetyl-β-D-ribofuranosyl)-4,5,6-tribromobenzimidazoly) (102)

To a suspension of 0.779 g (2 mmol) of 20 in 10 mL of dry MeCN, was added 0.5 mL (2 mmol) of BSA. The reaction mixture was stirred at 75° C. for 15 min. This solution was treated with 0.700 g (2.2 mmol) of 1,2,3,5-tetra-O-acetyl-β-D-ribofuranose and 0.43 mL (2.2 mmol) of TMSOTf at 75° C. for 1 hr. The reaction mixture was cooled and diluted with EtOAc (50 mL). The EtOAc solution was washed with sat. NaHCO$_3$ solution (50 mL×2), sat. NaCl solution (50 mL), dried (Na$_2$SO$_4$), and evaporated.. The residue was recrystallized from MeOH to give 1.1 g of the blocked nucleoside as white crystals. This product contained some Impurity by TLC and was further purified on a silica column (1.9×25 cm, eluted with CHCl$_3$). Evaporation of fractions 8–20 (20 mL per fraction) and recrystallization from MeOH gave 0.974 g (2 crops, 75%) of 102 as white crystalline needles. MP: 163°–165° C. MS: (EI) m/e 643.8201 (2%, M$^+$=643.8196). $^1$H NMR (DMSO-d$_6$): d 8.25 (5, 1, 7-H), 6.25 (d, 1, 1'-H, J$_{1'-2}$=7.0 Hz), 5.53 (t, 1, 2'-H, J$_{2'-3}$=7.0 Hz), 5.43 (dd, 1, 3'-H, J$_{3'-4}$=4.5 Hz), 4.47 (dd, 5'-H, J$_{5'-4}$=5.0 Hz, J$_{5'-5''}$=11.5 Hz), 4.46 (m, 1,4'-H), 4.37 (dd, 1, 5'-H, J$_{5'-4}$=1.5 Hz), 2.15, 2.13, 2.01 (3×s, 9, 3×Ac). $^{13}$C NMR (DMSO-d$_6$): d 169.93, 169.42, 169.16 (3×COCH$_3$), 140.70 (C2), 140.85 (C3a), 132.58 (C7a), 121.30 (C5), 119.07 (C6), 115.93 (C4), 115.72 (C7), 86.94 (C1 '), 79.74 (4'), 70.73 (C2'), 68.62 (C3'), 62.53 (C5'), 20.66, 20.26, 19.97 (3×COCH$_3$). Anal. Calcd. for C$_{18}$H$_{16}$Br$_3$ClN$_2$O$_4$: C, 33.39; H, 2.49; N, 4.33. Found: C, 33.30; H, 2.33; N 4.31.

2-Chloro-1-(β-D-ribofuranosyl)-4,5,6-tribromobenzimidazole (103)

A mixture of 0.430 g (0.664 mmol) of the blocked nucleoside (102) and 0.21 6 g (3.317 mmol) of KCN in 13 mL of 70% EtOH was stirred at room temperature for 6 hr. The reaction mixture was diluted with 75 mL of EtOAc.. The EtOAc solution was washed with H$_2$O (50 mL), sat. NaCl solution (50 mL), dried (Na$_2$SO$_4$), and evaporated. The residue was chromatographed on a silica column (1.9×15 cm, eluted successively with CHCl$_3$, 1%, 2%, 3% MeOH/CHCl$_3$). Evaporation of fractions 43–60 (10 mL per fraction) and recrystallization from MeOH/MeCN gave 0.157 g (2 crops, 44%) of 103 as white crystals. MP: 168–170° C. MS: (FAB) m/e 518.7947 (28%, MH$^+$=

518.7957). $^1$H NMR (DMSO-d$_6$): d 8.76 (s, 1,7-H), 5.87 (d, 1, 1'-H, J$_{1'-2'}$ 8.0 Hz), 5.51 (d, 1,2'-OH, J$_{2'-2'OH}$=6.0 Hz), 5.42 (t, 1, 5'-OH, J$_{5'-5'OH}$=4.5 Hz), 5.30 (d, 1, 3'-OH, J$_{3'-3'OH}$=4.5 Hz), 4.37 (m, 1, 2'-H, J$_{2'-3}$=5.5 Hz), 4.14 (m, 1,3'-H, J$_{3'-4}$=2.0 Hz), 4.02 (m, 1,4'-H, J$_{4'-5}$=J$_{4'-5'}$=2.5 Hz), 3.71 (m, 2, 5'-H and 5'-H, J$_{5'-5''}$=12.0 Hz). $^{13}$C NMR (DMSO-d$_6$): d 142.32 (C2), 140.94 (C3a), 132.50 (C7a), 120.62 (C5), 118.44 (C6), 117.10 (C7), 115.34 (C4), 89.58 (C1'), 86.50 (C4'), 71.93 (C2'), 69.63 (C3'), 50.89 (C5'). Anal. Calcd. for C$_{12}$H$_{10}$Br$_3$ClN$_2$O$_4$ 0.3 MeCN: C, 28.36; H, 2.06; N, 6.04. Found: C, 28.25; H, 1.84; N, 5.90. (the Content of 0.3 MeCN was also indicated by $^1$H NMR.)

2-Azido-5,6-dichloro-1-(2-deoxy-3,5-di-O-p-toluoyl-β-D-erythro-pentofuranosyl)benzimidazole (110a)

Compound 110 (5.74 g, 10 mmol) was stirred with 4.90 g (100 mmol) of LiN$_3$ in 50 mL of dry DMF at 70° C. for 16 hr. The reaction mixture was evaporated and coevaporated 25 with toluene. The residue was partitioned between EtOAc/half sat. NaCl solution (250 mL/200 mL). The EtOAc layer was washed with half sat. NaCl solution (200 mL), dried (Na$_2$SO$_4$), and evaporated. The residue was dried under oil-pump vacuum at room temperature for 2 hr to give 110a as a yellowish foam (6.0 g, $^{18}$ 103%). This sample was pure by TLC and was used directly in the subsequent reactions without further purification. Analytical sample was obtained by recrystallization from EtOH. MP: 82°–85° C. MS: (EI) m/e 579.1065 (2.5%, M$^+$=579.1076). $^1$H NMR (DMSO-d$_6$): d 7.97, 7.81 (2×s, 2, 7-H and 4-H), 7.96, 7.88, 7.36, 7.30 (4×d, 8, Ph, J=8.0 Hz), 6.36 (dd, 1, 1'-H, J$_{1'-2}$=8.5 Hz, J$_{1'-2}$=6.0 Hz), 5.72 (m, 1, 3'-H, J$_{3'-2}$=7.0 Hz, J$_{3'-2}$=2.0 Hz, J$_{3'-4}$=3.5 Hz), 4.71 (dd, 1, 5'-H, J$_{5'-4}$=3.5 Hz, J$_{5'-5}$=120 Hz), 4.63 (dd, 1,5"-H, J$_{5''-4}$=5.0 Hz), 4.53 (m, 1, 4'-H), 3.05 (m, 1, 2'-H, J$_{2'-2}$=15.0 Hz), 2.60 (m, 1, 2"-H), 2.40, 2.36 (2×s, 6, 2×Me). $^{13}$C NMR (DMSO-d$_6$): d 165.46, 165.31 (2×p-MePhCO), 149.07 (C2), 144.04, 143.78 (2×p-MePhCO), 140.52 (C3a), 132.63 (C7a), 129.49, 129.24 129.20 (2×p-MePhCO), 126.55, 126.43, 125.35, 124.57 (2×p-MePhCO, C6, and C5), 118.98 (C4), 112.78 (C7), 63.78 (C1'), 81.19 (C4'), 73.90 (C3'), 63.72 (C5'), 35.31 (C2'), 21.15, 21.10 (2×p-MePhCO). Anal. Calcd. for C$_{28}$H$_{23}$Cl$_2$N$_5$O$_5$: C, 57.94; H, 3.99; N, 12.07. Found: C, 58.07; H, 4.12; N, 11.94.

2-Azido-5,6-dichloro-1 -(2-deoxy-β-D-erythro-pentofuranosyl)benzimidazole (110b)

Compound 110a (6.0 g, prepared from 10 mmol of 110) was treated with 1.50 mL of NH$_3$/MeOH at room temperature for 2 days. The reaction mixture was evaporated and coevaporated with MeOH. The resulting solid was triturated with CHCl$_3$ (50 mL). The CHCl$_3$ suspension was kept at 0° C. for 1 hr and was then filtered. The solid was washed with portions of CHCl$_3$ and then recrystallized from MeOH to give 2.462 g (2 crops) of 110b as white needles. The CHCl$_3$ filtrate was concentrated to 20 mL and kept in a freezer (~–15° C.) overnight. The precipitate was collected and recrystallized from MeOH to give additional 0.569 g (2 crops) of 110b. The total yield was 3.031 g (65% from 110); MP: 159°–161° C. (dec). MS: (EI) m/e 343.0232 (30%, M$^+$=343.0239). $^1$H NMR (DMSO-d$_6$): d 8.26 (s, 1,7-H), 7.81 (s, 1, 4-H), 6.09 (dd, 1, 1 '-H, J$_{1'-2}$=9.0 Hz, J$_{1'-2''}$=6.0 Hz), 5.36 (d, 1,3'-OH, J$_{3'-3'OH}$=4.5 Hz), 5.15 (t, 1, 5"-OH, J$_{5'-5'OH}$=5.0 Hz), 4.39 (m, 1, 3'-H, J$_{3'-2}$=6.5Hz, J$_{3'-2}$=2.5 Hz, J$_{3'-4}$=3.0 Hz), 3.84 (m, 1,4'-H, J$_{4'-5}$=3.5 Hz), 3.65 (m, 2, 5'-H), 2.50 (m, 1, 2'-H, J$_{2'-2}$=13.0 Hz), 2.09 (m, 1, 2"-H). $^{13}$C NMR (DMSO-d$_6$): d 149.00 (C2), 140.90 (C3a), 132.11 (C7a), 125.13, 124.25 (C5 and C6), 118.79 (C4), 114.11 (C7), 87.52 (C4'), 84.08 (C1'), 70.15 (C3'); 60.10 (C5'), 58.54 (C2'). Anal. Calcd. for C$_{12}$H$_{11}$Cl$_2$N$_5$O$_3$: C, 41.88; H, 3.22; N, 20.35. Found: C, 42.01; H, 3.13; N, 19.98.

2-Amino-5,6-dichloro-1-(2-deoxy-β-D-erythro-pentofuranosyl)benzimidazole (113)

A mixture of 110b (1.032 g, 3 mmol) and Ra-Ni (0.24 g, wet) in 30 mL of EtOH was hydrogenated (50 psi of H$_2$) at room temperature for 6 hr. The reaction mixture was filtered and the filtrate was evaporated. The residue was suspended in 20 mL of MeCN and the suspension was filtered to give 0.856 g (90%, 2 crops) of 113 as a white solid. Analytical sample (as white needles) was obtained by recrystallization from MeOH/MeCN. MP: 216°–221° C (dec.). MS: (EI) m/e 317.0340 (37%, M$^+$=317.0334). $^1$H NMR (DMSO-d$_6$ d 7.71 (s, 1, 7-H), 7.29 (s, 1, 4-H), 6.93 (br s, 2, 2-NH$_2$), 6.23 (dd, 1, 1'-H, J$_{1'-2}$=8.5 Hz, J$_{1'-2''}$=6.0 Hz), 5.40.(t, 1, 5'-OH, J$_{5'-5'OH}$=4.5 Hz), 5.34 (d, 1, 3'-OH, J$_{3'-3'OH}$=4.0 Hz), 4.40 (m, 1, 3'-H, J$_{3'-2}$=7.0 Hz, J$_{3'-2}$=2.0 Hz, J$_{3'-4}$=2.5 Hz), 3.82 (m, 1, 4'-H, J$_{4'-5}$=2.5 Hz), 3.68 (m, 2, 5'-H), 2.40 (m, 1, 2'-H, J$_{2'-2}$=13.0 Hz), 2.05 (m, 1, 2'-H). $^{13}$C NMR (DMSO-d$_6$): d 155.65 (C2), 143.16 (C3a), 132.40 (C7a), 122.94, 119.77 (C5 and C6), 115.35 (C4), 110.69 (C7), 86.91 (C4'), 83.87 (C1'), 70.20 (C3'), 60.74 (C5'), 38.05 (C2') Anal. Calcd. for C$_{12}$H$_{13}$Cl$_2$N$_3$O$_3$: C, 45.30; H, 4.12; N, 13.21. Found: C, 45.44; H, 4.10; N, 13.28.

2,5,6-Trichloro-1-(2,3,5-tri-O-benzyl-β-D-arabinofuranosyl)benzimidazole (133)

Compound 5 (598 mg 2.7 mmole) was dissolved in dry CH$_3$CN(60 ml) and 97% NaH (80 mg, 3 mmole) was added. The mixture was stirred under N$_2$ for 1 hour at room temperature. Then 2,3,5-tri-O-benzyl-D-arabinofuranosyl chloride (prepared from 2,3,5-tri-O-benzyl-1-O-p-nitrobenzoyl-D-arabinofuranose) (1.83 g, 3 mmole)) dissolved in dry CH$_3$CN (20 ml) was added dropwise. The mixture was stirred under N$_2$ for overnight at room temperature. The reaction solution was filtered through Celite. The filtrate was evaporated to give a syrup and this syrup was subjected to flash column chromatography on silica gel (Kieseigel 60, 230–400 mesh) and eluted with CH$_2$Cl$_2$. The fractions containing 133 were combined and evaporated to give 1.6 g (95.0%) of 133. (IR KBr cm$^{-1}$: 1140-1060 (C-O-C)).

2,5,6-Trichloro-1-(β-D-arabinofuranosyl)benzimidazole (134)

Compound 133 (1.25 g 2 mmole) was dissolved in dry CH$_2$Cl$_2$ (20 ml) and this solution was cooled in an acetone-dry ice bath. A 1M solution of BCl$_3$ in CH$_2$Cl$_2$ (10 ml) was added and the mixture was stirred at –70° for 4.5 hr. At this point TLC showed no starting material. CH$_3$OH (10 ml) was added and the solution was made neutral with NH$_4$OH. The solution was evaporated in vacuo to dryness. H$_2$O (20 ml) was added and the solution was extracted with EtOAc. The EtOAc layer was washed with H$_2$O, dried (Na$_2$SO$_4$) and evaporated in vacuo to obtain a syrup. This syrup was subjected to flash column chromatography on silica gel (Kieselgel. 60, 230–400 mesh) with CH$_2$Cl -MeOH (20:1) as eluent solvent to give 134. Yield 0.551 g, 77.9%.

2,4,5,6,7-Pentachloro-1-[(1,3-dibenzyloxy-2-propoxylmethyl]benzimidazole (154)

The title compound was prepared from 2,4,5,6,7-pentachlorobenzimidazole (14) (0.29 g, 1.0 mmole), CH₃CN (35 mL), NaH (97%, oil dispersion, 0.033 g, 1.4 mmole) and [(1,3-bis(benzyloxy)-2-propoxy]methylchlodde (0.49 g, 1.5 mmole) in CH₃CN (10 mL) to afford an oil. The resulting oil was purified by flash column chromatography (2×20 cm) (230–400 mesh) prepared with wet $SiO_2$ in hexane. Elution with hexane:EtOAc (8:2,v/v) gave 0.32 g of the blocked product 154 as an oil. Although the $^1H$ NMR spectra revealed a small mount of an impurity, the compound was used without further purification for the next step. 2,4,5,6,7-Pentachloro-1-[(1,3-dihydroxy-2-propoxy) methyl]benzimidazole (155)

Compound 155 (0.52 g, 51%) was prepared from 154 (1.5 g, 2.6 mmole), $BCl_3$ (5M solution in $CH_2CH_2$, 14 mL), $CH_2Cl_2$ (30 mL) and MeOH (20 mL) by the method described for 166 which on recrystallization from EtOAC gave 155: m.p. 155°; $^1H$ NMR (DMSO-$d_6$): d 5.76 (s, 2 H, C-1'), 4.63 (t, 2 H, exchanges with $D_2O$, 2×OH), 3.54-3.48 (m, 1 H, C-3'), 3.43-3.25 (m, 4 H, C-4' and 5'H). Anal. Calcd. for $C_{11}H_9N_2Cl_5O_3$: C, 33.46; H, 2.28; N, 7.09. Found: C, 33.60; H, 2.15; N, 6.91.

2-Methoxy-4,5,6,7-tetrachloro-1-[(1,3-dihydroxy-2-propoxy)methyl]benzimidazole (157a) and 2-Amino-4,5,6,7-tetrachloro-1-[(1,3-Dihydroxy-2-propoxy)methyl]benzimidazole (156)

A mixture of 155 (0.28 g, 0.71 mmole) and methanolic ammonia (methanol saturated with ammonia at 0° C. 60 mL) was stirred at room temperature for 36 hr in a pressure bottle. The resulting mixture was evaporated to dryness and was purified by flash column chromatography (3×15 cm) (230–400 mesh). Elution of the column $CH_2Cl_2$:MeOH (97:3, v/v) and evaporation of the appropriate fractions followed by recrystallization from MeOH gave 0.06 gm (20%) of 157a: m.p. 192° C.; $^1H$ NMR (DMSO-$d_6$): d 5.71 (s, 2 H, C-1'), 4.59 (t, 2 H, exchanges with $D_2O$, 2×OH ), 4.19 (s, 3H, $OCH_3$), 3.75-3.21 (m, 5 H, C-3', C-4' and C-S'). Anal. Calcd. for $C_{12}H_{12}N_2Cl_4O_4$: C, 36.92; H, 3.07; N, 7.17. Found: C, 37.20; H, 2.99; N, 6.93.

Further elution of the $CH_2Cl_2$:MeOH (90:1, v/v) and evaporation of the appropriate fractions followed by recrystallization from the mixture of DMSO-$H_2O$ gave 0.2 g (69%) of 156: m.p. 268° C. $^1H$ NMR (DMSO-$d_6$): d 7.40 (bs, 2 H, exchanges with $D_2O$, $NH_2$), 5.75 (s, 2 H, Cl'), 4.77 (bs, 1 H, exchanges with $D_2O$, 2×OH ), 3.58-3.34 (m, 5 H, C-3', C-4' and C-S'). Anal. Calcd. for $C_{11}H_{11}N_3Cl_4O_3$: C, 35.20; H, 2.93; N, 11.20. Found: C, 35.37; H, 3.02; N, 10.86.

2,4,5,6,7-Pentachloro-1-(2-acetoxyethoxymethyl)benzimidazole (165)

NaH (0.12 g, 3.0 mmole, 60% oil disperson) was added to a stirred suspension of 2,4,5,6,7-pentachlorobenzimidazole (14) (1.0 g, 3.4.mmole) in dry CH₃CN (120 mL) under a $N_2$ atmosphere. The solution was stirred until $H_2$ evolution has ceased and a clear solution was obtained (20 min.). (2-Acetoxyethoxy) methyl bromide (0.68 g, 10.66 mmole) in CH₃CN (34 mL) was then added dropwise. The reaction mixture was stirred for an additional 3 hr. The resulting mixture was concentrated under reduced pressure, diluted with $H_2O$ (50 mL), extracted with EtOAc (100 mL), washed with $H_2O$ (100 mL), dried (anhyd. $Na_2SO_4$) and the solvent was removed under reduced pressure to yield an oil (165). The resulting oil was purified by flash column chromatography (2×24 cm) (230–400 mesh). Elution of the column with hexane:EtOAc (6:4, v/v) and evaporation of the appropriate fractions gave a solid which was recrystallized from MeOH to afford 1.39 g (72%) of 165: m.p. 119° C. $^1H$ NMR (CDCl₃): d 5.93 (s, 2 H, C-1'), 4.143.92 (m, 4 H, C-3' and C-4'), 1.83 (s, 3 H, Ac). Anal. Calcd. for $Cl_2H_9N_2Cl_5O_3$: C,35.45; H, 2.23; N, 6.89. Found: C, 35.57; H, 2.17; N, 16.91.

2,4,5,6,7-Pentachloro-1-(2-benzyloxyethoxymethyl) benzimidazole

NaH (0.033 g, 1.52 mmole, 90% oil disperson) was added to a stirred suspension of 2,4,5,6,7-pentachlorobenzimidazole (14) (0.3 g, 1.03 mmole) in dry CH₃CN (35 mL) under a $N_2$ atmosphere. The sSolution was stirred until $H_2$ evolution had ceased and a clear solution was obtained (20 min.). (2-Benzyloxyethoxy)methylchloride (0.31 g, 1.54 mmole) in CH₃CN (10 mL) was then added dropwise. The reaction mixture was stirred for an additional 15 hr. The resulting mixture was concentrated under reduced pressure, diluted with $H_2O$ (50 mL), extracted with EtOAc (100 mL), washed with $H_2O$ (100 mL), dried (anhyd. $Na_2SO_4$) and the solvent was removed under reduced pressure to yield an oil. The resulting oil was purified by flash column chromatography (2×24 cm) (230–400 mesh). Elution of the column with hexane:EtOAc (6:4, v/v) and evaporation of the appropriate fractions followed by crystallization from hexane:EtOAc afforded 0.18 g (38.4%) of blocked product: m.p. 95° C; $^1H$ NMR (CDCl₃): d 7.22–7.34 (m, 5H, $C_6H_5$), 5.93 (s, 2 H, C-1'), 4.47 (s, 2H, $CH_2C_6H_5$), 3.70–3.73 (m, 2 H, C-3'), 3.45–3.57 (m, 2 H, C-4'), 1.83 (s, 3 H, Ac). Anal. Calcd. for $C_{17}H_{13}NCl_5O_2$: C, 44.88; H, 2.86; N, 6.16. Found: C, 44.95; H, 2.59; N, 6.05.

2,4,5,6,7-Pentachloro-1-(2-hydroxyethoxymethyl) benzimidazole (166)

To a solution of the blocked product (1.2 g, 2.63 mmole) in dry $CH_2Cl_2$ (25 mL) at −78° C. under $N_2$ atmosphere, $BCl_3$ (5M solution in $CH_2Cl_2$, 18 mL) was added dropwise while maintaining the bath temperature at 78° C. The reaction mixture was stirred for an additional 4 hr, MeOH (18 mL) was added at 0° C. and the cold solution was immediately neutralized (pH 7) with $NH_4OH$. The solution was allowed to warm up to room temperature and then concentrated at 40° C. to yield an oil. The resulting mixture was diluted with $H_2O$ (100 mL), extracted with EtOAc (250 mL), washed with $H_2O$ (100 mL), dried (anhyd. $Na_2SO_4$) and concentrated in vacuo. The product thus obtained, was purified by flash column chromatography (2×24 cm) (230–400 mesh). Elution of the column with hexane:EtOAc (6:4, v/v) and evaporation of the appropriate fractions gave a solid which on recrystallization from hexane:EtOAc afforded 0.45 gm (45%) of 166: m.p. 168°–170° C; $^1H$ NMR (DMSO-$d_6$): d 5.83 (s, 2H, C-1'), 4.62 (t, 1 H, exchanges with $D_2O$, OH), 3.54-3.50 (m, 2 H, C-3'), 3.44-3.38 (m, 2 H, C-4'). Anal. Calcd. for $C_{10}H_7N_2Cl_5O_2$: C, 32.62; H, 1.92; N, 7.68. Found: C, 32.68; H, 1.82; N: 7.33.

2-Methoxy-4,5,6,7-tetrachloro-1-(2-hydroxyethoxymethyl)benzimidazole (166a) and 2-Amino-4,5,6,7-tetrachloro-1-(2-hydroxyethoxymethyl)benzimidazole (167)

A mixture of 165 (0.2, 0.49 mmole) and methanolic ammonia (methanol saturated with ammonia at 0° C., 30 mL) was stirred at room temperature for 12 hr in a pressure bottle. The resulting mixture was evaporated to dryness and purified by flash column chromatography (2×25 cm) (230–400 mesh). Elution of the column $CH_2Cl_2$:(97:3, v/v) and evaporation of the appropriate fractions followed by recrystallization from the mixture of hexane:EtOAc gave 0.02 gm (13.24%) of 166a: m.p. 139° C.; $^1$H NMR (DMSO-$d_6$): d 5.44 (s, 2 H, C-1'), 4.69 (t, 1 H, exchanges with $D_2O$, OH ), 3.86 (s, 3 H, $OCH_3$), 3.46-3.41 (m, 4 H, C-3' and C-4'). Anal. Calcd. for $C_{11}H_{10}N_2Cl_4O_2$: C, 34.81; H, 3.62; N, 12.16. Found: C, 34.59; H, 2.55; N, 11.79.

Further elution of the $CH_2Cl_2$:MeOH (90:1, v/v) and evaporation of the appropriate fractions followed by recrystallization from the mixture of DMSO-$H_2O$ gave 0.06 g (39.5%) of 167: m.p. 268° C; $^1$H NMR (DMSO-$d_6$): d 7.42 (s, 2 H, exchanges with $D_2O$, $NH_2$), 5.66 (s, 2 H, C-1'), 4.69 (bs, 1 H, exchanges with $D_2O$, OH ), 3.47 (m, 4 H, C-3' and C-4'). Anal. Calcd. for $C_{10}H_9N_3Cl_4O_2$: C, 36.62; H, 2.79; N, 7.78. Found: C, 36.61; H, 2.16; N, 7.65

1-Benzyl-2,5,6-trichlorobenzimidazole (181)

2,5,6-Trichlorobenzimidazole (5, 50 mg, 0.0002 moles) was dissolved in 15 ml of $CH_3CN$, and $K_2CO_3$ (33 mg, 0.0002 moles) was added. The mixture was stirred at room temperature for one hour, at which time benzyl bromide (0.024 ml, 0.0002 moles) was added. The mixture was then stirred for two days. TLC analysis showed the formation of a new compound with a higher $R_f$ than starting material. The mixture was then concentrated and a liquid-liquid extraction was done using $CHCl_3$, and $H_2O$. The $CHCl_3$ layer was kept, dried with $MgSO_4$, filtered, and then concentrated. Column chromotograpy was then performed using 2% MeOH/$CHCl_3$ to elute the compounds. The fractions were collected and those containing the compound were concentrated. The compound was recrystallized from MeOH, giving 60 mg of 1-benzyl-2,5,6-trichlorobenzlmtdazole (181) (96.2%). $^1$H NMR ($CDCl_3$): d 3.49 ppm (s,3H), 7.13 (m, 2H), 7.32 (m, 4H), 7.78 (s, 1H). $^{13}$C NMR ($CDCl_3$): d 43.20 ppm, 106.25, 115.78, 121.62, 122.24, 122.66, 123.50, 124.15, 129.05, 129.16, 135.97, 137.68. GC-MS: m/e 310, 273, 239, 221, 197, 170, 168, 135, 120, 100, 91, 77, 65, 51, 39. m.p: 175°–176° C. Elemental Analysis: ($C_{14}H_9Cl_3N_2$): Calculated: C, 53.85; H, 2.68; N, 8.97. Found: C, 53.92; H, 2.85; N, 8.89. UV lmax nm (e×104): (pH 7) 263 (0.080), 290 (0.102), 299 (0.154); (pH 1) 224 (0.412), 255 (0.157), 290 (0.155), 299 (0.166).

2-Amino-1-benzyl-5,6-dichlorobenzimidazole (182)

Method A(182) 2-Amino-5,6-dichlorobenzimidazole (4) (1 g, 4.95 mmole) was dissolved in acetonitrile (200 ml) and NaOH (198 mg, 4.95 mmole) was added. After stirring for 1 hr at room temperature, benzyl bromide (0.589 ml, 4.95 mmole) was added and the mixture was allowed to stir overnight. The mixture was concentrated under reduced pressure and purified on a silica gel column (3.5×5 cm) using 5% MeOH/$CHCl_3$ to give 1:23 g (85%) of 2-amino-1-benzyl-5,6-dichlorobenzimidazole (182). The compound was then recrystallized from EtOH/$H_2O$ to give a white powder. $^1$H NMR (DMSO-$d_6$): d 5.28 ppm (s, 2H), 6.95 (s, 2H), 7.16 (d, 2H), 7.25 (d, 1H), 7.31 (m, 4H). $^{13}$C NMR (DMSO-$d_6$): d 44.74 ppm, 109.15, 115.37, 119.62, 122.66, 126.82, 127.37, 128.55, 134.10, 136.46, 143.13, 156.91. MS (Electron Impact): m/e 291, 200, 158, 91, 65. MP: 245°–246° C. Elemental Analysis: ($C_{14}H_{11}Cl_2N_3$,): Calculated: C, 57.55; H, 3.79; N, 14.38. Found: C, 57.66; H, 3.83; N, 13.98. UV lmax nm (e×10$^4$): (pH 7) 230 (0.761), 260 (0.324), 302 (0.452); (pH 1) 238 (0.306), 294 (0.383), 299 (0.359); (pH 11) 229 (0.869), 257 (0.316), 301 (0.443).

Method B(182)

Compound 118 was treated with methanolic ammonia for 18 hr, at an elevated temperature, to afford compound 182, after a standard isolation and purification procedure.

D. Antiviral Activity of Compounds

The following test methods were followed in generating the data in Tables 1 through 3 and FIGS. 3 through 6.

METHODS (1) Propaqation of Cells and Viruses (a) Cells

The routine growth and passage of KB cells, a human epidermoid neoplastic cell line, was performed in monolayer cultures using minimal essential medium (MEM) with either Hanks salts [MEM(H)] or Eade salts ([MEM(E)] supplemented with 10% calf serum or 5 to 10% fetal bovine serum. The sodium bicarbonate concentration was varied to meet the buffering capacity required. BSC-1 (African green monkey kidney) cells were grown and passaged in Dulbecco modified MEM(E) supplemented with 5% tryptose phosphate broth and 5% horse serum. Cultures of human foreskin fibroblasts (HFF) were grown in medium consisting of MEM(E) with 10% fetal bovine serum.

Cells were passaged at 1:2 to 1:10 dilutions according to conventional procedures by using 0.05% trypsin plus 0.02% EDTA in a HEPES buffered salt solution. HFF cells were passaged only at 1:2 dilutions.

(b) Viruses

The S-148 strain of HSV-1 was used in most experiments and was provided by Dr. T. W. Schafer of Schering Corporation. The HF strain of HSV-1 was used in selected experiments and was obtained from Dr. G. H. Cohen, University of Pennsylvania. The Towne strain, plaque-purffied isolate $P_o$, of HCMV was a gift of Dr. Mark Stinski, University of Iowa.

High titer HSV-1 stocks were prepared as follows: Nearly confluent monolayer cultures of KB cells were grown in 32 oz. glass bottles containing MEM(E) buffered with 25 mM HEPES and supplemented with 5% fetal bovine serum and 0.127 g/liter L-arginine (VGM, virus growth medium). The cultures were infected at a low input multiplicity to reduce the formation of defective virus. After cell cytopathology reached "three to four plus", the cells were harvested by vigorous shaking, and concentrated by centrifugation (800×g for 5 min.). The resulting virus pools were stored at –76° C. until retrieved for use in experiments.

Stock HCMV was prepared by infecting HFF cells at a multiplicity of infection (m.o.i.) of less that 0.01 plaque-forming units (p.f.u.) per cell. Cell growth medium was changed every four days until cytopathology was evident in all cells (approximately 21 days). Supernatant fluids were retained as the virus stock. Four days later, the remaining cells were disrupted by three cycles of freeze-thawing and the cell plus medium held as an additional source of virus. Storage was in liquid nitrogen.

HSV-1 was titered using monolayer cultures of BSC-1 Cells. Cells were planted at 3×10$^5$ cells/well using 6-well cluster dishes. MEM(E) supplemented with 10% fetal bovine serum was employed as medium. After 22–24 h, cells were 90% confluent and were inoculated in triplicate using at least three ten-fold dilutions with 0.2 ml of the virus suspension to be asseyed and incubated in a humidified 4% $CO_2$-90% air atmosphere for one hour to permit viral adsorption. Following virus adsorption, the cell sheet was overlayed with 5 ml of MEM(E) with 5% serum plus 0.5% methocel (4000 CPS) and incubated an additional two to three days. Cells were fixed and stained with 0.1% crystal violet in 20% methanol and macroscopic plaques enumerated.

HCMV was titered in 24-well cluster dishes which were planted to contain 5×10$^4$ HFF cells/well, grown as described above. When the cells were 70 to 80% confluent, 0.2 ml of the virus suspension was added per well and adsorbed as described above. At least three ten-fold dilutions of each preparation were used. Following virus adsorption, the cell sheets were overlayed with 0.5% methocel (4000 CPS) in maintenance medium [MEM(E) with 1.1 g/liter $NaHCO_3$, 100 units/ml penicillin G, 100 μg/ml streptomycin, and 5% fetal bovine serum]. The cultures were incubated in a humidified atmosphere of 4% $CO_2$-96% air. Viral foci were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20-fold magnification using a Nikon Profile Projector.

(2) Assays for Antiviral Activity (a) HSV-1

Plaque reduction experiments with HSV-1 were performed using monolayer cultures of BSC-1 cells. The assay was performed exactly as described above except that the 0.2 ml virus suspension contained approximately 100 p.f.u. of HSV-1. Compounds to be tested were dissolved in the overlay medium at concentrations usually ranging from 0.1 to 100 μM in half-or-one logarithm$_{10}$ dilutions. Titer reduction assays were performed by planting KB cells in 25 $cm^2$ plastic tissue culture flasks 10 to 24 hr prior to infection. At the onset of experiments, logarithmically growing replicate monolayer cultures were 60 to 80% confluent and contained 2.5 to 4.5×$10^6$ cells/flask. Medium was decanted and the cultures were infected with 2 to 10 p.f.u. of HSV-1 per cell. Virus was contained in 1.0 ml of VGM supplemented with 5% fetal bovine serum. After a 1 h adsorption period at 370°C., the cell sheet was rinsed twice with 2 ml of VGM without serum to remove unadsorbed virus and 5 ml of VGM containing drugs at three to five selected concentrations added in duplicate. Following an 18-to 20-hr incubation at 37° C., infected monolayers were treated with EDTA-trypsin to suspend the cells; aliquots were removed, subjected to three cycles of freezing and thawing, and stored at −76° C. for subsequent virus assay. Virus was titered on BSC-1 cells as described above.

ELISA techniques according to standard procedures were also used to determine activity against HSV-1. Drug effects were calculated as a percentage of the reduction in virus titers in the presence of each drug concentration compared to the titer obtained in the absence of drug. Acylovir was used as a positive control in all experiments.

(b) HMV

The effect of compounds of the replication of HCMV has been measured using both a plaque (focus) reduction assay and a titer (yield) reduction assay. For the former, HFF cells in 24-well culture dishes were infected with approximately 50 p.f.u. of HCMV per well using the procedures detailed above. Compounds dissolved in growth medium were added in three to six selected concentrations to triplicate wells following virus adsorption. Following incubation at 37° C. for 7 to 10 days, cell sheets were fixed, stained and microscopic plaques were enumerated as described above. Drug effects were calculated as a percentage of reduction in number of foci in the presence of each drug concentration compared to the number observed in the absence of drug. DHPG (ganciclovir) was used as a positive control in all experiments.

For titer reduction assays, HFF cells were planted as described above in 24-well cluster dishes or in 25 $cm^2$ flasks. When monolayers were approximately 70% confluent, HCMV was added at a m.o.i. of 0.5 p.f.u. per cell and adsorbed as detailed above. Compounds dissolved in growth medium were added in one or one-half-logarithm$_{10}$ dilutions and incubation continued at 37° C. After 7 to 10 days of incubation, culture dishes of flasks were frozen at 76° C. For titer determination, cells were thawed and then, subjected to two more cycles of freezing and thawing at 37° C. Serial, one-logarithm$_{10}$ dilutions of the final suspension were prepared and inoculated onto new cultures of HFF cells. Titer determination was as detailed above in part (b).

(3) Cytotoxicity Assays (a) Protocol for Determining Effects of Compounds on DNA, RNA and Protein Synthesis KB or HFF cells were planted using a Costar Transplate-96 (Costar, Cambridge, Mass.) in Costar 96-well cluster dishes at a concentration of 10,000 to 12,000 cells per well. Cells were suspended in 200 μl of medium [MEM(H) plus 0.7 g/liter $NaHCO_3$ supplemented with 10% calf serum] per well. After incubation of 16 to 24 hours at 37° C. in a humidified atmosphere of 4% $CO_2$ in air, 150 μl of medium was removed per well. One-hundred μl of medium with or without compounds in twice their final concentrations was added to each well using a Titertek Multichannel Pipette. Final concentrations of compounds ranged from 0.1 to 320 pl of medium containing radioactive precursors also was added to each well to give a final concentration to 1 to 3 μCi/ml of labeled precursor. [$^3$H]Thd was diluted with unlabeled dThd to give a final concentration of 3to6 μM.

Following addition of drugs and labeled precursors, plates were incubated as described above for an additional 18 to 24 hr. Logarithmic cell growth occurred during this time with continual uptake of labeled precursors. At the end of the incubation period, cells were individually harvested from each well using a Skatron Cell harvester (Skatron, Inc., Sterling, Va.). Cultures for individual wells were harvested onto filter paper and washed free of unincorporated label with nine sequential washes with 5% trichloroacetic acid, nine washes with water, and nine with ethanol using the Skatton unit. Filters were dried, circles from individual cultures were punched from the filter mat and placed into mini-vials. Liquid scintillation solution was added, and radioactivity determined in a Beckman model LS8100 Liquid scintillation spectrometer. All samples were counted for 2.0 min each, with three round of counting. Counts per minute were determined following the application of statistical methods to eliminate count rates which fell outside distribution limits defined by Chauvenetys rejection criterion.

All analyses were performed in triplicate. That is, three culture wells were used per time point, radioactive precursor, and drug concentration in all experiments. Results from triplicate assays were converted to percent of control and plotted as log dose-response curves from which 50% inhibitor (150) concentrations were interpolated. Three concentrations of vidarabine were included on all plates as a positive control.

(b) Visual Scoring

Cytotoxicity produced in HFF and BSC-1 cells was estimated by visual scoring of cells not affected by virus infection in the HCMV and HSV-1 plaque reduction assays. Cytopathology was estimated at 35- and 60-fold magnification and scored on a zero to four plus basis. Wells were scored on the day of staining.

(4) Cell Growth Rates

Population doubling times and cell viability were measured in uninfected HFF and/or KB cells. Cells were planted in replicate 6-well plastic tissue culture dishes or in 25 $cm^2$ flasks as described above in part 1. Following an incubation period during which cells attached to the substrate, medium was decanted, the cell sheet rinsed once with HBS, and fresh medium added. The medium consisted of MEM(E) with 1.1 g $NaHCO_3$/liter and 10%. fetal bovine or calf serum plus appropriate log or hafl-log concentrations of drug. After additional periods of incubation from 1 to 72 hours at 37° C., cells were harvested by means of 0.05% trypsin plus 0.02% EDTA in a HEPES-buffered salt solution. Cells were enumerated using either a Coulter counter or a homocytometer and viability determining using trypsan blue dye exclusion.

(5) Plating Efficiency

A plating efficiency assay was used to confirm and extend results described above. Briefly, KB cells were suspended in growth medium and an aliquot containing 1000 cells was added to a 140×25 mm petri dish. Growth medium (44 ml) containing selected concentrations of test compounds was added and the cultures incubated in a humidified atmosphere of 4% $CO_2$-96% air, 37° C. for 14 days. Medium then was decanted and colonies fixed with methanol and stained with 0.1% crystal violet in 20% methanol. Macroscopic colonies greater than 1 mm in diameter were enumerated. Drug effects were calculated as a percentage of reduction in number of colonies formed in the presence of each drug concentration compared to the number of colonies formed in the absence of drugs. Dose-response curves were generated and $I_{50}$ concentrations for inhibition of plating/colony formation were calculated.

(6) Data Analysis

Dose-response relationships were used to compare drug effects. These were constructed by linearly regressing the percent inhibition of parameters derived in the preceding sections against log drug concentrations. The 50 inhibitory ($I_{50}$) concentrations were calculated from the regression lines using the methods described by Goldstein. See. Goldstein, A., *Biostatistics: An Introductory Text*, MacMillan, New York, pp. 156–161 (1964). The three $I_{50}$ concentrations for inhibition of DNA, RNA and protein synthesis were averaged and were reported in the tables. Along with the $I_{50}$ concentrations are compared to $I_{50}$ concentrations for inhibition for HCMV or HSV-1 replication. Compounds for which the ratio of cytotoxicity $I_{50}$ concentrations to antiviral $I_{50}$ concentrations (in vitro therapeutic index) were greater than 10, were considered for further study.

RESULTS (1) Antiviral Activity and Cytotoxicity of Benzimidazoles

Table 1 below summarizes test results from antiviral and cytotoxicity evaluation of the benzimidazoles. These halogen-substituted compounds were active against HCMV, with a halogen at $R_5$ being essential for antiviral activity and low cytotoxicity. For example, compounds 45 and 52 were active against HCMV in the sub- or low micromolar range and did not produce cytotoxicity in uninfected cells at concentrations up to 100 µM. This potent and selective antiviral activity against HCMV is in sharp contrast to the low, apparent activity against this virus of the dichloro compound commonly referred to as DRB which compound was initially described by Tatum (I. Tamm, *Science* 120:847–848, 1954). The $R_2$ and $R_3$ positions in this compound are substituted by Cl but the $R_5$ position is unsubstituted. Although this compound appears to have weak activity against HCMV and HSV-1 (Table 1), this activity was observed only at concentrations which produced cytotoxicity in uninfected cells (Table 1 and FIG. 6). Thus in contrast to compounds disclosed herein, the activity of DRB against HCMV is not actual antiviral activity but rather is a manifestation of cytotoxicity.

Other compounds showing good or better activity than compound 45 against HCMV and low cytotoxicity are compounds 52, 85, 95, 99 and compound 111 (the deoxyribosyl analog of compound 45). Other compounds with activity include compounds 61, 81, 83a, and 107. All compounds except 81, 95, and 99 also had activity against HSV-1.

TABLE 1

| | 50% Inhibitory Concentration (µM) | | | | | |
|---|---|---|---|---|---|---|
| | Antiviral Activity Against: | | | Cytotoxicity | | |
| Compound | HCMV | | HSV-1 | In Cell Line: | | |
| Number[a] | Plaque | Yield[b] | Plaque | HFF[c] | BSC[c] | KB[d] |
| 45 | 2.8[e] | 1.4[e] | 151[e] | 238[e] | >100 | 175[e] |
| 52 | 2.5[e] | 0.3[e] | 99[e] | 100[e] | | >100 |
| 61 | 19[e] | — | 27[e] | 32[e] | | 9 |
| 81 | 11 | 2.0 | >100 | 32 | | >100 |
| 83a | 30[e] | 26[e] | 21[e] | >100[e] | | 23 |
| 85 | 5.7[e] | 2.5[e] | 55 | 75[e] | | 109[e] |
| 95 | 6.0[e] | 1.5[e] | >100[e] | 100[e] | | 156[e] |
| 99 | 7.0[e] | 2.8[e] | >100[e] | 100[e] | | 139[e] |
| 107 | 1.7[e] | 2.0 | 50 | 10[e] | | 19 |
| 111 | 20[e] | 12 | 41 | >320[e] | | 53 |
| 112 | 35[e] | 6 | — | 32[e] | | 171[e] |
| DRB[f] | 42[e] | 19[e] | 30[e] | 24[e] | | 36[e] |

[a]Number for chemical structure presented in text.
[b]90% inhibitory concentration ($I_{90}$) presented.
[c]Visual cytotoxicity scored on HFF or BSC-1 cells at time of HCMV or HSV-1 plaque enumeration.
[d]Average percent inhibition of DNA, RNA and protein synthesis or cell growth determined in KB cells as described in the text.
[e]Average of two to eight replicate experiments.
[f]Initially described by I. Tamm, Science 120:847–848 (1954).

Table 3 below summarizes test results from antiviral and cytotoxicity evaluation of benzimidazoles and related compounds. These compounds are active against HCMV and some also are active against HSV-1. For example, compounds 57, 65, 65a, 87, 90, 103, 113, 134, 155, 156, 182, 92, 81c and 54 were active against HCMV in the low-micromolar range in either plaque or yield reduction assays. Although some comounds also showed cytotoxic effects in some assays, activity against HCMV was separated from cytotoxicity. All other compounds presented in Table 3 also were active against HCMV but to a lesser extent.

In addition to activity against HCMV, compounds 44, 65a, 113, 134, 182, 54, 19, 12c, 13 and 26 also are active against HSV-1.

TABLE 3

| | Antiviral Activity and Cytotoxicity | | | | | |
|---|---|---|---|---|---|---|
| | 50% Inhibitory concentration (µM) | | | | | |
| | Antiviral Activity Against: | | | Cytotoxicity | | |
| Compound | HCMV | | HSV-1 | In Cell Line: | | |
| Number[a] | Plaque | Yield[b] | Plaque | HFF[c] | BSC[c] | KB[d] |
| 7 | 4 | | | 10 | | |
| 12c | 111[e] | >100[e] | 42[e] | 77[e] | | 45 |
| 13 | 18 | | 79 | 32 | | |
| 19 | 6[e] | 0.01 | 21[e] | 20[e] | | |
| 26 | 2.8 | 7.0 | 25 | 10 | | |
| 32 | 5.1[e] | | >100 | 32[e] | | >100 |
| 41 | 20 | | | 32 | | |
| 41c | 25 | | | 32 | | |
| 44 | 40 | | 50 | 32 | | |
| 54 | 22 | 7.0 | 25 | 100 | 100 | >100 |

TABLE 3-continued

Antiviral Activity and Cytotoxicity
50% Inhibitory concentration (μM)

| Compound Number[a] | Antiviral Activity Against: | | | Cytotoxicity In Cell Line: | | |
|---|---|---|---|---|---|---|
| | HCMV | | HSV-1 | | | |
| | Plaque | Yield[b] | Plaque | HFF[c] | BSC[c] | KB[d] |
| 57 | 30[e] | 0.03 | >100 | 44[e] | | 81[e] |
| 65 | >100[e] | 8.0 | | >100[e] | | |
| 65a | 32[e] | 3.8[e] | 149[e] | 111[e] | | >100 |
| 67 | 127[e] | 50[e] | >100 | 100[e] | | |
| 81b | 55[e] | | >100 | 161[e] | | 100 |
| 81c | 30 | 1.0 | | 100 | | |
| 87 | 127[e] | 17[e] | >100 | 161[e] | | |
| 90 | >100[e] | 10[e] | >100 | 161 | | >100 |
| 92 | 0.3[e] | 0.01 | | 32[e] | | |
| 103 | 0.5[e] | 0.4 | | 3[e] | | |
| 113 | 30 | 0.5 | 19 | 32 | | 19 |
| 134 | 60[e] | 19 | 28 | >100[e] | | 58[e] |
| 155 | 11 | 0.06 | >100 | 32 | | 70 |
| 156 | >100 | 6.0 | >100 | 100 | | |
| 166 | 69[e] | 149[e] | >100 | 97[e] | | 62 |
| 166a | 24 | | >100 | >100 | >100 | >100 |
| 167 | 16[e] | 168[e] | >100[e] | >100[e] | >100 | >100[e] |
| 182 | 127[e] | 1.1[e] | 152[e] | 99 | | >142[e] |

[a]Number for chemical structure presented in text.
[b]90% inhibitory concentration ($I_{90}$) presented.
[c]Visual cytotoxicity scored on HFF or BSC-1 cells at time of HCMV or HSV-1 plaque enumeration.
[d]Average percent inhibition of DNA, RNA and protein synthesis or cell growth determined in KB cells as described in the text.
[e]Average of two to eight replicate experiments.

(2) Detailed Studies with Compound 45

Because of the potent activity of compound 45 against HCMV and its very low cytotoxicity, this, compound has been studied more extensively. Data in Table 2 below provide evidence that compound 45 is highly specific for human cytomegalovirus. The data show the compound is highly active against this virus but is less active against herpes simplex type 1, herpes simplex type 2, varicella-zoster virus and mouse cytomegalovirus.

TABLE 2

Effect of Compound 45 on the Replication of Herpes Viruses

| Virus | Cell line | 50% Inhibitory Concentration μM | |
|---|---|---|---|
| | | Virus | Cytotoxicity[A] |
| HSV-1 | Human Foreskin Fibroblasts | >57 | −140 |
| HSV-1 | Rabbit Kidney | >284 | >284 |
| HSV-1 | Mouse Embryo Fibroblasts | 28 | −140 |
| HSV-2 | Human Foreskin Fibroblasts | >57 | −140 |
| HSV-2 | Rabbit Kidney | >284 | >284 |
| HSV-2 | Mouse Embryo Fibroblasts | 14 | −140 |
| VZV | Human Foreskin Fibroblasts | 94 | — |
| MCMV | Mouse Embryo Fibroblasts | 57 | −140 |
| HCMV | Human Foreskin Fibroblasts | 1.4 | >>28 |

Figure 3:
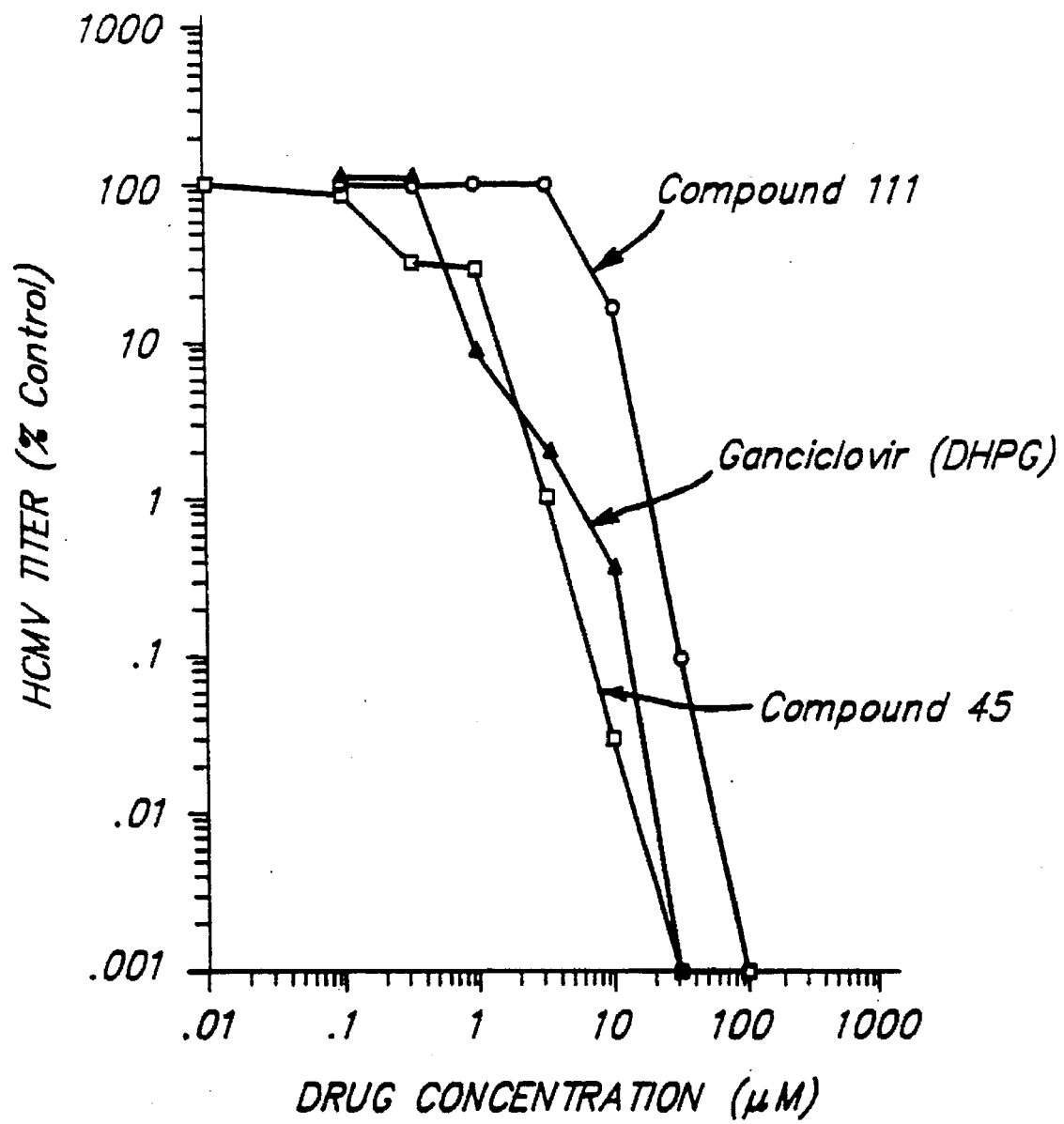
FIG. 3 is a dose response curve comparing the activity against human cytomegalovirus of two polysubstituted benzimidazole nucleosides (compounds 45 and 111) to the known drug ganctclovir in accordance with the principles of the present invention.
Figure 4:
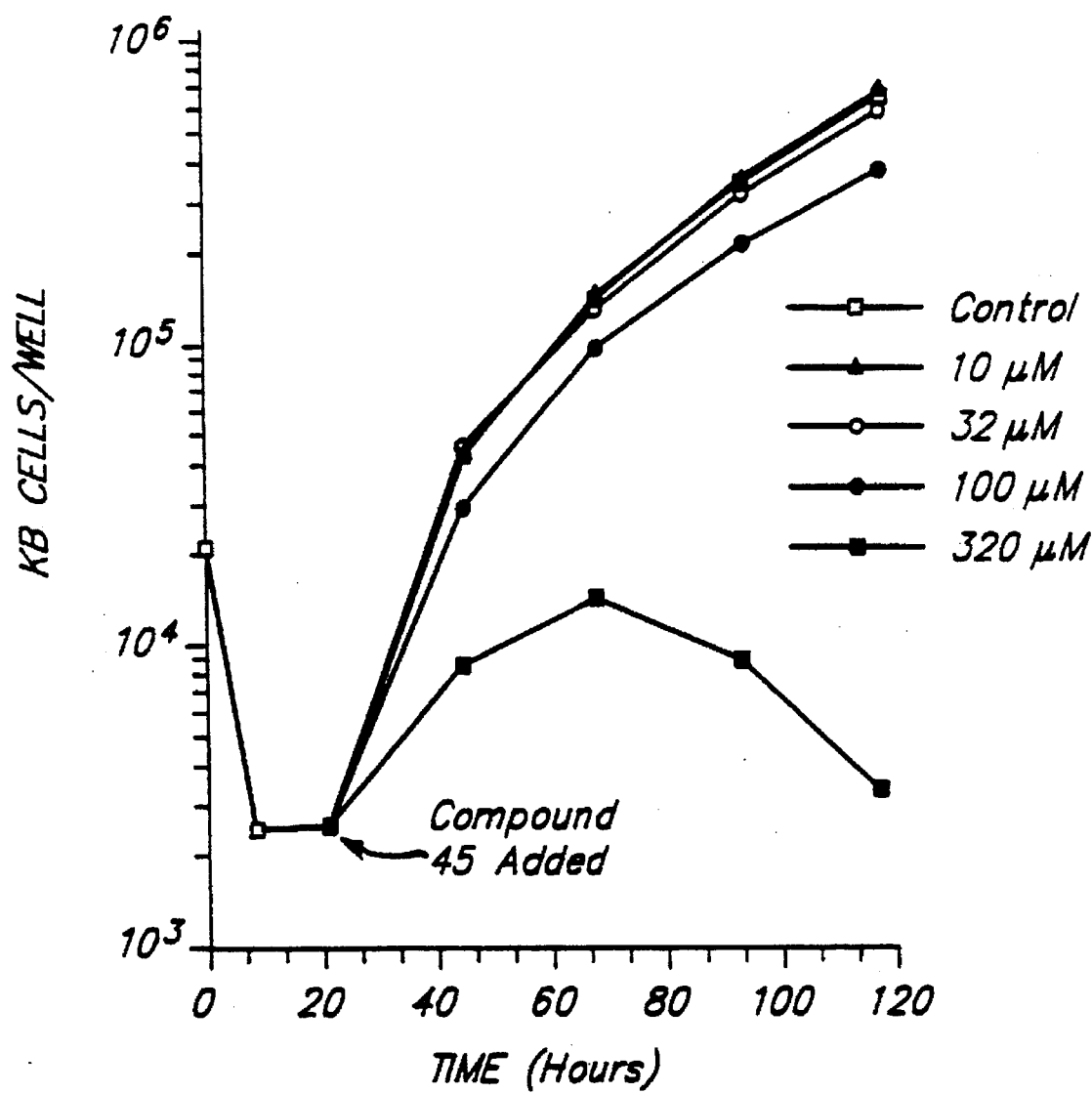
FIG. 4 is a graph illustrating the low degree of cytotoxicity (cell growth inhibition) of a polysubstituted benzimidazole nucleoside (compound 45) in accordance with the principles of the present invention.

Because of its unique potent activity against HCMV, compound 45 was compared to the known anti-HCMV agent ganciclovir as well as to DRB. FIG. 3 shows that compound 45 is. at least as effective as ganciclovir in producing multiple 10-fold reductions in virus titer. Thus, at a concentration of 32 μM compound 45 produced a 100,000-fold reduction in the replication of HCMV. The lack of cytotoxicity of compound 45 in this antiviral activity range is shown in FIG. 4. Data in this figure establish that at 32 to 100 μM compound 45 had little or no effect on the growth of uninfected KB cells. FIG. 5 shows that the inhibitory effects produced by a concentration as high as 320 μM could be reversed by simple removal of the drug from uninfected cells. In contrast FIG. 6 shows the effects of the known compound DRB were fully inhibitory to uninfected cells at 100 μM and these effects could not be reversed by removal of the drug from culture, thereby establishing the cytotoxicity of this compound.

The lack of cytotoxicity of compound 45 was further established by plating efficiency experiments. In these experiments, which measure both the ability of cells to grow and to attach to a substrate, compound 45 had no effect at 100 μM.

(3) Additional Studies With Compounds 45 and 52

Because of the potent activity of compounds 45 and 52 against HCMV and their very low cytotoxicity, these compounds were studied further. Compound 52 also was compared to the known anti-HCMV agent ganciclovir in yield reduction assays. Compound 52 is more effective than ganciclovir in producing multiple 10-fold reductions in virus titer. Thus, at a concentration of 3.2 μM, compound 52 produced nearly a 100,000-fold reduction in the replication of HCMV. In contrast, a 32 μM concentration of ganciclovir was needed to give a similar reduction in HCMV titer. Separate experiments (Table 1) established a lack of cytotoxicity of compound 52 in its antiviral activity range. Data in this figure show that up to 100 μM compound 52 had little or no effect on the growth of uninfected KB cells.

The lack of toxicity of compounds 45 and 52 in their antiviral dose range was further established by examining the effect of both compounds on human bone marrow progenitor cells. Both compounds are at least six-fold less toxic to granulocyte/macrophage progenitor cells than is ganciclovir. Compound 45 is at least four-fold less toxic to erythroid progenitor cells than is ganciciovir, compound 52 is nearly three-fold less toxic. Thus, both compounds are more active against HCMV than is ganciclovir and both are less toxic to human cells.

(4) Drug Combination and Synerqy

Compounds of the invention, such as compounds 45 and 52, provide additional advantages when used in combination with other antiviral drugs. For example, combination of compound 45 with the known antiviral drug ganciclovir results in greater activity (i.e. synergy) against human cytomegalovirus (HCMV) than the use of either agent alone when used at concentrations (approximately 0.1 to 10 μM) most likely achieved in vivo by the administration of therapeutic amounts of each drug. At higher concentrations (approximately 3 to 10 μM) compound 45 also is synergistic against HCMV when used with another known antiviral drug, acyclovir. Likewise the combination of compound 52 with ganciclovir or acyclovir results in synergistic activitiy against HCMV.

Compounds of the invention, such as 45 and 52, could thus be used to treat HCMV infections in AIDS patients already receMng the antiviral drug zidovudine (AZT). Combination of either compound 45 or 52 with AZT provides the advantage of less toxicity over the combination of ganciclovir with AZT. The combination of compound 45 or 52 with AZT produces less cytotoxicity (i.e. antagonism) in cultured human cells than either agent used alone. In contrast, combination of ganciclovir with AZT produces greater cytotoxicity in human cells than the use of either of these drugs alone.

(5) Activity of Ester Prodrugs

Prodrugs of polysubstituted benzimidazoles can be useful for oral administration. For example, ester prodrugs of compounds 45 (compounds 42 and 42a) and 52 (compounds 52a and 52b), respectively, have been prepared and are active against HCMV.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims. Any discrepancy in compound nomenclature in the specification and claims herein should be resolved in deference to the structures and substituents set forth in the charts of FIGS. 1 and 2.

What is claimed is:

1. An antiviral compound selected from the group consisting of compounds having the following formula, and pharmaceutically acceptable salts thereof:

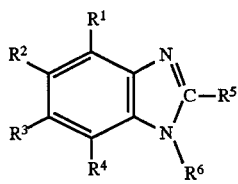

wherein:

$R_1$ is H, $R_2$ is Cl, $R_3$ is Cl, $R_4$ is H, $R_5$ is Br and $R_6$ is H (denoted compound 7 in the text);

$R_1$ is H, $R_2$ is Cl, and $R_3$ is F, $R_4$ is H, $R_5$ is Cl and $R_6$ is H (denoted compound 12c in the text);

$R_1$ is H, $R_2$ is I, $R_3$ is $NO_2$, $R_4$ is H, $R_5$ is Cl and $R_6$ is H (denoted compound 26 in the text);

$R_1$ is Cl, $R_2$ is H, $R_3$ is Cl, $R_4$ is H, $R_5$ is Cl and $R_6$ is H (denoted compound 32 in the text);

$R_1$ is H; $R_2$ is I, $R_3$ is I, $R_4$ is H, $R_5$ is Cl and $R_6$ is H (denoted compound 41 in the text); and $R_1$ is Cl, $R_2$ is H, $R_3$ is $CF_3$, $R_4$ is H, $R_5$ is Cl and $R_6$ is H (denoted compound 41c in the text).

2. The antiviral compound of claim 1, wherein $R_1$ is H, $R_2$ is Cl, $R_3$ is Cl, $R_4$ is H, $R_5$ is Br and $R_6$ is H (denoted compound 7 in the text).

3. The antiviral compound of claim 1, wherein $R_1$ is H, $R_2$ is Cl, $R_3$ is F, $R_4$ is H, $R_5$ is Cl and $R_6$ is H (denoted compound 12c in the text).

4. The antiviral compound of claim 1, wherein $R_1$ is H, $R_2$ is I, $R_3$ is $NO_2$, $R_4$ is H, $R_5$ is Cl and $R_6$ is H (denoted compound 26 in the text).

5. The antiviral compound of claim 1, wherein $R_1$ is Cl, $R_2$ is H, $R_3$ is Cl, $R_4$ is H, $R_5$ is Cl and $R_6$ is H (denoted compound 32 in the text).

6. The antiviral compound of claim 1, wherein $R_1$ is H, $R_2$ is I, $R_3$ is I, $R_4$ is H, $R_5$ is Cl and $R_6$ is H (denoted compound 41 in the text).

7. The antiviral compound of claim 1, wherein $R_1$ is Cl, $R_2$ is H, $R_3$ is $CF_3$, $R_4$ is H, $R_5$ is Cl and $R_6$ is H (denoted compound 41e in the text).

8. An antiviral composition comprising a pharmaceutically acceptable carrier and a compound selected from the group consisting of compounds having the following formula, and pharmaceutically acceptable salts thereof:

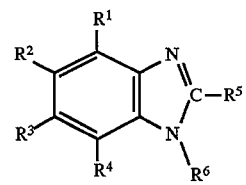

wherein:

$R_1$ is H, $R_2$ is Cl, $R_3$ is Cl, $R_4$ is H, $R_5$ is Br and $R_6$ is H (denoted compound 7 in the text);

$R_1$ is H, $R_2$ is Cl, $R_3$ is F, $R_4$ is H, $R_5$ is Cl and $R_6$ is H (denoted compound 12c in the text);

$R_1$ is H, $R_2$ is I, $R_3$ is $NO_2$, $R_4$ is H, $R_5$ is Cl and $R_6$ is H (denoted compound 26 in the text);

$R_1$ is Cl, $R_2$ is H, $R_3$ is Cl, $R_4$ is H, $R_5$ is Cl and $R_6$ is H (denoted compound 32 in the text);

$R_1$ is H, $R_2$ is I, $R_3$ is I, $R_4$ is H, $R_5$ is Cl and $R_6$ is H (denoted compound 41 in the text); and $R_1$ is Cl, $R_2$ is H, $R_3$ is $CF_3$, $R_4$ is H, $R_5$ is Cl and $R_6$ is H (denoted compound 41c in the test).

9. The antiviral composition of claim 8, wherein $R_1$ is H, $R_2$ is Cl, $R_3$ is Cl, $R_4$ is H, $R_5$ is Br and $R_6$ is H (denoted compound 7 in the text).

10. The antiviral composition of claim 8, wherein $R_1$ is H, $R_2$ is Cl, $R_3$ is F, $R_4$ is H, $R_5$ is Cl and $R_6$ is H (denoted compound 12c in the text).

11. The antiviral composition of claim 8, wherein $R_1$ is H, $R_2$ is I, $R_3$ is $NO_2$, $R_4$ is H, $R_5$ is Cl and $R_6$ is H (denoted compound 26 in the text).

12. The antiviral composition of claim 8, wherein $R_1$ is Cl, $R_2$ is H, $R_3$ is Cl, $R_4$ is H, $R_5$ is Cl and $R_6$ is H (denoted compound 32 in the text).

13. The antiviral composition of claim 8, wherein $R_1$ is H, $R_2$ is I, $R_3$ is I, $R_4$ is H, $R_5$ is Cl and $R_6$ is H (denoted compound 41 in the text).

14. The antiviral composition of claim 8, wherein $R_1$ is Cl, $R_2$ is H, $R_3$ is $CF_3$, $R_4$ is H, $R_5$ is Cl and $R_6$ is H (denoted compound. 41c in the text).

15. The antiviral composition of claim 8, further comprising ganciclovir.

16. A method for treating a herpes viral infection comprising administering to the infected host a therapeutically effective amount a compound, or pharmaceutically acceptable salts or formulations thereof, selected from the group consisting of compounds having the following formula:

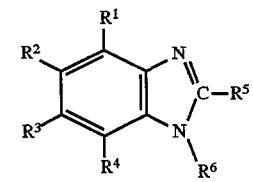

wherein:

$R_1$ is H, $R_2$ is Cl, $R_3$ is Cl, $R_4$ is H, $R_5$ is Br and $R_6$ is H (denoted compound 7 in the text);

$R_1$ is H, $R_2$ is Cl, $R_3$ is F, $R_4$ is H, $R_5$ is Cl and $R_6$ is H (denoted compound 12c in the text);

$R_1$ is Cl, $R_2$ is Cl, $R_3$ is Cl, $R_4$ is H, $R_5$ is Cl and $R_6$ is H (denoted compound 13 is the text);

$R_1$ is H, $R_2$ is $NO_2$, $R_3$ is H, $R_4$ is H, $R_5$ is Cl and $R_6$ is H (denoted compound 19 in the text);

$R_1$ is H, $R_2$ is I, $R_3$ is $NO_2$, $R_4$ is H, $R_5$ is Cl and $R_6$ is H (denoted compound 26 in the text);

$R_1$ is Cl, $R_2$ is H, $R_3$ is Cl, $R_4$ is H, $R_5$ is Cl and $R_6$ is H (denoted compound 32 in the text);

$R_1$ is H, $R_2$ is I, $R_3$ is I, $R_4$ is H, $R_5$ is Cl and $R_6$ is H (denoted compound 41 in the text); and $R_1$ is Cl, $R_2$ is H, $R_3$ is $CF_3$, $R_4$ is H, $R_5$ is Cl and $R_6$ is H (denoted compound 41c in the text).

17. The method of claim 16, wherein $R_1$ is H, $R_2$ is Cl, $R_3$ is Cl, $R_4$ is H, $R_5$ is Br and $R_6$ is H (denoted compound 7 in the text).

18. The method of claim 16, wherein $R_1$ is H, $R_2$ is Cl, $R_3$ is F, $R_4$ is H, $R_5$ is Cl and $R_6$ is H (denoted compound 12c in the text).

19. The method of claim 16, wherein $R_1$ is Cl, $R_2$ is Cl, $R_3$ is Cl, $R_4$ is H, $R_5$ is Cl and $R_6$ is H (denoted compound 13 in the text).

20. The method of claim 16, wherein $R_1$ is H, $R_2$ is $NO_2$, $R_3$ is H, $R_4$ is H, $R_5$ is Cl and $R_6$ is H (denoted compound 19 in the text).

21. The method of claim 16, wherein $R_1$ is H, $R_2$ is I, $R_3$ is $NO_2$, $R_4$ is H, $R_5$ is Cl and $R_6$ is H (denoted compound 26 in the text).

22. The method of claim 16, wherein $R_1$ is Cl, $R_2$ is H, $R_3$ is Cl, $R_4$ is H, $R_5$ is Cl and $R_6$ is H (denoted compound 32 in the text).

23. The method of claim 16, wherein $R_1$ is H, $R_2$ is I, $R_3$ is I, $R_4$ is H, $R_5$ is Cl and $R_6$ is H (denoted compound 41 in the text).

24. The method of claim 16, wherein $R_1$ is Cl, $R_2$ is H, $R_3$ is $CF_3$, $R_4$ is H, $R_5$ is Cl and $R_6$ is H (denoted compound 41e in the text).

* * * * *

UNITED STATES PATENT AND TRADEMARK OFFICE

CERTIFICATE OF CORRECTION

PATENT NO. : 5,654,283

DATED : August 5, 1997

INVENTOR(S) : Leroy B. Townsend *et al.*

It is certified that error appears in the above-identified patent and that said Letters Patent is hereby corrected as shown below:

In claim 7, at line 3, "41e" should be replaced with "41c".

In claim 8, at the last line, "test" should be replaced with "text".

In claim 16, at line 1, "vital" should be replaced with "viral".

In claim 24, at line 3, "41e" should be replaced with "41c".

Signed and Sealed this

Twenty-eighth Day of October, 1997

*Attest:*

BRUCE LEHMAN

*Attesting Officer*   *Commissioner of Patents and Trademarks*